(12) United States Patent
Ferguson et al.

(10) Patent No.: US 11,028,089 B2
(45) Date of Patent: Jun. 8, 2021

(54) PYRIMIDO-DIAZEPINONE KINASE SCAFFOLD COMPOUNDS AND METHODS OF TREATING DCLK1/2-MEDIATED DISORDERS

(71) Applicant: DANA-FARBER CANCER INSTITUTE, INC., Boston, MA (US)

(72) Inventors: Fleur M. Ferguson, Cambridge, MA (US); Nathanael S. Gray, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/343,102

(22) PCT Filed: Oct. 18, 2017

(86) PCT No.: PCT/US2017/057126
§ 371 (c)(1),
(2) Date: Apr. 18, 2019

(87) PCT Pub. No.: WO2018/075608
PCT Pub. Date: Apr. 26, 2018

(65) Prior Publication Data
US 2019/0315753 A1 Oct. 17, 2019

Related U.S. Application Data

(60) Provisional application No. 62/409,457, filed on Oct. 18, 2016.

(51) Int. Cl.
*A61K 31/551* (2006.01)
*A61P 35/00* (2006.01)
*C07D 487/04* (2006.01)

(52) U.S. Cl.
CPC ............ *C07D 487/04* (2013.01); *A61P 35/00* (2018.01)

(58) Field of Classification Search
CPC ...... A61K 31/551; C07D 487/04; A61P 35/00
See application file for complete search history.

(56) References Cited

U.S. PATENT DOCUMENTS

| 9,464,091 B2* | 10/2016 | Gray | C07D 471/14 |
| 9,676,792 B2* | 6/2017 | Gray | C07D 495/14 |
| 9,695,172 B2* | 7/2017 | Bradner | C07D 487/04 |
| 9,750,816 B2* | 9/2017 | Bradner | A61K 47/54 |
| 9,821,068 B2* | 11/2017 | Bradner | A61K 47/542 |
| 10,125,114 B2* | 11/2018 | Bradner | C07D 495/14 |
| 10,189,861 B2* | 1/2019 | Gray | C07D 487/04 |
| 10,308,653 B2* | 6/2019 | Bradner | C07D 487/04 |
| 10,457,692 B2* | 10/2019 | Gray | C07D 471/18 |
| 2012/0040961 A1 | 2/2012 | Gray et al. | |
| 2014/0171422 A1 | 6/2014 | Otsubo et al. | |
| 2016/0024115 A1 | 1/2016 | Gray et al. | |
| 2016/0176916 A1 | 6/2016 | Bradner et al. | |
| 2017/0008895 A1* | 1/2017 | Bradner | A61K 31/5513 |

FOREIGN PATENT DOCUMENTS

| EP | 3424929 A1 | 9/2019 |
| WO | WO 2014/160430 | * 10/2014 |
| WO | 2015/117083 A1 | 8/2015 |
| WO | 2015/117087 A1 | 8/2015 |

OTHER PUBLICATIONS

Patel et al., Biochemical and Structural Insights Into Doublecortin-like Kinase Domain 1, Structure, vol. 24, No. 9, pp. 1550-1561. (Year: 2016).*
Ferguson et al., Discovery of a Series of 5,11-Dihydro-6H-Benzo[e]]pyrimido[5,4-b][1,4]diazepin-6-ones as Selective PI3K-delta/gamma Inhibitiors, ACS Medicinal Chemistry Letters, vol. 7, No. 10, pp. 908-912. (Year: 2016).*
Lin et al., ERK5 Kinase Activity is Not Required for Cellular Immune Response, bioRxiv, Immunology, p. 38513/1-38513/47. (Year: 2016).*
Kanhed et al., Benzo[e]pyrimido[5,4-b][1,4]diazepin-6(11H)-one Derivatives as Aurora A Kinase Inhibitors: LQTA-QSAR Analysis and Detailed Systematic Validation of the Developed Model, Molecular Diversity, vol. 19, No. 4, pp. 965-974. (Year: 2015).*
Munoz et al., Optimisation of LRRK2 Inhibitors and Assessment of Functional Efficacy in Cell-Based Models of Neuroinflammation, European Journal of Medicinal Chemistry, vol. 95, pp. 29-34. (Year: 2015).*
Weygant et al., Small Molecule Kinase Inhibitor LRRK2-IN-1 Demonstrates Potent Activity Against Colorectal and Pancreatic Cancer Through Inhibition of Doublecortin-Like Kinase 1, Molecular Cancer, vol. 13, p. 103/1-103/14. (Year: 2014).*
Sureban et al., XMD8-92 Inhibits Pancreatic Tumor Xenograft Growth via a DCLK1-Dependent Mechanism, Cancer Letters, vol. 351, No. 1, pp. 151-161 (Year: 2014).*
Leurman et al., Phosphoproteomic Evaluation of Pharmacological Inhibition of Leucine-Rich Repeat Kinase 2 Reveals Significient Off-Target Effects of LRRK-2-IN-1, Journal of Neurochemistry, vol. 128, No. 4, pp. 561-576. (Year: 2014).*
Deng et al., Structural Determinants For ERK5 (MAPK7) and Leucine Rich Repeat Kinase 2 Activities of Benzo[e]pyrimido-[5,4-b] diazepine-6(11H)-ones, European Journal of Medicinal Chemistry, vol. 70, pp. 758-767. (Year: 2013).*
Elkins et al., X-Ray Crystal Structure of ERK5 (MAPK7) in Complex with a Specific Inhibitor, Journal of Medicinal Chemistry, vol. 56 , No. 11, pp. 4413-4421. (Year: 2013).*

(Continued)

*Primary Examiner* — Brenda L Coleman
(74) *Attorney, Agent, or Firm* — Burns & Levinson, LLP; Daniel W. Clarke

(57) ABSTRACT

The present invention relates to use of pyrimido-diazepinone compounds that are able to modulate protein kinases such as doublecortin-like kinase (DCLK1) and doublecortin-like kinase 2 (DCLK2), which are members of serine/threonine-protein kinase family and $Ca^{2+}$/calmodulin-dependent protein kinase class of enzymes, and the use of such compounds in the treatment of various diseases, disorders or conditions.

11 Claims, 3 Drawing Sheets

(56) References Cited

OTHER PUBLICATIONS

Kwiatkowski et al., Selective Aurora Kinase Inhibitors Identified Using a Taxol-Induced Checkpoint Sensitivity Screen, ACS Chemical Biology, vol. 7, No. 1, pp. 185-196. (Year: 2012).*

Miduturu et al., High-Throughput Kinase Profiling: A More Efficient Approach Toward the Discovery of New Kinase Inhibitors, Chemistry & Biology, vol. 18, No. 7, pp. 868-879. (Year: 2011).*

Deng et al., Discovery of a Benzo[e]pyrimido-[5,4-b][1,4]diazepin-6(11H)-one as a Potent and Selective Inhibitor of Big MAP Kinase 1, ACS Medicinal Chemistry Letters, vol. 2, No. 3, pp. 195-200. (Year: 2011).*

Ferguson, Fleur M., et al., "Discovery of a Selective Inhibitor of Doublecortin Like Kinase 1", Nat. Chem. Biol. Apr. 6, 2020, doi: 10.1038/s41589-020-0506-0.

Ito, Hiromitsu, et al., "Dominant Expression of DCLK1 in Human Pancreatic Cancer Stem Cells Accelerates Tumor Invasion and Metastasis", PLOS One, 2016, vol. 11, No. 1, e0146564.

Westphalen, C. Benedikt, et al., "Long-Lived Intestinal Tuft Cells Serve as Colon Cancer-Initiating Cells", J. Clin. Invest., 2014, vol. 124, No. 3, pp. 1283-1295.

Weygant, Nathaniel, et al., "Small Molecule Kinase Inhibitor LRRK2-IN-1 Demonstrates Potent Activity Against Colorectal and Pancreatic Cancer Through Inhibition of Doublecortin-like Kinase 1", Mol. Cancer, 2014, vol. 13, No. 103.

\* cited by examiner

PYRIMIDO-DIAZEPINONE KINASE SCAFFOLD COMPOUNDS AND METHODS OF TREATING DCLK1/2-MEDIATED DISORDERS

RELATED APPLICATIONS

This application is a national stage application, filed under 35 U.S.C. § 371, of International Application No. PCT/US2017/057126, filed Oct. 18, 2017, which claims the benefit of priority under 35 U.S.C. § 119(e) to U.S. Provisional Application No. 62/409,457, filed Oct. 18, 2016, each of which is incorporated herein by reference in its entirety.

TECHNICAL FIELD

The present invention relates to pyrimido-diazepinone compounds which are able to modulate protein kinases such as doublecortin-like kinase 1 (DCLK1) and doublecortin-like kinase 2 (DCLK2), which are members of serine/threonine-protein kinase family and $Ca^{2+}$/calmodulin-dependent protein kinase class of enzymes, and the use of such compounds in the treatment of various diseases, disorders or conditions.

BACKGROUND OF THE INVENTION

Protein kinases represent a large family of proteins, which play a central role in the regulation of a wide variety of cellular processes and maintaining control over cellular function. Protein kinases constitute a large family of structurally related enzymes that are responsible for the control of a variety of signal transduction processes within the cell (see Hardie, G and Hanks, S. The Protein Kinase Facts Book, I and II, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids etc).

In general, protein kinases mediate intracellular signaling by catalyzing a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., shock, heat shock, ultraviolet radiation, bacterial endotoxin, and H2O2), cytokines (e.g., interleukin-1 (IL-I) and tumor necrosis factor alpha (TNF-a), and growth factors (e.g., granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

Described herein are compounds that inhibit the activity of one or more isoforms of the protein kinase DCLK1/2 and are, therefore, expected to be useful in the treatment of kinase-associated diseases.

SUMMARY OF THE INVENTION

In one aspect, the invention provides a method of treating a disease mediated by a kinase such as doublecortin-like kinase 1 (DCLK1) and/or doublecortin-like kinase 2 (DCLK2). The method comprises administering of a kinase inhibitor compound, e.g., a compound of formula A:

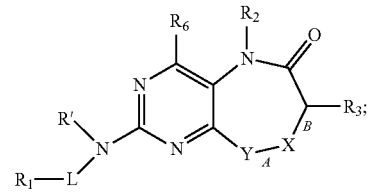

(A)

or a pharmaceutically acceptable salt, ester or prodrug thereof,
wherein,
X is $CHR_4$, $CR_4$, NH, $NR_4$ or N;
Y is $NR_5$, N, S, SO, $SO_2$, O, $CHR_5$, or $CR_5$; wherein at least one of X and Y is NH, $NR_4$, $NR_5$, N, S, SO, $SO_2$, or O;
A is a single bond or double bond;
B is a single bond or double bond, wherein both A and B are not double bonds;
R' is H or alkyl;
L is absent, S, SO, $SO_2$, or CO;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;
$R_2$ is hydrogen or optionally substituted alkyl;
$R_3$ is hydrogen, alkyl, alkenyl, aryl, arylalkyl, heteroaryl, heterocyclic, or carbocyclic, each of which may be optionally substituted;
$R_4$ is hydrogen, alkyl, alkenyl, aryl, arylalkyl, heteroaryl, heterocyclic, or carbocyclic, each of which may be optionally substituted;
$R_5$ is hydrogen, alkyl, alkenyl, aryl, arylalkyl, heteroaryl, heterocyclic, or carbocyclic, each of which may be optionally substituted;
or $R_3$ and X, together with the atoms to which they are attached, form a 3-8 membered carbocyclic, aryl, heterocyclic, or heteroaryl; each of which is optionally substituted;
or X and Y, together with the atoms to which they are attached, form a 3-8 membered carbocyclic, aryl, heterocyclic, or heteroaryl; each of which is optionally substituted; and
$R_6$ is hydrogen or optionally substituted alkyl.

In one aspect, the method of treating a disease in a subject mediated by doublecortin-like kinase (DCLK1) and/or DCLK2 comprises administering to the subject a compound of formula F-1:

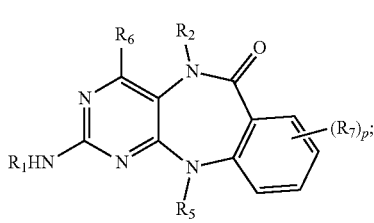

(F-1)

or a pharmaceutically acceptable salt, ester or prodrug thereof, wherein,

R₁ is alkyl, aryl, heteroaryl, heterocyclic, or carbocyclic, wherein R₁ may be optionally substituted;

R₂ is hydrogen or optionally substituted alkyl;

R₅ is hydrogen, optionally substituted alkyl, optionally substituted aralkyl, or optionally substituted carbocyclic; and R₆ is hydrogen or optionally substituted alkyl;

each R₇ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and p is 0-4.

In some embodiments, R₅ is methyl.

In some embodiments, R₂ is unsubstituted alkyl.

In some embodiments, R₂ is methyl, ethyl, propyl, or iso-propyl, each of which may be optionally substituted with one or more halogen.

In some embodiments, R₂ is —CH₂—CH₂F, —CH₂—CHF₂, or —CH₂—CF₃.

In some embodiments, the compound is of formula F-1-a:

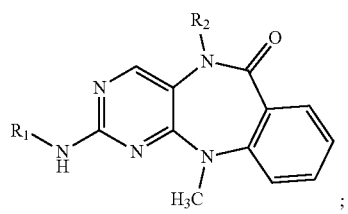

(F-1-a)

or a pharmaceutically acceptable salt, ester or prodrug thereof.

In embodiments, R₁ is methyl, ethyl, propyl, iso-propyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In embodiments, R₁ is phenyl or pyridyl, each of which may be optionally substituted.

In some embodiments, R₁ is substituted with 0-4 substituents, selected from halo, nitro, cyano, hydroxyl, amino, NH(R_A), N(R_A)(R_A), CO₂H, C(O)R_A, C(O)OR_A, C(O)NH₂, C(O)NH(R_A), C(O)N(R_A)(R_A), alkyl, aryl, arylalkyl, alkoxy, heteroaryl, heterocyclic, and carbocyclic, each of which may be further substituted; wherein each R_A is independently selected from alkyl, alkenyl, carbocyclic, aryl, heteroaryl, and heterocyclic, or two R_A on the same atom combine to form a heterocyclic, each of which may be further substituted.

In some embodiments, R₁ is substituted with 0-4 substituents, selected from alkoxy, CO₂Me,

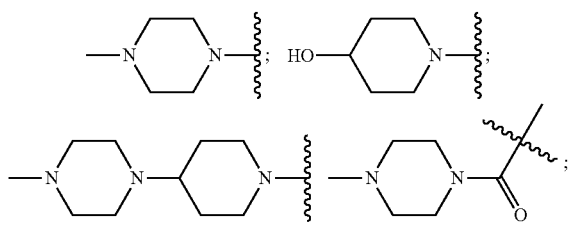

In embodiments, R₁ is phenyl, pyridyl, pyrimidinyl, furyl, pyrrolyl, pyrazolyl, imidazolyl, thienyl, or bicyclo[1.1.1]pent-1-yl, each of which may be optionally substituted.

In some embodiments, R₁ is substituted with 0-4 substituents, selected from halo, nitro, cyano, hydroxyl, amino, NH(R_A), N(R_A)(R_A), CO₂H, C(O)R_A, C(O)OR_A, C(O)NH₂, C(O)NH(R_A), C(O)N(R_A)(R_A), alkyl, aryl, arylalkyl, alkoxy, heteroaryl, heterocyclic, carbocyclic, SO₂(R_A), SO₃(R_A), SO₂N(R_A)(R_A), SO₂NH(R_A), SO₂NH₂, PO(OR_A)(OR_A), or PO(OR_A)(R_A), each of which may be further substituted; and each R_A is independently selected from alkyl, alkenyl, carbocyclic, aryl, heteroaryl, and heterocyclic, or two R_A on the same atom combine to form a heterocyclic, each of which may be further substituted.

In some embodiments, R₁ is selected from the group consisting of:

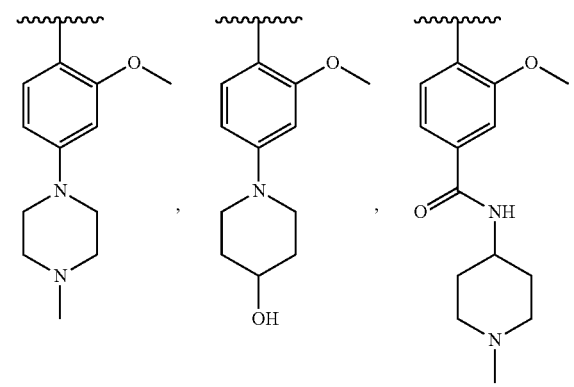

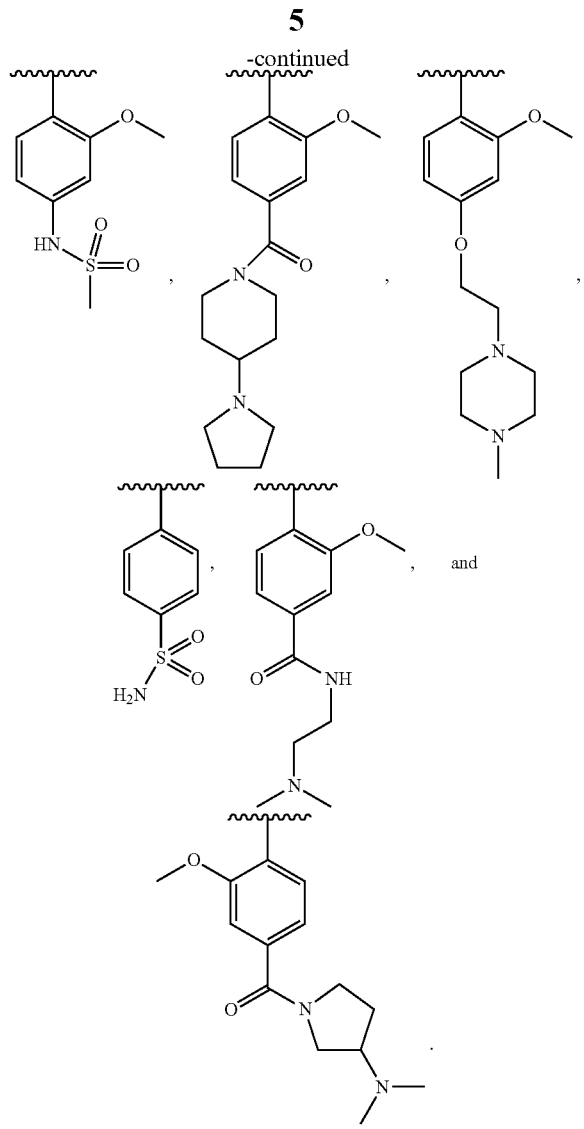

In embodiments, the compound inhibits DCLK1 and/or DCLK2.

In embodiments, the disease is cancer or a proliferation disease.

In some embodiments, the disease is lung, colon, breast, prostate, liver, pancreas, brain, kidney, ovaries, stomach, skin, and bone cancers, gastric, breast, pancreatic cancer, glioma, and hepatocellular carcinoma, papillary renal carcinoma, head and neck squamous cell carcinoma, leukemias, lymphomas, myelomas, solid tumors, or blood-borne cancers (e.g., chronic lymphocytic leukemia (CLL), follicular lymphoma (FL), or indolent non-Hodgkin's lymphoma (iNHL).

In some embodiments, the disease is Barretts' esophagus, esophageal cancer, salivary gland malignancies, colon and colorectal cancer, intestinal cancer, gastric cancer, pancreatic cancer, skin cancer or neuroblastoma.

In embodiments, the disease is a liver disease.

In some embodiments, the disease is a fatty liver disease, non-alcoholic fatty liver disease (NAFLD), non-alcoholic steatohepatitis (NASH), cirrhosis, fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Wolmans disease, or acute fatty liver of pregnancy.

In embodiments, the disease is a neurodegenerative disease.

In some embodiments, the disease is Alzheimer's disease (AD), Parkinson's disease (PD), Huntington's (HD) diseases, amyotrophic lateral sclerosis (ALS), spinal muscular atrophy (SMA), schizophrenia, attention-deficit/hyperactivity disorder (ADHD), fetal alcohol syndrome and diabetic encephalopathy.

In embodiments, the subject is administered an additional therapeutic agent.

In embodiments, said additional therapeutic agent are administered simultaneously or sequentially.

In embodiments, said additional therapeutic agent is a chemotherapeutic agent.

In one aspect, a method for reducing doublecortin-like kinase (DCLK1/2)-dependent cell growth comprises contacting a cell with a compound of formula F-1:

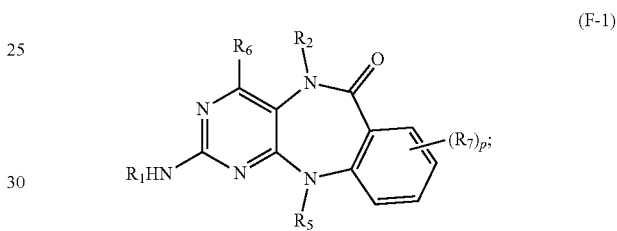

or a pharmaceutically acceptable salt, ester or prodrug thereof,
wherein, $R_1$ is alkyl, aryl, heteroaryl, heterocyclic, or carbocyclic, wherein $R_1$ may be optionally substituted;

$R_2$ is hydrogen or optionally substituted alkyl;

$R_5$ is hydrogen, optionally substituted alkyl, optionally substituted aralkyl, or optionally substituted carbocyclic; and $R_6$ is hydrogen or optionally substituted alkyl;

each $R_7$ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and p is 0-4.

In another aspect, the method of inhibiting doublecortin-like kinase (DCLK1/2) in a subject identified as in need of such treatment comprises administering a compound of formula F-1:

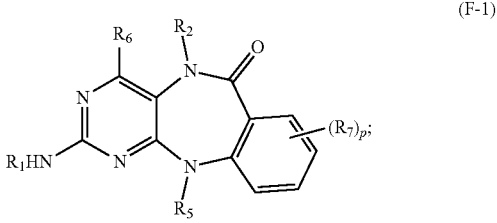

or a pharmaceutically acceptable salt, ester or prodrug thereof, wherein,

R₁ is alkyl, aryl, heteroaryl, heterocyclic, or carbocyclic, wherein R₁ may be optionally substituted;

R₂ is hydrogen or optionally substituted alkyl;

R₅ is hydrogen, optionally substituted alkyl, optionally substituted aralkyl, or optionally substituted carbocyclic; and R₆ is hydrogen or optionally substituted alkyl;

each R₇ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and p is 0-4.

In embodiments, the subject is a human.

In embodiments, the compound has a Ki for inhibiting the doublecortin-like kinase (DCLK1/2) less than about 1 μM, less than about 500 nM, less than about 100 nM, less than about 50 nM, less than about 40 nM, less than about 30 nM, less than about 20 nM, or less than about 15 nM.

In some embodiments, R₅ is methyl.

In some embodiments, R₂ is unsubstituted alkyl.

In some embodiments, R₂ is methyl, ethyl, propyl, or iso-propyl, each of which may be optionally substituted with one or more halogen.

In some embodiments, R₂ is —CH₂—CH₂F, —CH₂—CHF₂, or —CH₂—CF₃.

In embodiments, the compound is of formula F-1-a:

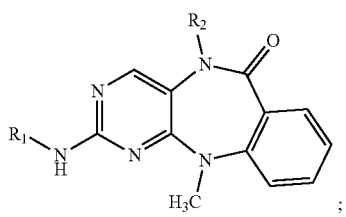

(F-1-a)

or a pharmaceutically acceptable salt, ester or prodrug thereof.

In embodiments, R₁ is methyl, ethyl, propyl, iso-propyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In embodiments, R₁ is phenyl or pyridyl, each of which may be optionally substituted.

In some embodiments, R₁ is substituted with 0-4 substituents, selected from halo, nitro, cyano, hydroxyl, amino, NH(R$_A$), N(R$_A$)(R$_A$), CO₂H, C(O)R$_A$, C(O)OR$_A$, C(O)NH₂, C(O)NH(R$_A$), C(O)N(R$_A$)(R$_A$), alkyl, aryl, arylalkyl, alkoxy, heteroaryl, heterocyclic, and carbocyclic, each of which may be further substituted;

wherein each R$_A$ is independently selected from alkyl, alkenyl, carbocyclic, aryl, heteroaryl, and heterocyclic, or two R$_A$ on the same atom combine to form a heterocyclic, each of which may be further substituted.

In some embodiments, R₁ is substituted with 0-4 substituents, selected from alkoxy, CO₂Me,

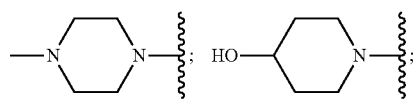

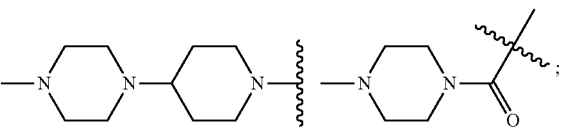

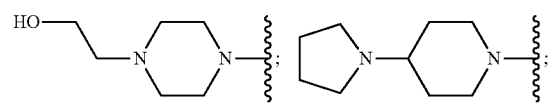

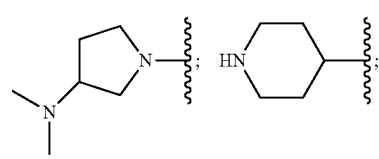

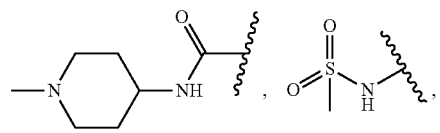

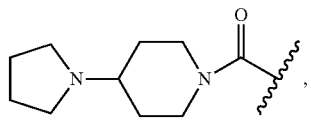

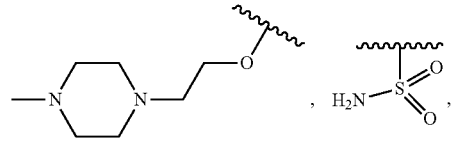

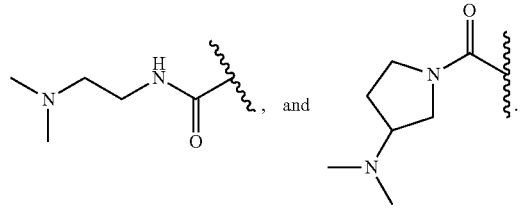

In embodiments, R₁ is phenyl, pyridyl, pyrimidinyl, furyl, pyrrolyl, pyrazolyl, imidazolyl, thienyl, or bicyclo[1.1.1]pent-1-yl, each of which may be optionally substituted.

In some embodiments, R₁ is substituted with 0-4 substituents, selected from halo, nitro, cyano, hydroxyl, amino, NH(R$_A$), N(R$_A$)(R$_A$), CO₂H, C(O)R$_A$, C(O)OR$_A$, C(O)NH₂, C(O)NH(R$_A$), C(O)N(R$_A$)(R$_A$), alkyl, aryl, arylalkyl, alkoxy, heteroaryl, heterocyclic, carbocyclic, SO₂(R$_A$), SO₃(R$_A$), S₂N(R$_A$) (R$_A$), SO₂NH(R$_A$), SO₂NH₂, PO(OR$_A$)(OR$_A$), or PO(OR$_A$)(R$_A$), each of which may be further substituted; and wherein each R$_A$ is independently selected from alkyl, alkenyl, carbocyclic, aryl, heteroaryl, and heterocyclic, or two R$_A$ on the same atom combine to form a heterocyclic, each of which may be further substituted.

In some embodiments, R₁ is selected from the group consisting of:

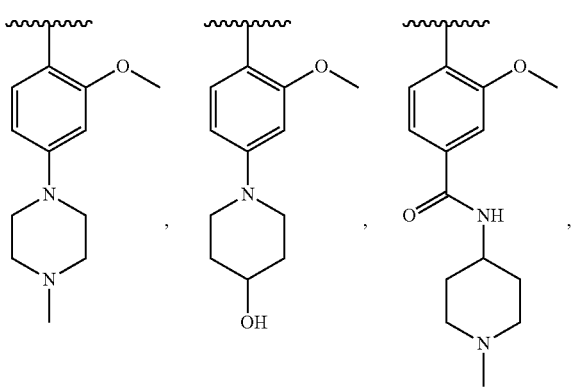

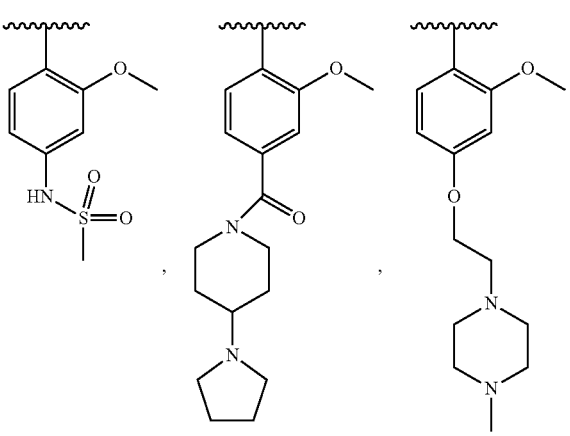

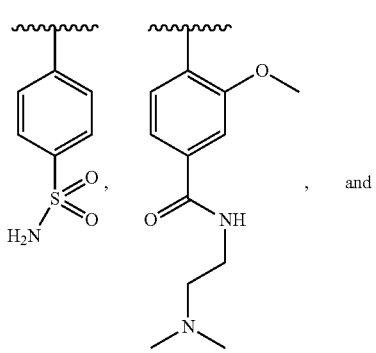

, and

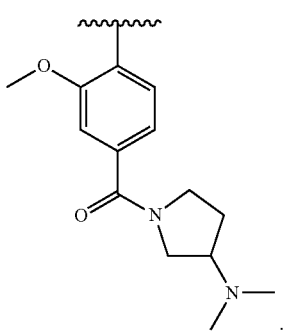

.

In one aspect, the method of treating a disease in a subject mediated by a kinase such as doublecortin-like kinase (DCLK1/2) comprises administering to the subject a compound of formula A-1:

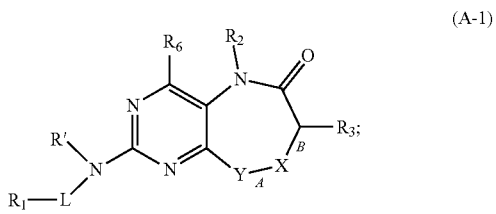

(A-1)

or a pharmaceutically acceptable salt, ester or prodrug thereof, wherein,

X is $CHR_4$, $CR_4$, NH, $NR_4$ or N;

Y is $NR_5$, N, S, SO, $SO_2$, O, $CHR_5$, or $CR_5$; wherein at least one of X and Y is NH, $NR_4$, $NR_5$, N, S, SO, $SO_2$, or O;

A is a single bond or double bond;

B is a single bond or double bond, wherein both A and B are not double bonds;

R' is H or alkyl;

L is absent, S, SO, $SO_2$, or CO;

$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;

$R_2$ is hydrogen or optionally substituted alkyl;

$R_3$ is hydrogen, alkyl, alkenyl, aryl, arylalkyl, heteroaryl, heterocyclic, or carbocyclic, each of which may be optionally substituted;

$R_4$ is hydrogen, alkyl, alkenyl, aryl, arylalkyl, heteroaryl, heterocyclic, or carbocyclic, each of which may be optionally substituted;

$R_5$ is hydrogen, alkyl, alkenyl, aryl, arylalkyl, heteroaryl, heterocyclic, or carbocyclic, each of which may be optionally substituted;

or $R_3$ and X, together with the atoms to which they are attached, form a 3-8 membered carbocyclic, aryl, heterocyclic, or heteroaryl; each of which is optionally substituted;

or X and Y, together with the atoms to which they are attached, form a 3-8 membered carbocyclic, aryl, heterocyclic, or heteroaryl; each of which is optionally substituted; and $R_6$ is hydrogen or optionally substituted alkyl.

In another aspect, the method for reducing doublecortin-like kinase (DCLK1/2)-dependent cell growth comprising contacting a cell with a compound of formula A-1, or a pharmaceutically acceptable salt, ester or prodrug thereof.

In another aspect, the method of inhibiting doublecortin-like kinase (DCLK1/2) in a subject identified as in need of such treatment, comprising administering a compound of formula A-1, or a pharmaceutically acceptable salt, ester or prodrug thereof.

In embodiments, the compound has a structure according to formula B-1:

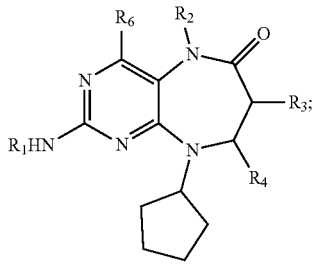

(B-1)

or a pharmaceutically acceptable salt, ester or prodrug thereof,
wherein,
R₁ is aryl, or heteroaryl, wherein R₁ may be optionally substituted;
R₂ is hydrogen or optionally substituted alkyl;
R₃ is hydrogen or methyl;
R₄ is hydrogen or methyl; and
R₆ is hydrogen.

In embodiments, the compound has a structure according to formula C-1:

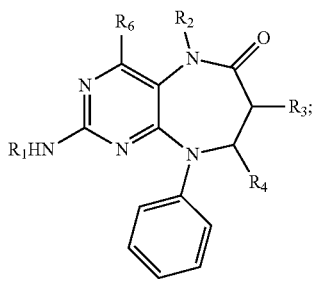

(C-1)

or a pharmaceutically acceptable salt, ester or prodrug thereof,
wherein,
R₁ is aryl, heteroaryl, which may be optionally substituted;
R₂ is hydrogen or methyl;
R₃ is hydrogen;
R₄ is hydrogen; and
R₆ is hydrogen.

In embodiments, the compound has a structure according to formula D-1:

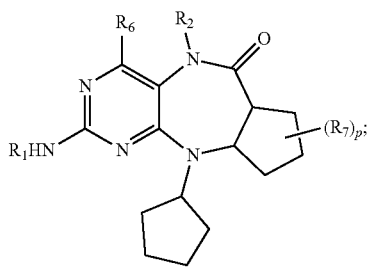

(D-1)

or a pharmaceutically acceptable salt, ester or prodrug thereof,
wherein,
R₁ is alkyl, aryl, heteroaryl, heterocyclic, or carbocyclic, wherein R₁ may be optionally substituted;
R₂ is hydrogen or optionally substituted alkyl;
R₆ is hydrogen or optionally substituted alkyl;
each R₇ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and
p is 0-6.

In embodiments, the compound has a structure according to formula E-1:

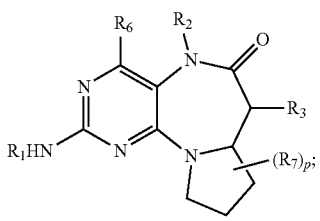

(E-1)

or a pharmaceutically acceptable salt, ester or prodrug thereof,
wherein,
R₁ is alkyl, aryl, heteroaryl, heterocyclic, or carbocyclic, wherein R₁ may be optionally substituted;
R₂ is hydrogen or optionally substituted alkyl;
R₃ is hydrogen or optionally substituted alkyl;
R₆ is hydrogen or optionally substituted alkyl;
each R₇ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and
p is 0-6.

In embodiments, the compound has a structure according to formula F-I:

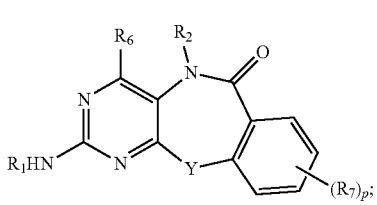

(F-I)

or a pharmaceutically acceptable salt, ester or prodrug thereof,
wherein,
Y is S, SO, SO₂, N, or O;
R₁ is alkyl, aryl, heteroaryl, heterocyclic, or carbocyclic, wherein R₁ may be optionally substituted;
R₂ is hydrogen or optionally substituted alkyl;
R₆ is hydrogen or optionally substituted alkyl;
each R₇ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and
p is 0-4.

In embodiments, the compound has a structure according to formula G-1:

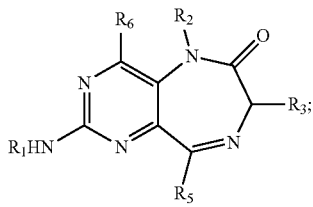

(G-1)

or a pharmaceutically acceptable salt, ester or prodrug thereof,
wherein,
$R_1$ is alkyl, alkenyl, alkynyl, each containing 0, 1, 2, or 3 heteroatoms selected from O, S, or N; or $R_1$ is aryl, arylalkyl, heteroaryl, heterocyclic, or carbocyclic, wherein $R_1$ may be optionally substituted;
$R_2$ is hydrogen or optionally substituted alkyl;
$R_3$ is hydrogen, alkyl, alkenyl, aryl, arylalkyl, heteroaryl, heterocyclic, or carbocyclic, each of which may be optionally substituted;
$R_5$ is hydrogen, alkyl, alkenyl, aryl, arylalkyl, heteroaryl, heterocyclic, or carbocyclic, each of which may be optionally substituted; and
$R_6$ is hydrogen or optionally substituted alkyl.

In one aspect, the method of treating a disease in a subject mediated by doublecortin-like kinase (DCLK1) and/or doublecortin-like kinase 2 (DCLK2) comprises administering to the subject a compound of formula I-2:

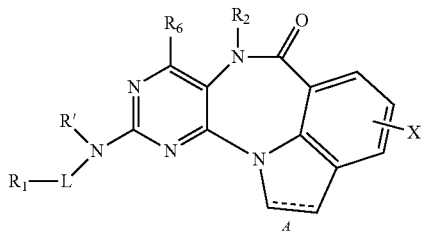

(I-2)

or a pharmaceutically acceptable salt, ester or prodrug thereof,
wherein,
A is a single bond or double bond;
R' is H or alkyl;
L is absent, S, SO, $SO_2$, or CO;
X is an optional substituent;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;
$R_2$ is hydrogen, optionally substituted alkyl, optionally substituted cycloalkyl, and optionally substituted heterocyclyl; and
$R_6$ is hydrogen or optionally substituted alkyl.

In another aspect, the method for reducing doublecortin-like kinase (DCLK1/2)-dependent cell growth comprising contacting a cell with a compound of formula I-2, or a pharmaceutically acceptable salt, ester or prodrug thereof.

In another aspect, the method of inhibiting doublecortin-like kinase (DCLK1/2) in a subject identified as in need of such treatment, comprising administering a compound of formula I-2, or a pharmaceutically acceptable salt, ester or prodrug thereof.

In one aspect, the method of treating a disease in a subject mediated by doublecortin-like kinase (DCLK1) and/or doublecortin-like kinase 2 (DCLK2) comprises comprising administering to the subject a compound of formula II-2:

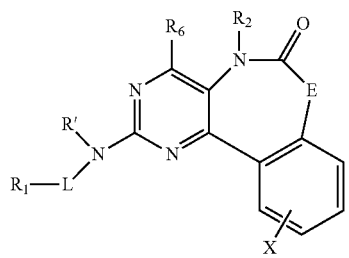

(II-2)

or a pharmaceutically acceptable salt, ester or prodrug thereof,
wherein,
R' is H or alkyl;
L is absent, S, SO, $SO_2$, or CO;
X is an optional substituent as defined for formula I;
E is $NR_2$ or $CHR_2$;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;
$R_2$ is, independently for each occurrence, hydrogen, optionally substituted alkyl, optionally substituted cycloalkyl, and optionally substituted heterocyclyl; and
$R_6$ is hydrogen or optionally substituted alkyl.

In another aspect, the method for reducing doublecortin-like kinase (DCLK1/2)-dependent cell growth comprising contacting a cell with a compound of formula II-2, or a pharmaceutically acceptable salt, ester or prodrug thereof.

In another aspect, the method of inhibiting doublecortin-like kinase (DCLK1/2) in a subject identified as in need of such treatment, comprising administering a compound of formula II-2, or a pharmaceutically acceptable salt, ester or prodrug thereof.

In one aspect, the method of treating a disease in a subject wherein the disease is mediated by doublecortin-like kinase (DCLK1) and/or doublecortin-like kinase 2 (DCLK2), the method comprising administering to the subject a compound of formula III-2:

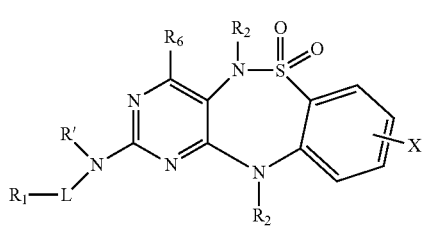

(III-2)

or a pharmaceutically acceptable salt, ester or prodrug thereof,
wherein,
R' is H or alkyl;
L is absent, S, SO, $SO_2$, or CO;
X is an optional substituent as defined for formula I;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein R₁ may be optionally substituted;

R₂ is, independently for each occurrence, hydrogen, optionally substituted alkyl, optionally substituted cycloalkyl, and optionally substituted heterocyclyl; and R₆ is hydrogen or optionally substituted alkyl.

In another aspect, the method for reducing doublecortin-like kinase (DCLK1/2)-dependent cell growth comprising contacting a cell with a compound of formula III-2, or a pharmaceutically acceptable salt, ester or prodrug thereof.

In another aspect, the method of inhibiting doublecortin-like kinase (DCLK1/2) in a subject identified as in need of such treatment, comprising administering a compound of formula III-2, or a pharmaceutically acceptable salt, ester or prodrug thereof.

In one aspect, the method of treating a disease in a subject wherein the disease is mediated by doublecortin-like kinase (DCLK1) and/or doublecortin-like kinase 2 (DCLK2), the method comprising administering to the subject a compound of formula IV-2:

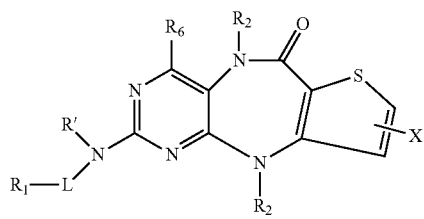

(IV-2)

or a pharmaceutically acceptable salt, ester or prodrug thereof, wherein,

R' is H or alkyl;

L is absent, S, SO, SO₂, or CO;

X is an optional substituent as defined for formula I;

R₁ is H, alkyl, alkenyl, alkynyl, each containing 0, 1, 2, or 3 heteroatoms selected from O, S, or N; or R₁ is aryl, arylalkyl, heteroaryl, heterocyclic, or carbocyclic; wherein R₁ may be optionally substituted;

R₂ is, independently for each occurrence, hydrogen, optionally substituted alkyl, optionally substituted cycloalkyl, and optionally substituted heterocyclyl; and R₆ is hydrogen or optionally substituted alkyl.

In another aspect, the method for reducing doublecortin-like kinase (DCLK1/2)-dependent cell growth comprising contacting a cell with a compound of formula IV-2, or a pharmaceutically acceptable salt, ester or prodrug thereof.

In another aspect, the method of inhibiting doublecortin-like kinase (DCLK1/2) in a subject identified as in need of such treatment, comprising administering a compound of formula IV-2, or a pharmaceutically acceptable salt, ester or prodrug thereof.

In one aspect, method of treating a disease in a subject mediated by doublecortin-like kinase (DCLK1) and/or doublecortin-like kinase 2 (DCLK2), the method comprising administering to the subject a compound of formula V-2:

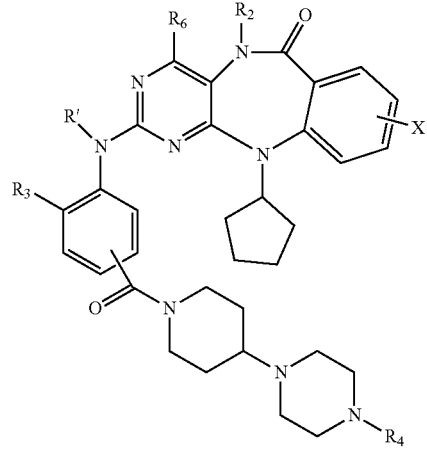

(V-2)

or a pharmaceutically acceptable salt, ester or prodrug thereof, wherein,

X is an optional substituent as defined for formula I;

R₂ is hydrogen or optionally substituted alkyl;

R₃ is —OH or —O-(optionally substituted alkyl);

R₄ is hydrogen or optionally substituted alkyl; and

R₆ is hydrogen or optionally substituted alkyl.

In another aspect, the method for reducing doublecortin-like kinase (DCLK1/2)-dependent cell growth comprising contacting a cell with a compound of formula V-2, or a pharmaceutically acceptable salt, ester or prodrug thereof.

In another aspect, the method of inhibiting doublecortin-like kinase (DCLK1/2) in a subject identified as in need of such treatment, comprising administering a compound of formula V-2, or a pharmaceutically acceptable salt, ester or prodrug thereof.

In one aspect, the method of treating a disease in a subject mediated by doublecortin-like kinase (DCLK1) and/or doublecortin-like kinase 2 (DCLK2), the method comprising administering to the subject a compound of formula VI-2:

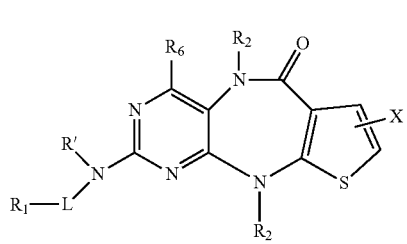

(VI-2)

or a pharmaceutically acceptable salt, ester or prodrug thereof, wherein,

R' is H or alkyl;

L is absent, S, SO, SO₂, or CO;

X is an optional substituent as defined for formula I;

R₁ is H, alkyl, alkenyl, alkynyl, each containing 0, 1, 2, or 3 heteroatoms selected from O, S, or N; or R₁ is aryl, arylalkyl, heteroaryl, heterocyclic, or carbocyclic; wherein R₁ may be optionally substituted;

R₂ is, independently for each occurrence, hydrogen, optionally substituted alkyl, optionally substituted cycloalkyl, and optionally substituted heterocyclyl; or two X moieties on adjacent atoms of the thiophene ring can form, together with the atoms to which they are attached, a phenyl ring; and R$_6$ is hydrogen or optionally substituted alkyl.

In another aspect, the method for reducing doublecortin-like kinase (DCLK1/2)-dependent cell growth comprising contacting a cell with a compound of formula VI-2, or a pharmaceutically acceptable salt, ester or prodrug thereof.

In another aspect, the method of inhibiting doublecortin-like kinase (DCLK1/2) in a subject identified as in need of such treatment, comprising administering a compound of formula VI-2, or a pharmaceutically acceptable salt, ester or prodrug thereof.

In one aspect, the method of treating a disease in a subject wherein the disease is mediated by doublecortin-like kinase (DCLK1) and/or doublecortin-like kinase 2 (DCLK2), the method comprising administering to the subject a compound of formula VII-2:

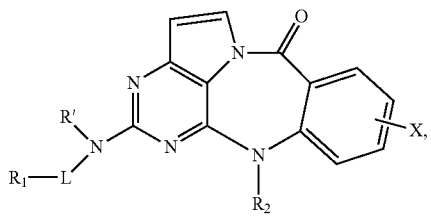

(VII-2)

or a pharmaceutically acceptable salt, ester or prodrug thereof,
wherein,
R' is H or alkyl;
L is absent, S, SO, SO$_2$, or CO;
X is an optional substituent as defined for formula I;
R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;
R$_2$ is hydrogen, optionally substituted alkyl, optionally substituted cycloalkyl, and optionally substituted heterocyclyl; and
R$_6$ is hydrogen or optionally substituted alkyl.

In another aspect, the method for reducing doublecortin-like kinase (DCLK1/2)-dependent cell growth comprising contacting a cell with a compound of formula VII-2, or a pharmaceutically acceptable salt, ester or prodrug thereof.

In another aspect, the method of inhibiting doublecortin-like kinase (DCLK1/2) in a subject identified as in need of such treatment, comprising administering a compound of formula VII-2, or a pharmaceutically acceptable salt, ester or prodrug thereof.

In one aspect, the method of treating a disease in a subject mediated by doublecortin-like kinase (DCLK1) and/or doublecortin-like kinase 2 (DCLK2), the method comprising administering to the subject a compound of formula VIII-2:

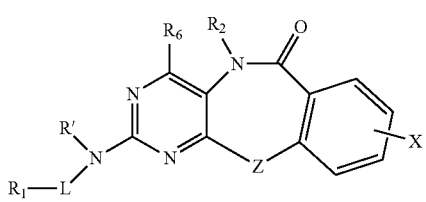

(VIII-2)

or a pharmaceutically acceptable salt, ester or prodrug thereof,
wherein,
R' is H or alkyl;
L is absent, S, SO, SO$_2$, or CO;
X is an optional substituent as defined for formula I;
Z is O or S;
R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;
R$_2$ is hydrogen, optionally substituted alkyl, optionally substituted cycloalkyl, and optionally substituted heterocyclyl; and
R$_6$ is hydrogen or optionally substituted alkyl.

In another aspect, the method for reducing doublecortin-like kinase (DCLK1/2)-dependent cell growth comprising contacting a cell with a compound of formula VIII-2, or a pharmaceutically acceptable salt, ester or prodrug thereof.

In another aspect, the method of inhibiting doublecortin-like kinase (DCLK1/2) in a subject identified as in need of such treatment, comprising administering a compound of formula VIII-2, or a pharmaceutically acceptable salt, ester or prodrug thereof.

In one aspect, the method of treating a disease in a subject mediated by doublecortin-like kinase (DCLK1) and/or doublecortin-like kinase 2 (DCLK2), the method comprising administering to the subject a compound of formula IX-2:

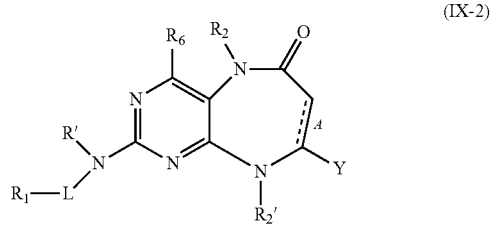

(IX-2)

or a pharmaceutically acceptable salt, ester or prodrug thereof,
wherein,
A is a single bond or double bond;
R' is H or alkyl;
L is absent, S, SO, SO$_2$, or CO;
Y is hydrogen, optionally substituted alkyl, optionally substituted cycloalkyl, and optionally substituted heterocyclyl;
R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;
R$_2$ and R$_2$' are each independently hydrogen, optionally substituted alkyl, optionally substituted cycloalkyl, and optionally substituted heterocyclyl;
or Y and R$_2$' can form, together with the atoms to which they are attached, a five-membered ring; and
R$_6$ is hydrogen or optionally substituted alkyl.

In another aspect, the method for reducing doublecortin-like kinase (DCLK1/2)-dependent cell growth comprising contacting a cell with a compound of formula IX-2, or a pharmaceutically acceptable salt, ester or prodrug thereof.

In another aspect, the method of inhibiting doublecortin-like kinase (DCLK1/2) in a subject identified as in need of such treatment, comprising administering a compound of formula IX-2, or a pharmaceutically acceptable salt, ester or prodrug thereof.

In one aspect, the present invention provides a compound of formula F-1:

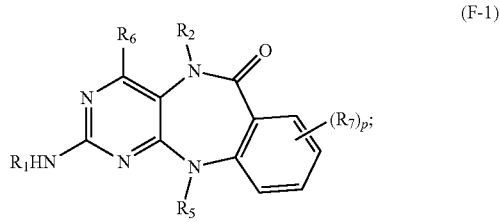

(F-1)

or a pharmaceutically acceptable salt, ester or prodrug thereof,
wherein,
$R_1$ is alkyl, aryl, heteroaryl, heterocyclic, or carbocyclic, wherein $R_1$ may be optionally substituted;
$R_2$ is hydrogen or optionally substituted alkyl;
$R_5$ is hydrogen, optionally substituted alkyl, optionally substituted aralkyl, or optionally substituted carbocyclic; and
$R_6$ is hydrogen or optionally substituted alkyl;
each $R_7$ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and
p is 0-4.

In embodiments, $R_5$ is methyl.
In embodiments, $R_2$ is unsubstituted alkyl.
In some embodiments, $R_2$ is methyl, ethyl, propyl, or iso-propyl, each of which may be optionally substituted with one or more halogen.
In some embodiments, $R_2$ is —CH$_2$—CH$_2$F, —CH$_2$—CHF$_2$, or —CH$_2$—CF$_3$.
In embodiments, the compound is of formula F-1-a:

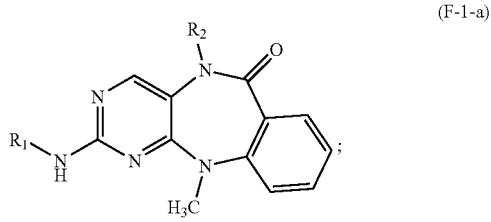

(F-1-a)

or a pharmaceutically acceptable salt, ester or prodrug thereof.

In embodiments, $R_2$ is unsubstituted alkyl.
In some embodiments, $R_2$ is methyl, ethyl, propyl, or iso-propyl, each of which may be optionally substituted with one or more halogen.
In some embodiments, $R_2$ is —CH$_2$—CH$_2$F, —CH$_2$—CHF$_2$, or —CH$_2$—CF$_3$.
In embodiments, $R_1$ is methyl, ethyl, propyl, iso-propyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In some embodiments, $R_1$ is phenyl or pyridyl, each of which may be optionally substituted.
In some embodiments, $R_1$ is substituted with 0-4 substituents, selected from halo, nitro, cyano, hydroxyl, amino, NH($R_A$), N($R_A$)($R_A$), CO$_2$H, C(O)$R_A$, C(O)O$R_A$, C(O)NH$_2$, C(O)NH($R_A$), C(O)N($R_A$)($R_A$), alkyl, aryl, arylalkyl, alkoxy, heteroaryl, heterocyclic, and carbocyclic, each of which may be further substituted;
wherein each $R_A$ is independently selected from alkyl, alkenyl, carbocyclic, aryl, heteroaryl, and heterocyclic, or two $R_A$ on the same atom combine to form a heterocyclic, each of which may be further substituted.
In some embodiments, $R_1$ is substituted with 0-4 substituents, selected from alkoxy, CO$_2$Me,

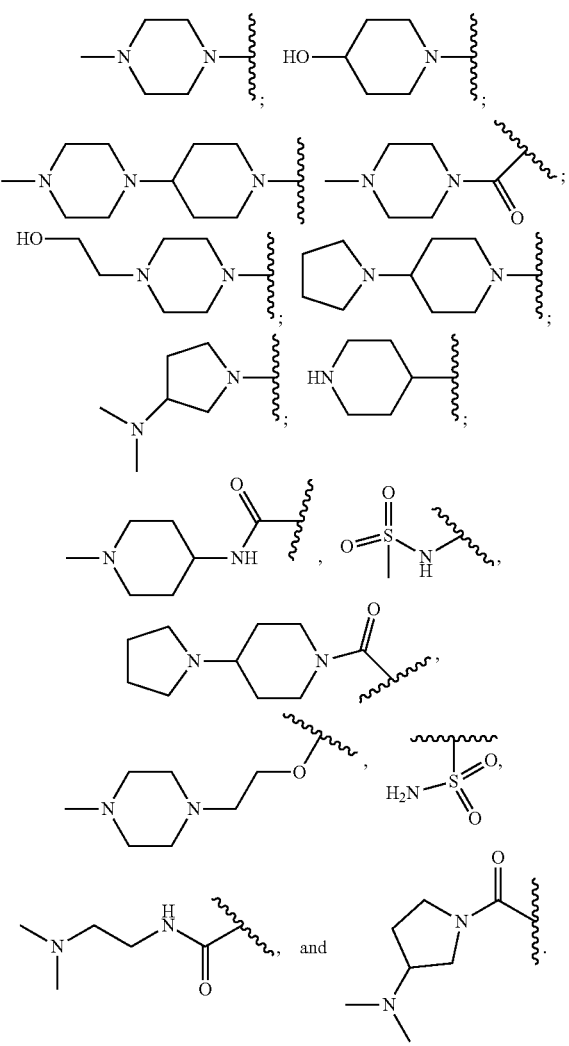

In embodiments, $R_1$ is phenyl, pyridyl, pyrimidinyl, furyl, pyrrolyl, pyrazolyl, imidazolyl, thienyl, or bicyclo[1.1.1]pent-1-yl, each of which may be optionally substituted.
In some embodiments, $R_1$ is substituted with 0-4 substituents, selected from halo, nitro, cyano, hydroxyl, amino, NH($R_A$), N($R_A$)($R_A$), CO$_2$H, C(O)$R_A$, C(O)O$R_A$, C(O)NH$_2$, C(O)NH($R_A$), C(O)N($R_A$)($R_A$), alkyl, aryl, arylalkyl, alkoxy, heteroaryl, heterocyclic, carbocyclic, SO$_2$($R_A$), SO$_3$ ($R_A$), SO$_2$N($R_A$) ($R_A$), SO$_2$NH($R_A$), SO$_2$NH$_2$, PO(O$R_A$)(O$R_A$), or PO(O$R_A$)($R_A$), each of which may be further substituted; and wherein each $R_4$ is independently selected from alkyl, alkenyl, carbocyclic, aryl, heteroaryl, and heterocyclic, or two $R_4$ on the same atom combine to form a heterocyclic, each of which may be further substituted.

In some embodiments, $R_1$ is selected from the group consisting of:

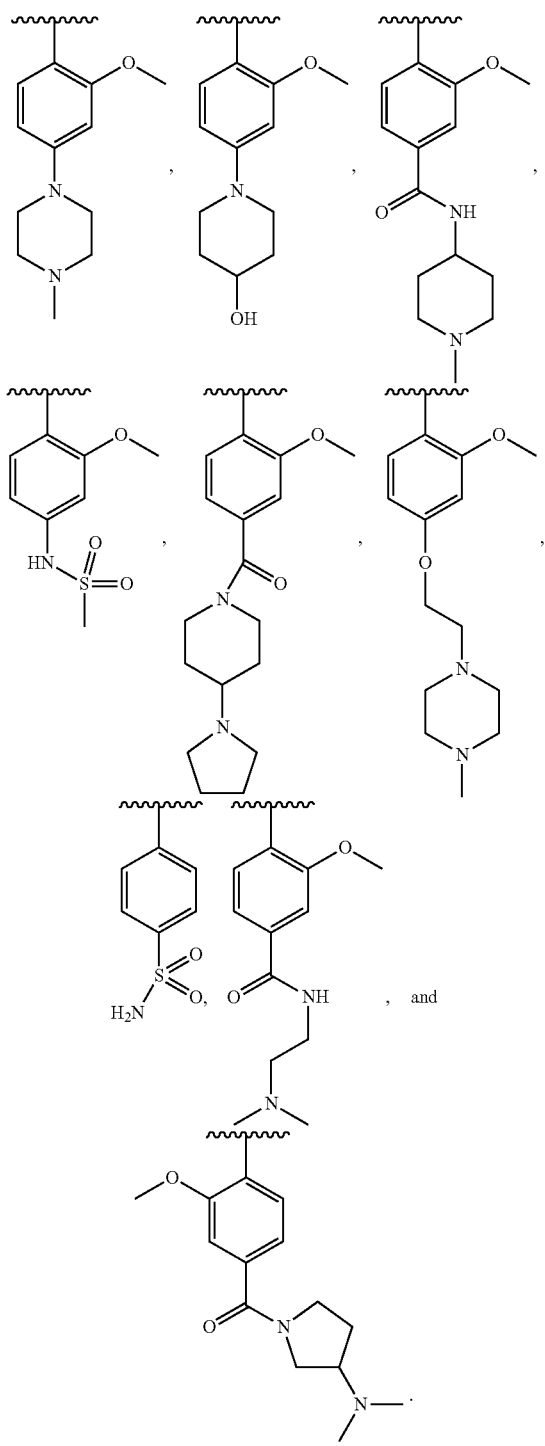

In embodiments, the compound of formula F-1-a inhibits DCLK1 and/or DCLK2.

Further provided in the present invention is a pharmaceutical composition comprising the compound (e.g. formula F-1, formula F-1-a, formula A-1 and etc.) as described herein, or a pharmaceutically acceptable salt, ester or prodrug thereof.

Additionally, in one aspect, the intention provides methods of treating a disease in a subject, wherein the disease is mediated by doublecortin-like kinase (DCLK1) and/or doublecortin-like kinase 2 (DCLK2), the method comprising administering to the subject the compound as described herein, or a pharmaceutically acceptable salt, ester or prodrug thereof.

In another aspect, the invention provides methods for reducing doublecortin-like kinase (DCLK1/2)-dependent cell growth comprising contacting a cell with the compound as described herein, or a pharmaceutically acceptable salt, ester or prodrug thereof.

In another aspect, the invention provides methods of inhibiting doublecortin-like kinase (DCLK1/2) in a subject identified as in need of such treatment, comprising administering the compound as described herein, or a pharmaceutically acceptable salt, ester or prodrug thereof.

In one aspect, the invention features a method of treating a disease in a subject mediated by a kinase that is doublecortin-like kinase (DCLK1/2) comprising administering to the subject a compound as described herein (e.g., a compound of formula F-1, formula F-1-a or formula A-1), or a pharmaceutically acceptable salt, ester or prodrug thereof.

In another aspect, the invention features a method for reducing doublecortin-like kinase (DCLK1/2)-dependent cell growth comprising contacting a cell with a compound as described herein (e.g., a compound of formula F-1, formula F-1-a or formula A-1) or a pharmaceutically acceptable salt, ester or prodrug thereof.

In another aspect, the invention features a method of inhibiting doublecortin-like kinase (DCLK1/2) in a subject identified as in need of such treatment, comprising administering a compound as described (e.g., a compound of formula F-1, formula F-1-a or formula A-1), or a pharmaceutically acceptable salt, ester or prodrug thereof.

In another aspect, the invention provides a method for reducing kinase-dependent cell growth comprising contacting a cell with a kinase inhibitor compound as described herein or a pharmaceutically acceptable ester, salt, or prodrug thereof.

In other aspects, the invention provides a method of inhibiting kinase in a subject identified as in need of such treatment, comprising administering a kinase inhibitor compound as described herein, or a pharmaceutically acceptable ester, salt, or prodrug thereof.

In one aspect, the invention provides a kit comprising a compound capable of inhibiting kinase activity selected from one or more kinase inhibitor compounds described herein, or a pharmaceutically acceptable ester, salt, or prodrug thereof, and instructions for use in treating cancer.

In one aspect, the invention provides a pharmaceutical composition comprising a kinase inhibitor compound as described herein, or a pharmaceutically acceptable ester, salt, or prodrug thereof, together with a pharmaceutically acceptable carrier.

In one aspect, the invention provides a method of synthesizing a kinase inhibitor compound as described herein.

DETAILED DESCRIPTION OF THE INVENTION

Definitions

Figure 1:
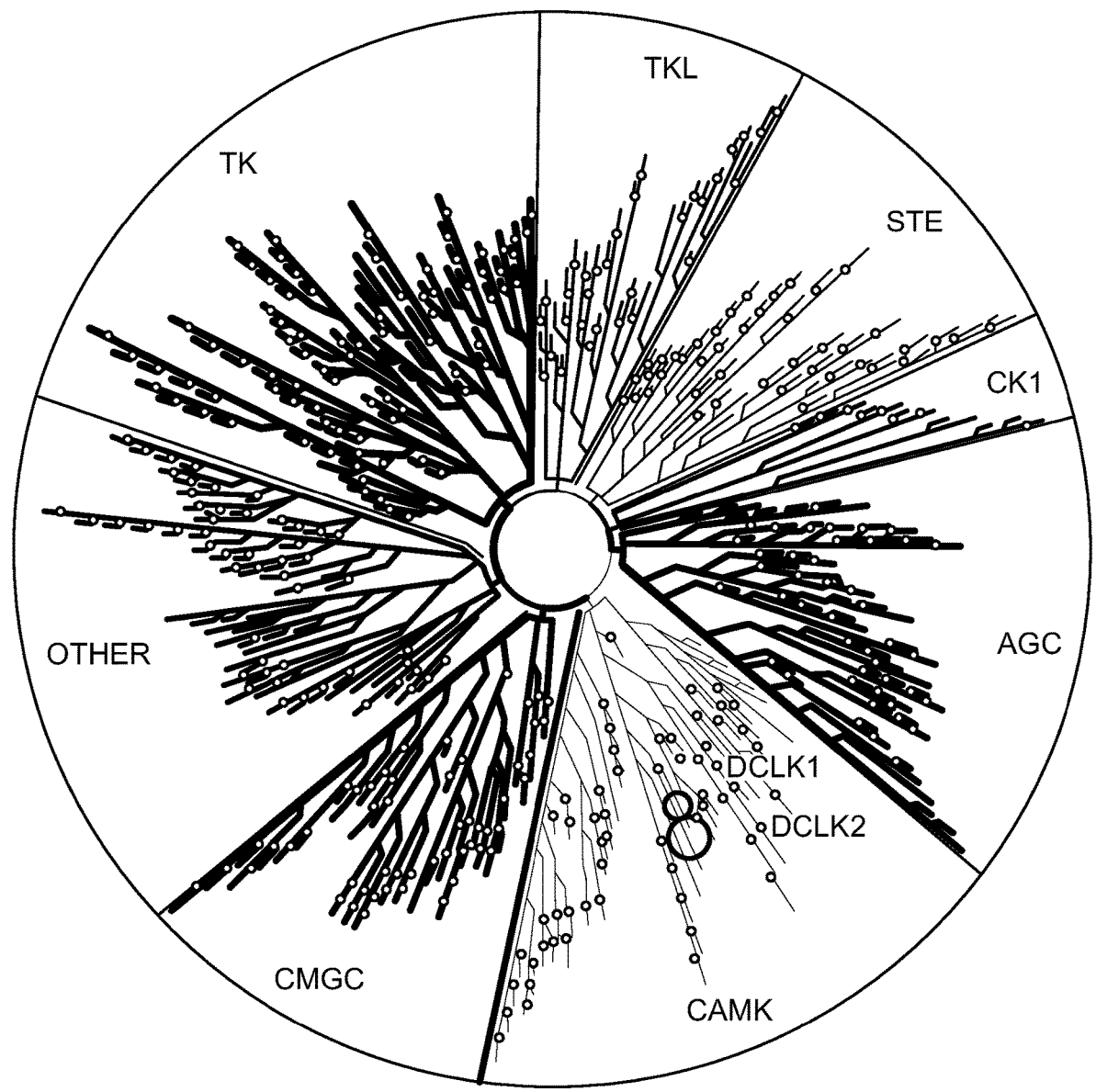
FIG. 1 illustrates selectivity data generated using KINOMEscan® platform for Compound 2 at 1 uM concentration and this image was generated using TREEspot™ Software Tool.
Figure 1:
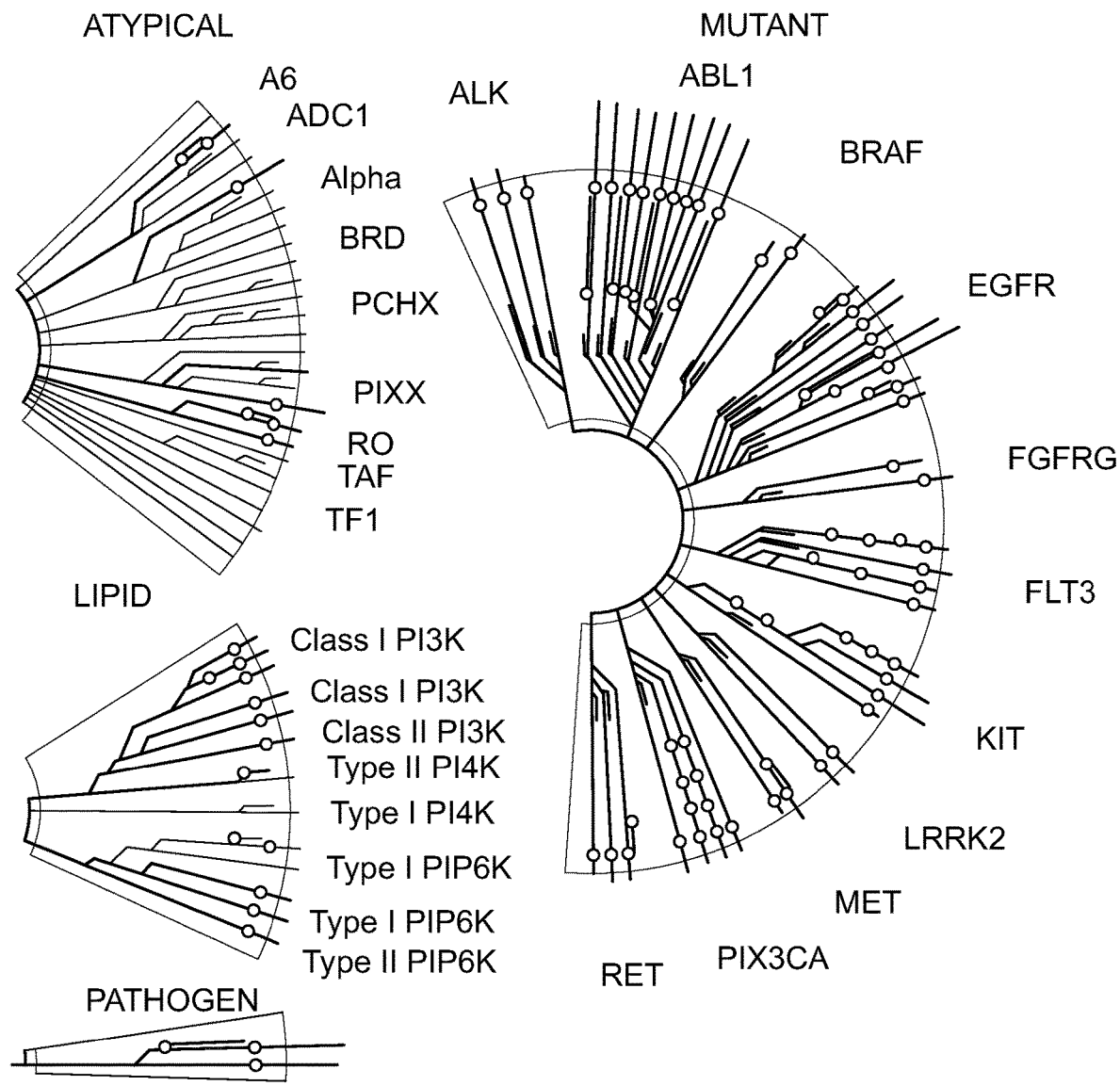

Listed below are definitions of various terms used to describe this invention. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl radical.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated are a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl) where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like. In accordance with the invention, any of the aryls, substituted aryls, heteroaryls and substituted heteroaryls described herein, can be any aromatic group. Aromatic groups can be substituted or unsubstituted.

The terms "halo" and "halogen," as used herein, refer to an atom selected from fluorine, chlorine, bromine and iodine.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I,

—OH, protected hydroxy,

—NO$_2$, —CN,

—NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)— C$_1$-C$_{12}$-alkyl, —C(O)— C$_2$-C$_{12}$-alkenyl, —C(O)— C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH— heterocycloalkyl, —OCO$_2$— C$_1$-C$_{12}$-alkyl, —OCO$_2$— C$_2$-C$_{12}$-alkenyl, —OCO$_2$— C$_2$-C$_{12}$-alkenyl, —OCO$_2$—C$_3$-C$_{12}$-cycloalkyl, —OCO$_2$-aryl, —OCO2-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH— aryl, —OCONH-heteroaryl, —OCONH-heterocycloalkyl, —NHC(O)— C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)— heterocycloalkyl, —NHCO$_2$— C$_1$-C$_{12}$-alkyl, —NHCO$_2$— C$_2$-C$_{12}$-alkenyl, —NHCO$_2$— C$_2$-C$_{12}$-alkenyl, —NHCO$_2$— C$_3$-C$_{12}$-cycloalkyl, —NHCO$_2$— aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH— heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)— heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

It is understood that the aryls, heteroaryls, alkyls, and the like can be further substituted.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; Adrenal glands: neuroblastoma, and blood-borne cancers such as chronic lymphocytic leukemia (CLL), follicular lymphoma (FL) and indolent non-Hodgkin's lymphoma (iNHL).

Thus, the term "cancerous cell" as provided herein, includes a cell afflicted by any one of the above-identified conditions.

The term "liver disease" is damage to or disease of the liver that can lead to failure of liver functions. The term "liver disease" includes, but is not limited to, the following diseases: hepatitis, alcoholic liver disease, hereditary diseases such as hemochromatosis and Wilson's disease, a fatty liver disease, non-alcoholic fatty liver disease (NAFLD), non-alcoholic steatohepatitis (NASH), cirrhosis, primary biliary cirrhosis, primary sclerosing cholangitis, Budd-Chiari syndrome, fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Wolmans disease, acute fatty liver of pregnancy, Weber-Christian disease, Gilber's syndrome, Wolmans disease, acute fatty liver of pregnancy, or lipodystrophy.

In embodiments, the disease is a neurodegenerative disease.

In some embodiments, the disease is Alzheimer's disease (AD), Parkinson's disease (PD), Huntington's (HD) diseases, amyotrophic lateral sclerosis (ALS), spinal muscular atrophy (SMA), schizophrenia, attention-deficit/hyperactivity disorder (ADHD), fetal alcohol syndrome and diabetic encephalopathy.

The term "Kinase Panel" is a list of kinases including, but not limited to, MPS1 (TTK), ERK5 (BMK1, MAPK7), polo kinase 1,2,3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB, TrkC, AAK1, ABL1, ABL1(E255K), ABL1(F317I), ABL1(F317L), ABL1 (H396P), ABL1(M351T), ABL1(Q252H), ABL1(T315I), ABL1(Y253F), ABL2, ACVR1, ACVR1B, ACVR2A, ACVR2B, ACVRL1, ADCK3, ADCK4, AKT1, AKT2, AKT3, ALK, AMPK-alpha1, AMPK-alpha2, ANKK1, ARK5, ASK1, ASK2, AURKA, AURKB, AURKC, AXL, BIKE, BLK, BMPR1A, BMPR1B, BMPR2, BMX, BRAF, BRAF(V600E), BRK, BRSK1, BRSK2, BTK, CAMK1, CAMK1D, CAMK1G, CAMK2A, CAMK2D, CAMK2G, CAMK4, CAMKK1, CAMKK2, $CDC_2L1$, $CDC_2L2$, CDK11, CDK2, CDK3, CDK5, CDK7, CDK8, CDK9, CDKL2, CDKL3, CDKL5, CHECK1, CHEK2, CIT, CLK1, CLK2, CLK3, CLK4, CSF1R, CSK, CSNK1A1L, CSNK1D, CSNK1E, CSNK1G1, CSNK1G3, CSNK2A1, CSNK2A2, CTK, DAPK1, DAPK2, DAPK3, DCAMKL1 (DLCK1), DCAMKL2 (DCLK2), DCAMKL3, DDR1, DDR2, DLK, DMPK, DMPK2, DRAK1, DRAK2, DYRK1A, DYRK1B, DYRK2, EGFR, EGFR (E746-A750DEL), EGFR (G719C), EGFR (G719S), EGFR(L747-E749del, A750P), EGFR(L747-S752del, P753S), EGFR (L747-T751del,Sins), EGFR(L858R), EGFR(L858R, T790M), EGFR(L861Q), EGFR(S752-1759del), EPHAL EPHA2, EPHA3, EPHA4, EPHA5, EPHA6, EPHA7, EPHA8, EPHB1, EPHB2, EPHB3, EPHB4, EPHB6, ERBB2, ERBB3, ERBB4, ERK1, ERK2, ERK3, ERK4, ERK5, ERK8, ERN1, FAK, FER, FES, FGFR1, FGFR2, FGFR3, FGFR3(G697C), FGFR4, FGR, FLT1, FLT3, FLT3 (D835H), FLT3(D835Y), FLT3(ITD), FLT3(K663Q), FLT3 (N841I), FLT4, FRK, FYN, GAK, GCN2(Kin.Dom.2, S808G), GRK1, GRK4, GRK7, GSK3A, GSK3B, HCK, HIPK1, HIPK2, HIPK3, HIPK4, HPK1, HUNK, ICK, IGF1R, IKK-ALPHA, IKK-BETA, IKK-EPSILON, INSR, INSRR, IRAK1, IRAK3, ITK, JAK1(JH1domain-catalytic), JAK1(JH2domain-pseudokinase), JAK2(JH1domain-catalytic), JAK3(JH1domain-catalytic), JNK1, JNK2, JNK3, KIT, KIT(D816V), KIT(L576P), KIT(V559D), KIT (V559D,T670I), KIT(V559D,V654A), LATS1, LATS2, LCK, LIMK1, LIMK2, LKB1, LOK, LTK, LYN, LZK, MAK, MAP3K1, MAP2K15, MAP3K2, MAP3K3, MAP3K4, MAP4K2, MAP4K3, MAP4K5, MAPKAPK2, MAPKAPK5, MARK1, MARK2, MARK3, MARK4, MAST1, MEK1, MEK2, MEK3, MEK4, MEK6, MELK, MERTK, MET, MET(M1250T), MET(Y1235D), MINK, MKNK1, MKNK2, MLCK, MLK1, MLK2, MLK3, MRCKA, MRCKB, MST1, MST1R, MST2, MST3, MST4, MUSK, MYLK, MYLK2, MYO3A, MYO3B, NDR1, NDR2, NEK1, NEK2, NEK5, NEK6, NEK7, NEK9, NIM1, NLK, OSR1, p38-alpha, p38-beta, p38-delta, p38-gamma, PAK1, PAK2, PAK3, PAK4, PAK6, PAK7, PCTK1, PCTK2, PCTK3, PDGFRA, PDGFRB, PDPK1, PFTAIRE2, PFTK1, PHKG1, PHKG2, PIK3C2B, PIK3C2G, PIK3CA, PIK3CA (C420R), PIK3CA(E542K), PIK3CA(E545A), PIK3CA (E545K), PIK3CA(H1047L), PIK3CA(H1047Y), PIK3CA (M1043I), PIK3CA(Q546K), PIK3CB, PIK3CD, PIK3CG, PIK4CB, PIM1, PIM2, PIM3, PIP5K1A, PIP5K2B, PKAC-ALPHA, PKAC-BETA, PKMYT1, PKN1, PKN2, PLK1, PLK2, PLK3, PLK4, PRKCD, PRKCE, PRKCH, PRKCQ, PRKD1, PRKD3, PRKG1, PRKG2, PRKR, PRKX, PRP4, PYK2, QSK, RAF1, RET, RET(M918T), RET(V804L), RET(V804M), RIOK1, RIOK2, RIOK3, RIPK1, RIPK2, RIPK4, ROCK1, ROCK2, ROS1, RPS6KA1(Kin.Dom.1-N-terminal), RPS6KA1(Kin.Dom.2-C-terminal), RPS6KA2 (Kin.Dom.1-N-terminal), RPS6KA2(Kin.Dom.2-C-terminal), RPS6KA3(Kin.Dom.1-N-terminal), RPS6KA4 (Kin.Dom.1-N-terminal), RPS6KA4(Kin.Dom.2-C-terminal), RPS6KA5(Kin.Dom.1-N-terminal), RPS6KA5 (Kin.Dom.2-C-terminal), RPS6KA6(Kin.Dom.1-N-terminal), RPS6KA6(Kin.Dom.2-C-terminal), SBK1, SgK085, SgK110, SIK, SIK2, SLK, SNARK, SRC, SRMS, SRPK1, SRPK2, SRPK3, STK16, STK33, STK39, SYK, TAK1, TAO1, TAOK2, TAOK3, TBK1, TEC, TESK1, TGFBR1, TGFBR2, TIE1, TIE2, TLK1, TLK2, TNIK, TNK1, TNK2, TNNI3K, TRKA, TRKB, TRKC, TSSK1B, TTK, TXK, TYK2(JH1domain-catalytic), TYK2 (JH2domain-pseudokinase), TYRO3, ULK1, ULK2, ULK3, VEGFR2, WEE1, WEE2, YANK2, YANK3, YES, YSK1, YSK4, ZAK and ZAP70. Compounds of the invention are screened against the kinase panel (wild type and/or mutation thereof) and inhibit the activity of at least one of said panel members.

Mutant forms of a kinase means single or multiple amino acid changes from the wild-type sequence.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating disorders through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Doublecortin-Like Kinases

Described herein are compounds that can inhibit at least one of doublecortin-like kinases (DCLK), e.g., isoforms such as DCLK1 and DCLK2, which are members of serine/threonine-protein kinase family and $Ca^{2+}$/calmodulin-dependent protein kinase class of enzymes.

These doublecortin-like kinases (DCLK) commonly contain i) two N-terminal doublecortin domains, which can bind or associate microtubules; ii) a C-terminal serine/threonine protein kinase domain, which shows substantial homology to $Ca^{2+}$/calmodulin-dependent protein kinase, and iii) a serine/proline-rich domain in between the doublecortin and the protein kinase domains, which mediates multiple protein-protein interactions.

Human serine/threonine-protein kinase doublecortin-like kinase 1 (DCLK1) refers to the protein products of the human gene DCLK1. This includes any serine/threonine-protein kinases (EC:2.7.11.1) referred to as, for example, doublecortin and CaM kinase-like 1(DCAMKL1), doublecortin domain-containing protein 3A($DCDC_3A$), CPG16 (candidate plasticity gene 16), CaMK-like CREB regulatory kinase 1 (CL1, CLICK-I, CLICK1, or CLIK1) and/or KIAA0369, proteins listed under UNIPROT ID: Q5VZY9 or uniprot ID: O15075, or homologous proteins or isoforms thereof, including but not limited to isoforms 1-4 (alternate nomenclature DCLK1-long, DCLK1-short).

Likewise, human serine/threonine-protein kinase doublecortin-like kinase 2 (DCLK2) refers to the protein products of the human gene DCLK2. This includes any serine/threonine-protein kinases (EC:2.7.11.1) which may be alternately named as, for example, CaMK-like CREB regulatory kinase 2 (CL2, CLICK-II, CLICK2, or CLIK2); doublecortin and CaM kinase-like 2 (DCAMKL2); doublecortin domain-containing protein 3B ($DCDC_3B$); doublecortin-like and CAM kinase-like 2 (DCLK2); doublecortin-like kinase 2 (DCK2); serine/threonine-protein kinase DCLK2 and proteins listed under UNIPROT ID: Q8N568, or homologous proteins or isoforms thereof. Isoforms include but are not limited to isoforms 1-3 listed in UNIPROT.

DCLK1 is a microtubule-associated protein that plays a key role in neuronal migration, retrograde transport, neuronal apoptosis, neurogenesis and synapse maturation by regulation of mitotic spindle formation, which can be independent from its protein kinase activity (Reiner, O. et al, *BMC Genomics* 2006, 7 (1), 1-16).

Moreover, DCLK1 is frequently mutated across many cancer types. In particular, DCLK1 can be a driver gene for gastic cancer and is listed among the top 15 presumed driver genes (The Cancer Genome Atlas Research, *Nature* 2014, 513 (7517), 202-209). Expression of DCLK1 is also associated with poor prognosis in gastric cancer patients (Győrffy, B. et al., *PLoS ONE* 2013, 8 (12)). Additionally, DCLK1 can be a marker of quiescent stem-cells in the stomach, intestine and pancreas, and those cells have been shown to function as the cancer stem cells which initiate and support cancers in the intestine and pancreas, alone, or when harboring oncogenic mutations, or upon loss of tumour suppressor genes. For instance, ablation of these cells induces rapid regression of tumors in murine models of intestinal cancer (Ito, H. et al., *PLoS ONE* 2016, 11 (1); Nakanishi, Y. et al., *Nature genetics* 2013, 45 (1), 98-103; Westphalen, C. B., et. al, *The Journal of clinical investigation* 2014, 124 (3), 1283-95; Westphalen, C. B. et al., *Cell Stem Cell* 18 (4), 441-455).

Accordingly, as described herein, DCLK1/2 positive cells and DCLK1/2 functions can be targeted as promising therapeutic strategies in cancer treatments (e.g. treatments for gastric, pancreatic and intestinal cancers).

However, currently available DCLK1/2 kinase inhibitors are highly multi-targeted and have been shown to inhibit a number of other kinases and bromodomains. Prior to the invention described herein, there were no potent or selective inhibitors of the DCLK1/2 kinases described in the literature.

Accordingly, described herein are series of compounds based around a pyrimido-diazepinone scaffold. Such compounds, including those based on a 2-amino-5,8,11-trimethyl-5,11-dihydro-6H-benzo[e]pyrimido[5,4-b][1,4]diazepin-6-one scaffold, can be potent and selective inhibitors of DCLK1 or DCLK2, or alternatively, selective dual inhibitors of DCLK1 and DCLK2, thereby providing a method of treating/preventing a related disease mediated by DCLK1 and/or DCLK2.

DCLK1/2 Inhibitor Compounds

Described herein are series of compounds based around a pyrimido-diazepinone scaffold. Such compounds can be inhibitors of kinases (e.g., DCLK, including DCLK isoforms such as DCLK1 and/or DCLK2) and are referred to herein as "DCLK1/2 inhibitor compounds."

In embodiments, the invention provides a compound of formula F-1:

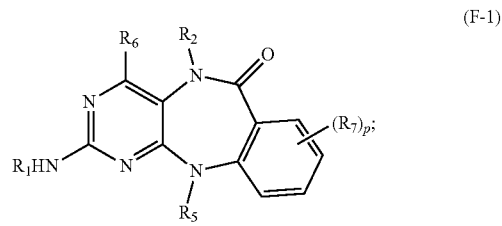

or a pharmaceutically acceptable salt, ester or prodrug thereof,
wherein,
$R_1$ is alkyl, aryl, heteroaryl, heterocyclic, or carbocyclic, wherein $R_1$ may be optionally substituted;
$R_2$ is hydrogen or optionally substituted alkyl;
$R_5$ is hydrogen, optionally substituted alkyl, optionally substituted aralkyl, or optionally substituted carbocyclic; and
$R_6$ is hydrogen or optionally substituted alkyl;
each $R_7$ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and
p is 0-4.

In embodiments, $R_5$ is methyl.
In embodiments, $R_2$ is unsubstituted alkyl.
In certain embodiments, $R_2$ is methyl, ethyl, propyl, or iso-propyl, each of which may be optionally substituted with one or more halogen.
In certain embodiments, $R_2$ is —$CH_2$—$CH_2F$, —$CH_2$—$CHF_2$, or —$CH_2$—$CF_3$.
In embodiments, p is 0; or when p is 1, $R_7$ is unsubstituted alkyl.
In certain embodiments, $R_1$ is methyl, ethyl, propyl, iso-propyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.
In a further embodiment, $R_1$ is phenyl or pyridyl, each of which may be optionally substituted.
In another embodiment, $R_1$ is substituted with 0-4 substituents, selected from halo, nitro, cyano, hydroxyl, amino, NH($R_A$), N($R_A$)($R_A$), $CO_2$H, C(O)$R_A$, C(O)O$R_A$, C(O)$NH_2$, C(O)NH($R_A$), C(O)N($R_A$)($R_A$), alkyl, aryl, arylalkyl, alkoxy, heteroaryl, heterocyclic, and carbocyclic, each of which may be further substituted; wherein each $R_A$ is independently selected from alkyl, alkenyl, carbocyclic, aryl, heteroaryl, and heterocyclic, or two $R_A$ on the same atom combine to form a heterocyclic, each of which may be further substituted.

In certain embodiments, $R_1$ is substituted with 0-4 substituents, selected from alkoxy, $CO_2$Me,

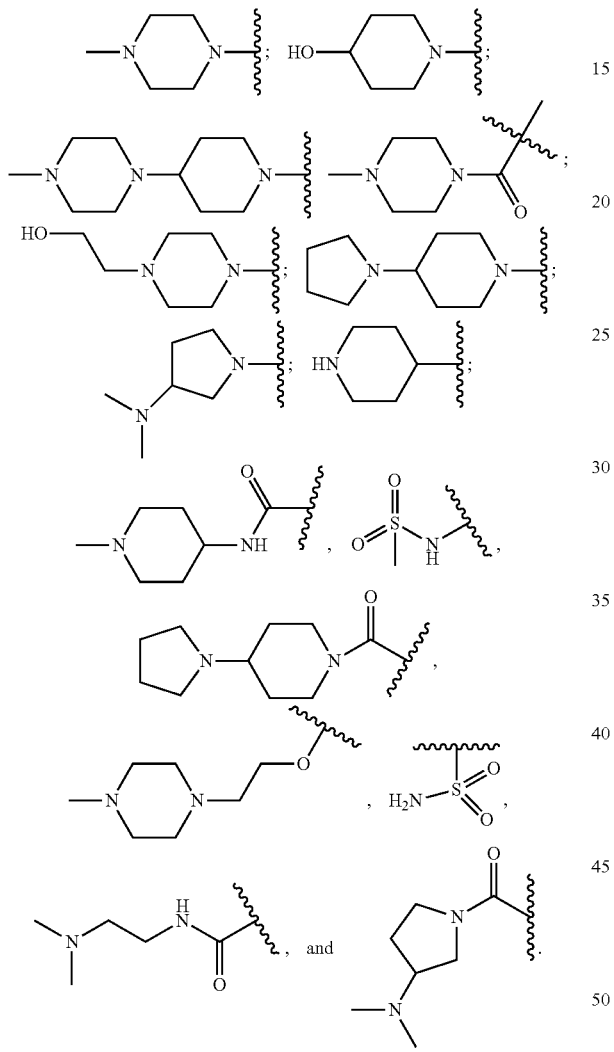

In embodiments, $R_1$ is phenyl, pyridyl, pyrimidinyl, furyl, pyrrolyl, pyrazolyl, imidazolyl, thienyl, or bicyclo[1.1.1]pent-1-yl, each of which may be optionally substituted.

In embodiments, $R_1$ is substituted with 0-4 substituents, selected from halo, nitro, cyano, hydroxyl, amino, NH($R_A$), N($R_A$)($R_A$), $CO_2$H, C(O)$R_A$, C(O)O$R_A$, C(O)$NH_2$, C(O)NH($R_A$), C(O)N($R_A$)($R_A$), alkyl, aryl, arylalkyl, alkoxy, heteroaryl, heterocyclic, carbocyclic, $SO_2$($R_A$), $SO_3$($R_A$), $SO_2$N($R_A$)($R_A$), $SO_2$NH($R_A$), $SO_2NH_2$, PO(O$R_A$)(O$R_A$), or PO(O$R_A$)($R_A$), each of which may be further substituted, and wherein each $R_A$ is independently selected from alkyl, alkenyl, carbocyclic, aryl, heteroaryl, and heterocyclic, or two $R_A$ on the same atom combine to form a heterocyclic, each of which may be further substituted.

In certain embodiments, $R_1$ is selected from the group consisting of

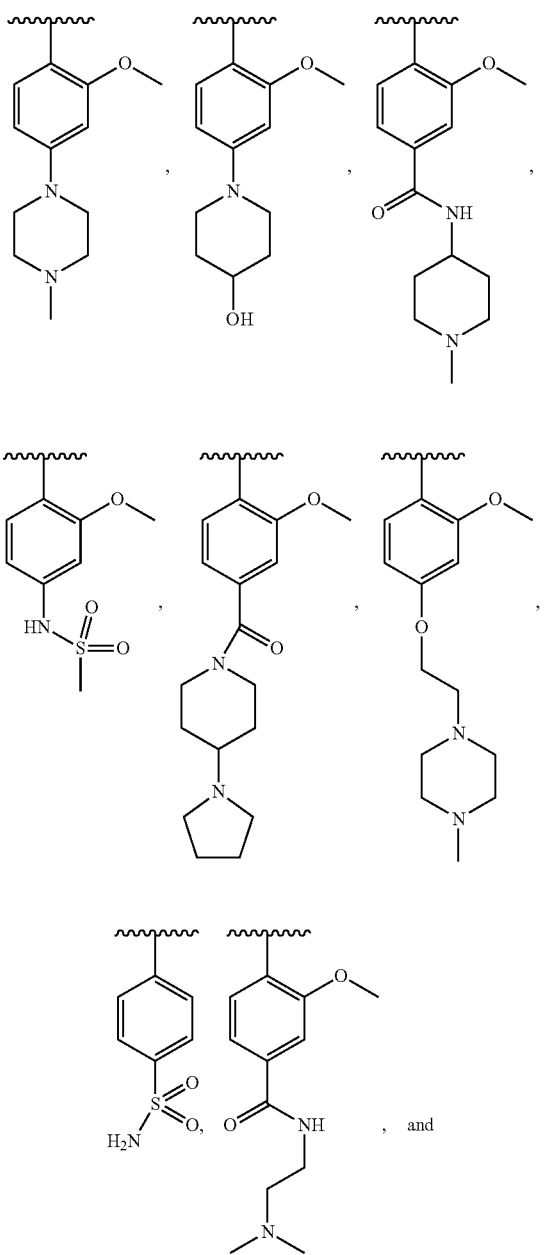

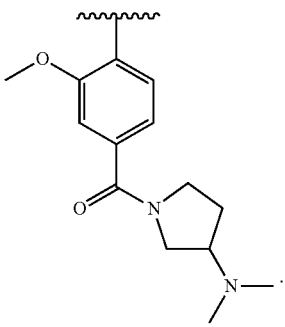

In embodiments, the compound is of formula F-1-a:

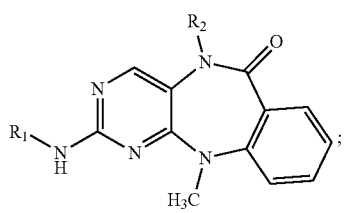

(F-1-a)

or a pharmaceutically acceptable salt, ester or prodrug thereof, wherein $R_1$ is alkyl, aryl, heteroaryl, heterocyclic, or carbocyclic, wherein $R_1$ may be optionally substituted.

In embodiments, $R_2$ is unsubstituted alkyl.

In certain embodiments, $R_2$ is methyl, ethyl, propyl, or iso-propyl, each of which may be optionally substituted with one or more halogen.

In certain embodiments, $R_2$ is —$CH_2$—$CH_2F$, —$CH_2$—$CHF_2$, or —$CH_2$—$CF_3$.

In certain embodiments, $R_1$ is methyl, ethyl, propyl, iso-propyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In a further embodiment, $R_1$ is phenyl or pyridyl, each of which may be optionally substituted.

In another embodiment, $R_1$ is substituted with 0-4 substituents, selected from halo, nitro, cyano, hydroxyl, amino, $NH(R_A)$, $N(R_A)(R_A)$, $CO_2H$, $C(O)R_A$, $C(O)OR_A$, $C(O)NH_2$, $C(O)NH(R_A)$, $C(O)N(R_A)(R_A)$, alkyl, aryl, arylalkyl, alkoxy, heteroaryl, heterocyclic, and carbocyclic, each of which may be further substituted; wherein each $R_A$ is independently selected from alkyl, alkenyl, carbocyclic, aryl, heteroaryl, and heterocyclic, or two $R_A$ on the same atom combine to form a heterocyclic, each of which may be further substituted.

In certain embodiments, $R_1$ is substituted with 0-4 substituents, selected from alkoxy, $CO_2Me$,

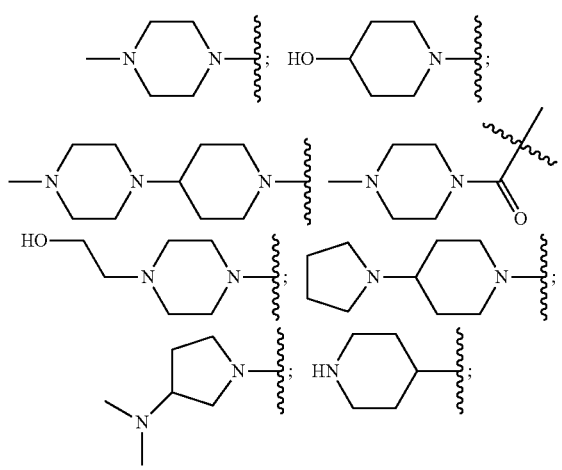

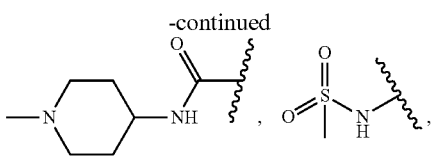

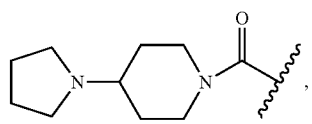

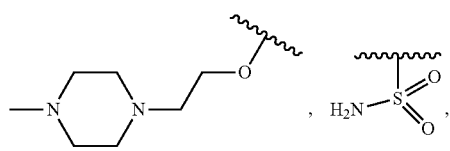

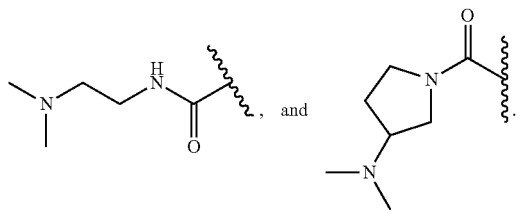

In embodiments, $R_1$ is phenyl, pyridyl, pyrimidinyl, furyl, pyrrolyl, pyrazolyl, imidazolyl, thienyl, or bicyclo[1.1.1]pent-1-yl, each of which may be optionally substituted.

In embodiments, $R_1$ is substituted with 0-4 substituents, selected from halo, nitro, cyano, hydroxyl, amino, $NH(R_A)$, $N(R_A)(R_A)$, $CO_2H$, $C(O)R_A$, $C(O)OR_A$, $C(O)NH_2$, $C(O)NH(R_A)$, $C(O)N(R_A)(R_A)$, alkyl, aryl, arylalkyl, alkoxy, heteroaryl, heterocyclic, carbocyclic, $SO_2(R_A)$, $SO_3(R_A)$, $SO_2N(R_A)(R_A)$, $SO_2NH(R_A)$, $SO_2NH_2$, $PO(OR_A)(OR_A)$, or $PO(OR_A)(R_A)$, each of which may be further substituted, and wherein each $R_A$ is independently selected from alkyl, alkenyl, carbocyclic, aryl, heteroaryl, and heterocyclic, or two $R_A$ on the same atom combine to form a heterocyclic, each of which may be further substituted.

In embodiments, $R_1$ is selected from the group consisting of

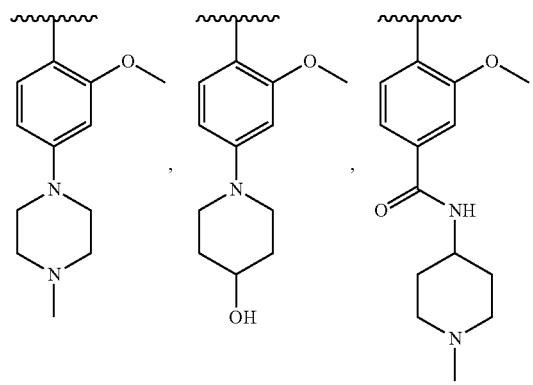

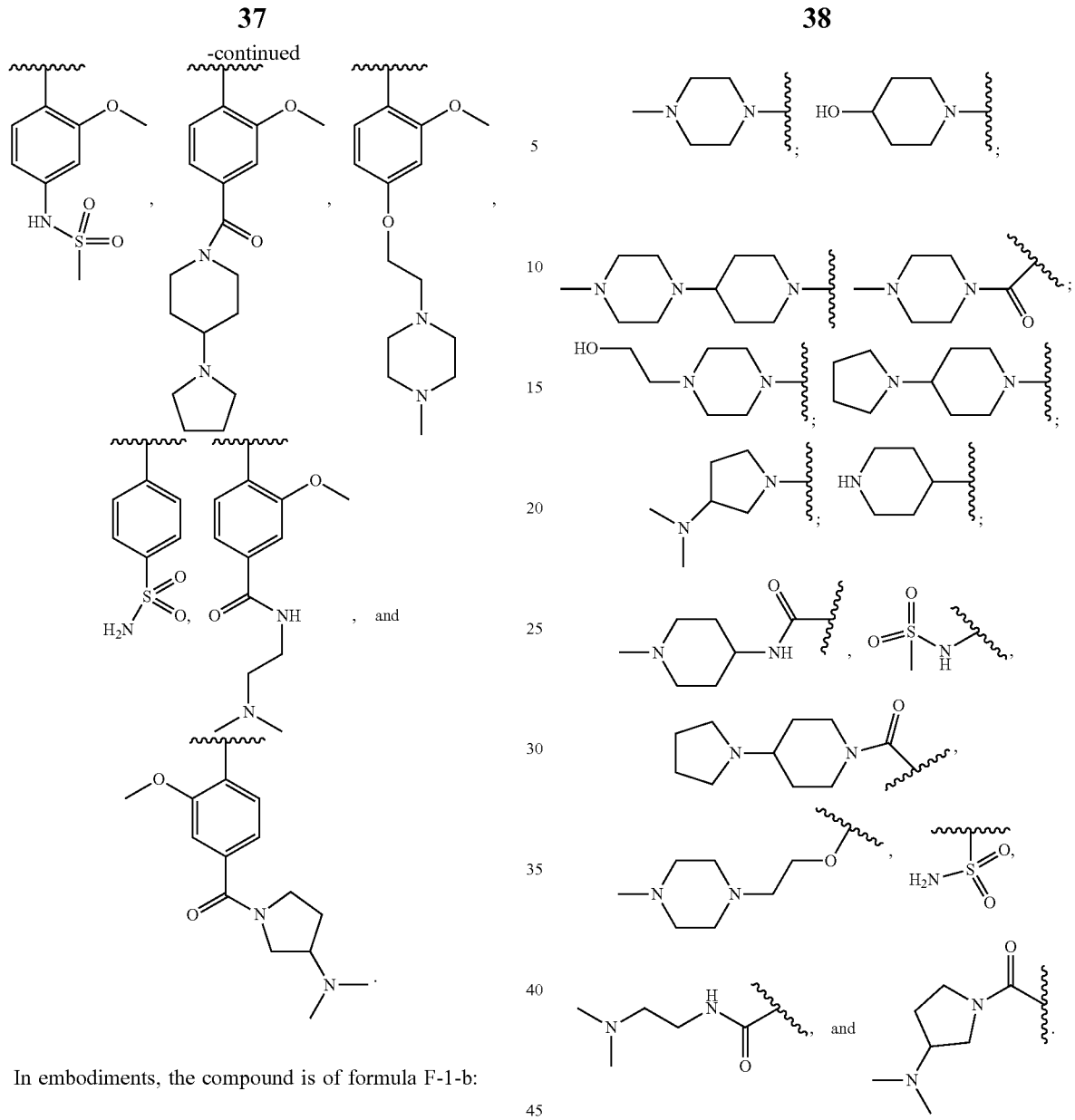

In embodiments, the compound is of formula F-1-b:

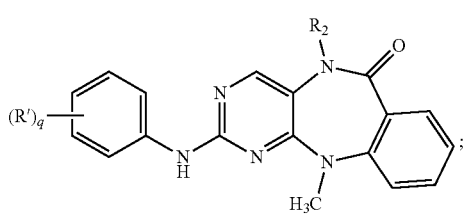
(F-1-b)

or a pharmaceutically acceptable salt, ester or prodrug thereof.

In embodiments, $R_2$ is unsubstituted alkyl.

In certain embodiments, $R_2$ is methyl, ethyl, propyl, or iso-propyl, each of which may be optionally substituted with one or more halogen such as F.

In certain embodiments, $R_2$ is —$CH_2$—$CH_2F$, —$CH_2$—$CHF_2$, or —$CH_2$—$CF_3$.

In certain embodiments, R' is selected from alkoxy, $CO_2Me$,

In certain embodiments, q is 1 or 2.

In certain embodiments, when q is 2, one R' is —$OCH_3$.

In embodiments, the compound has the structure of any one of Compounds 1-21 as described herein, or a pharmaceutically acceptable salt, ester or prodrug thereof.

In embodiments, the compound has a structure selected from the group consisting of:

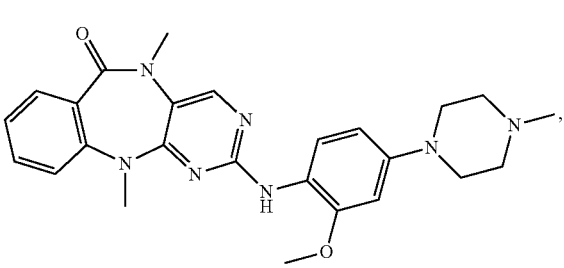

-continued
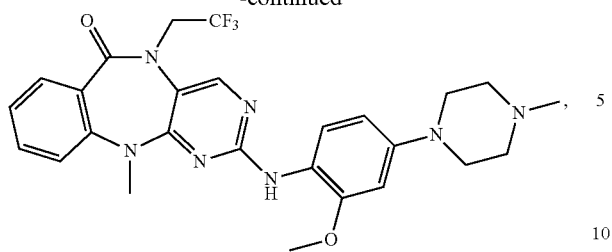
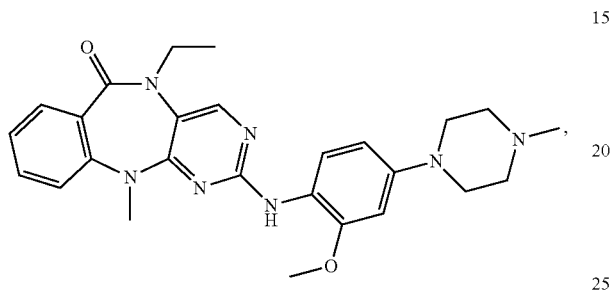
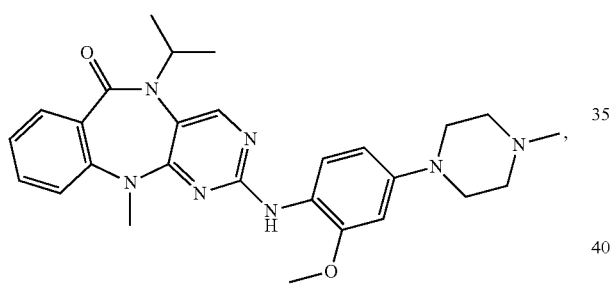
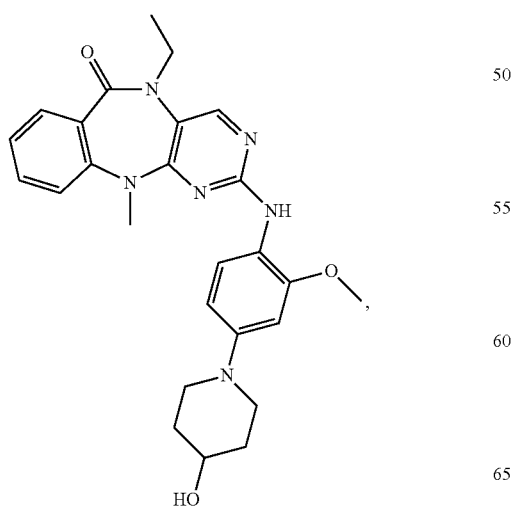
-continued
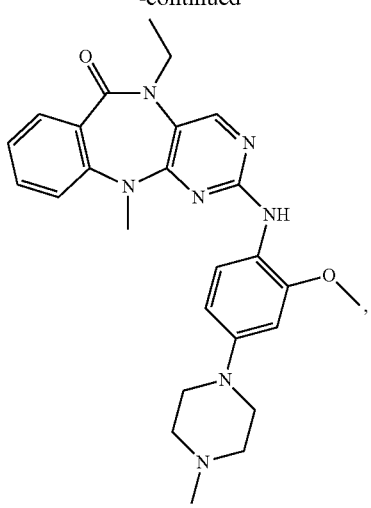
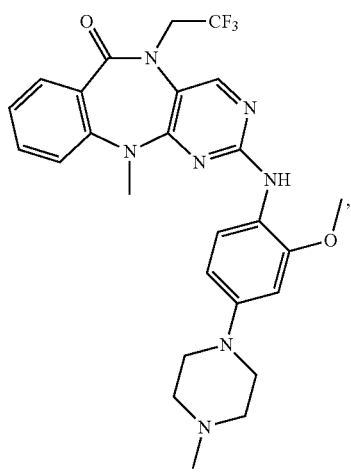
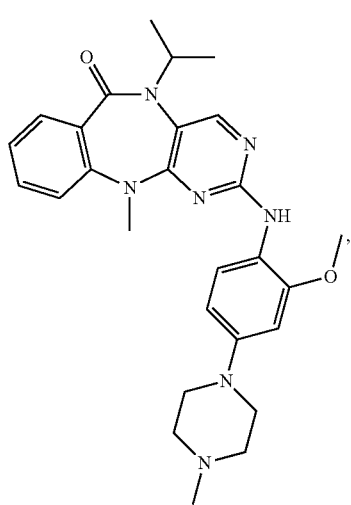

-continued
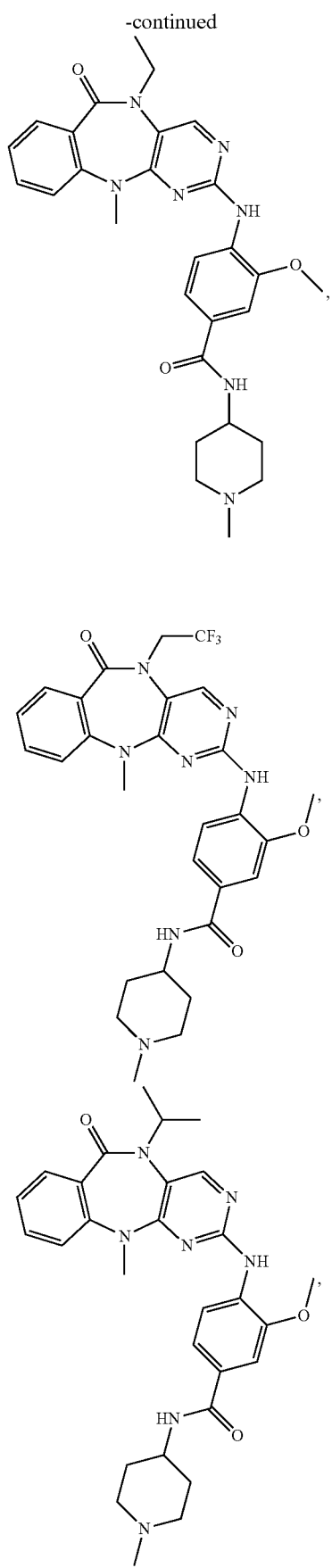
-continued
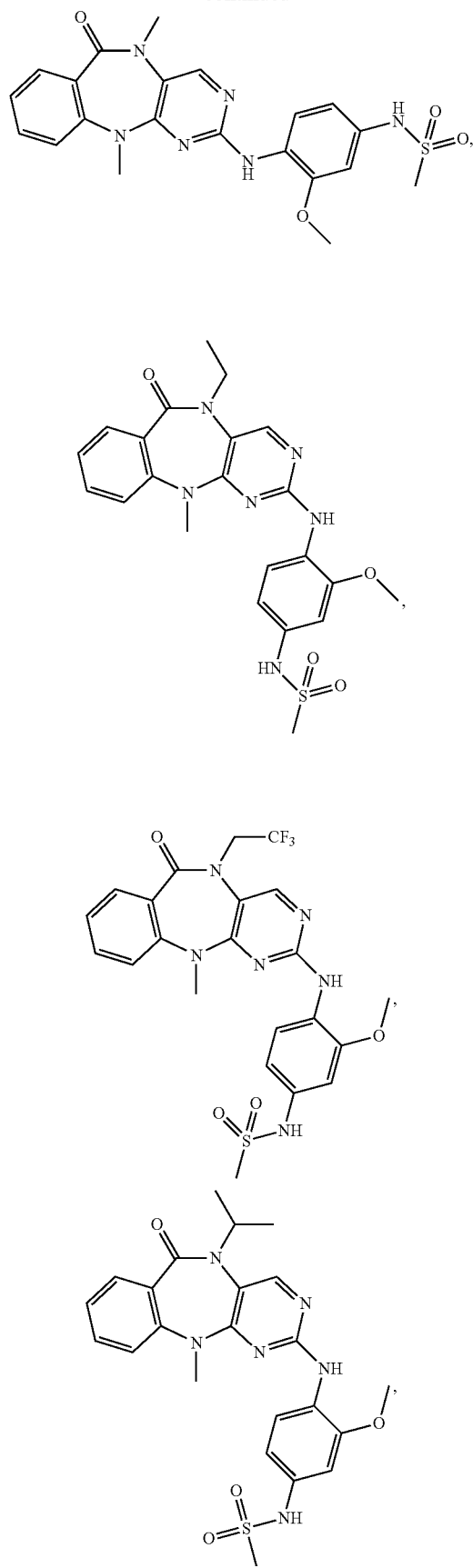

43
-continued
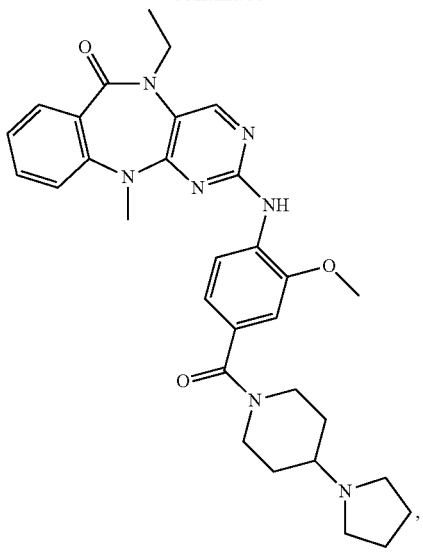
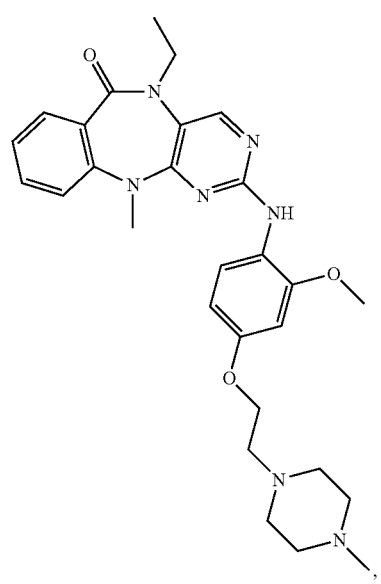
44
-continued
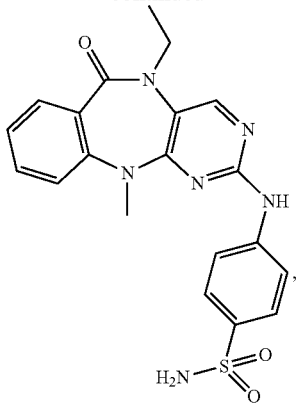
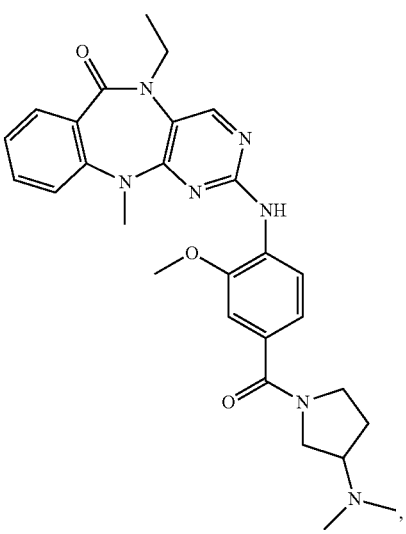
, and
or a pharmaceutically acceptable salt, ester or prodrug thereof.
In embodiments, the compound has a structure according to formula A-1:

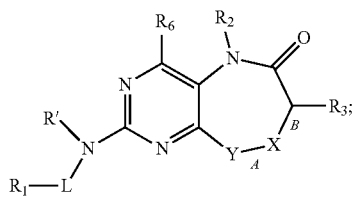

(A-1)

or a pharmaceutically acceptable salt, ester or prodrug thereof,
wherein,

X is $CHR_4$, $CR_4$, NH, $NR_4$ or N;

Y is $NR_5$, N, S, SO, $SO_2$, O, $CHR_5$, or $CR_5$; wherein at least one of X and Y is NH, $NR_4$, $NR_5$, N, S, SO, $SO_2$, or O;

A is a single bond or double bond;

B is a single bond or double bond, wherein both A and B are not double bonds;

R' is H or alkyl;

L is absent, S, SO, $SO_2$, or CO;

$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;

$R_2$ is hydrogen or optionally substituted alkyl;

$R_3$ is hydrogen, alkyl, alkenyl, aryl, arylalkyl, heteroaryl, heterocyclic, or carbocyclic, each of which may be optionally substituted;

$R_4$ is hydrogen, alkyl, alkenyl, aryl, arylalkyl, heteroaryl, heterocyclic, or carbocyclic, each of which may be optionally substituted;

$R_5$ is hydrogen, alkyl, alkenyl, aryl, arylalkyl, heteroaryl, heterocyclic, or carbocyclic, each of which may be optionally substituted;

or $R_3$ and X, together with the atoms to which they are attached, form a 3-8 membered carbocyclic, aryl, heterocyclic, or heteroaryl; each of which is optionally substituted;

or X and Y, together with the atoms to which they are attached, form a 3-8 membered carbocyclic, aryl, heterocyclic, or heteroaryl; each of which is optionally substituted; and $R_6$ is hydrogen or optionally substituted alkyl.

In certain embodiments, the invention provides a compound wherein X is $CR_4$ or $CHR_4$, and Y is $NR_5$.

In other embodiments, the invention provides a compound wherein $R_4$ is hydrogen, alkyl, aryl, heteroaryl, heterocyclic, or carbocyclic, each of which may be optionally substituted; and $R_5$ is hydrogen, alkyl, aryl, heteroaryl, heterocyclic, or carbocyclic, each of which may be optionally substituted.

In certain embodiments, the invention provides a compound wherein X and Y, together with the atoms to which they are attached, form a 3-8 membered cycloalkyl, aryl, heterocycloalkyl, or heteroaryl; each of which is optionally substituted.

In other embodiments, the invention provides a compound wherein $R_3$ and X, together with the atoms to which they are attached, form a 3-8 membered cycloalkyl, aryl, heterocycloalkyl, or heteroaryl; each of which is optionally substituted.

In some embodiments, the invention provides a compound wherein X is N and Y is $CR_5$.

In a further embodiment, $R_5$ is alkyl, aryl, heteroaryl, heterocyclic, or carbocyclic, each of which may be optionally substituted.

In embodiments, the invention provides a compound of B-1:

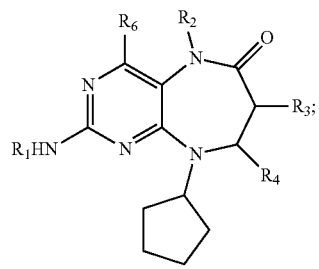

(B-1)

or a pharmaceutically acceptable salt, ester or prodrug thereof,
wherein, $R_1$ is aryl, or heteroaryl, wherein $R_1$ may be optionally substituted;

$R_2$ is hydrogen or optionally substituted alkyl;

$R_3$ is hydrogen or methyl;

$R_4$ is hydrogen or methyl; and $R_6$ is hydrogen.

In one embodiment, $R_1$ is phenyl or pyridyl, each of which may be optionally substituted.

In a further embodiment, $R_1$ is substituted with 0-4 substituents, selected from $N(R_A)(R_A)$, $C(O)NH(R_A)$, alkoxy, and heterocyclic, each of which may be further substituted; wherein each $R_A$ is independently selected from alkyl, and heterocyclic.

In another further embodiment, $R_1$ is substituted with 0-4 substituents, selected from alkoxy,

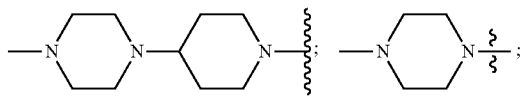

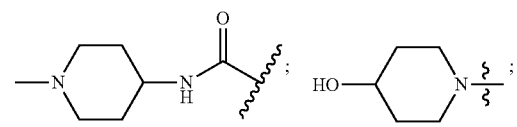

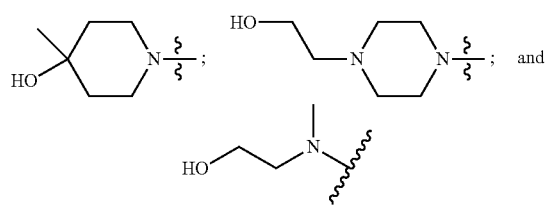

In embodiments, the invention provides a compound of formula C-1:

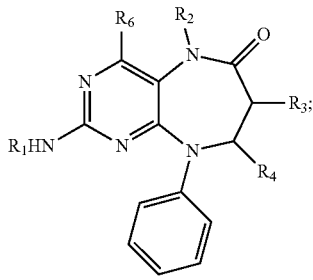

(C-1)

or a pharmaceutically acceptable salt, ester or prodrug thereof, wherein, $R_1$ is aryl, heteroaryl, which may be optionally substituted;

$R_2$ is hydrogen or methyl;

$R_3$ is hydrogen;

$R_4$ is hydrogen; and $R_6$ is hydrogen.

In certain embodiments, $R_1$ is phenyl or pyridyl, each of which may be optionally substituted.

In a further embodiment, $R_1$ is substituted with 0-4 substituents, selected from alkoxy, or heterocyclic, which may be further substituted.

In certain embodiments, $R_1$ is substituted with 0-4 substituents, selected from alkoxy,

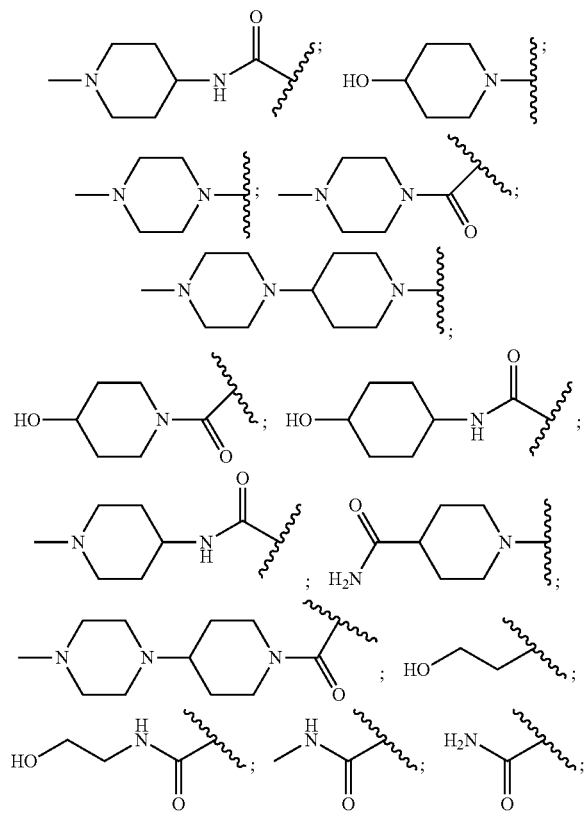

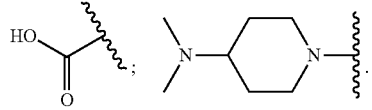

-continued

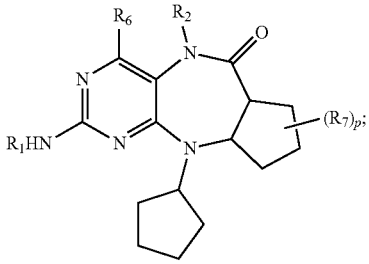

In embodiments, the invention provides a compound of formula D-1:

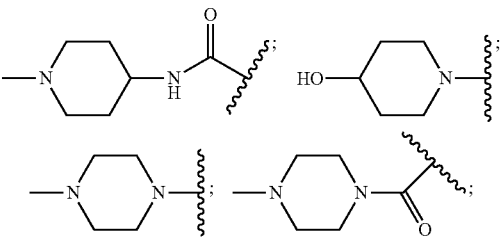

(D-1)

or a pharmaceutically acceptable salt, ester or prodrug thereof, wherein, $R_1$ is alkyl, aryl, heteroaryl, heterocyclic, or carbocyclic, wherein $R_1$ may be optionally substituted;

$R_2$ is hydrogen or optionally substituted alkyl;

$R_6$ is hydrogen or optionally substituted alkyl;

each $R_7$ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and p is 0-6.

In one embodiment, $R_1$ is methyl, ethyl, propyl, isopropyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In a further embodiment, $R_1$ is alkyl, phenyl, cyclohexyl, piperidinyl, quinolinyl, or pyridyl, each of which may be optionally substituted.

In certain embodiments, $R_1$ is substituted with 0-4 substituents, selected from halo, nitro, cyano, hydroxyl, amino, NH($R_4$), N($R_4$)($R_4$), CO$_2$H, C(O)$R_4$, C(O)O$R_4$, C(O)NH$_2$, C(O)NH($R_4$), C(O)N($R_4$)($R_4$), alkyl, aryl, arylalkyl, alkoxy, heteroaryl, heterocyclic, and carbocyclic, each of which may be further substituted; wherein each $R_4$ is independently selected from alkyl, carbocyclic, aryl, heteroaryl, and heterocyclic.

In certain embodiments, $R_1$ is substituted with 0-4 substituents, selected from alkyl, alkoxy, hydroxyl,

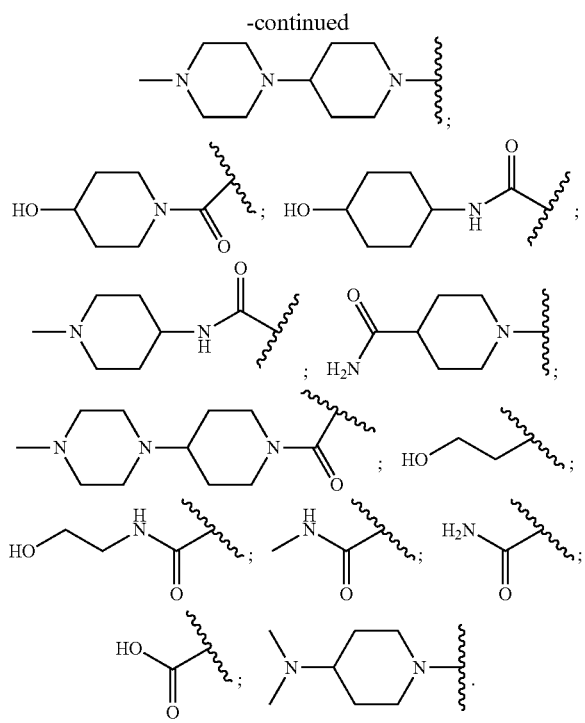

In embodiments, the invention provides a compound of formula E-1:

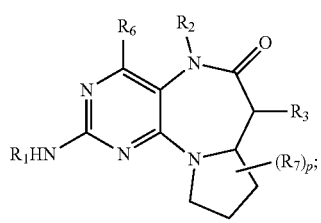
(E-1)

or a pharmaceutically acceptable salt, ester or prodrug thereof,
wherein,
$R_1$ is alkyl, aryl, heteroaryl, heterocyclic, or carbocyclic, wherein $R_1$ may be optionally substituted;
$R_2$ is hydrogen or optionally substituted alkyl;
$R_3$ is hydrogen or optionally substituted alkyl;
$R_6$ is hydrogen or optionally substituted alkyl;
each $R_7$ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and
p is 0-6.

In certain embodiments, $R_1$ is methyl, ethyl, propyl, iso-propyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In a further embodiment, $R_1$ is phenyl or pyridyl, each of which may be optionally substituted.

In another further embodiment, $R_1$ is substituted with 0-4 substituents, selected from halo, nitro, cyano, hydroxyl, amino, $NH(R_A)$, $N(R_A)(R_A)$, $CO_2H$, $C(O)R_A$, $C(O)OR_A$, $C(O)NH_2$, $C(O)NH(R_A)$, $C(O)N(R_A)(R_A)$, alkyl, aryl, arylalkyl, alkoxy, heteroaryl, heterocyclic, and carbocyclic, each of which may be further substituted; wherein each $R_A$ is independently selected from alkyl, carbocyclic, aryl, heteroaryl, and heterocyclic.

In certain embodiments, $R_1$ is substituted with 0-4 substituents, selected from alkoxy,

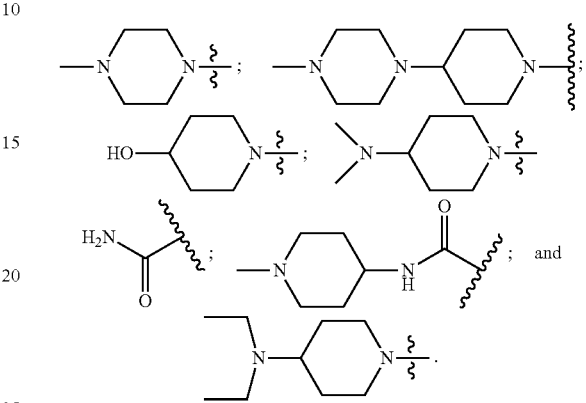

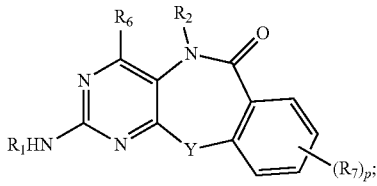

In embodiments, the invention provides a compound of formula F-I-1:

(F-I-1)

or a pharmaceutically acceptable salt, ester or prodrug thereof,
wherein,
Y is S, SO, $SO_2$, or O;
$R_1$ is alkyl, aryl, heteroaryl, heterocyclic, or carbocyclic, wherein $R_1$ may be optionally substituted;
$R_2$ is hydrogen or optionally substituted alkyl;
$R_6$ is hydrogen or optionally substituted alkyl;
each $R_7$ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and
p is 0-4.

In one embodiment, $R_1$ is methyl, ethyl, propyl, iso-propyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In a further embodiment, $R_1$ is phenyl or pyridyl, each of which may be optionally substituted.

In another embodiment, $R_1$ is substituted with 0-4 substituents, selected from halo, nitro, cyano, hydroxyl, amino, $NH(R_A)$, $N(R_A)(R_A)$, $CO_2H$, $C(O)R_A$, $C(O)OR_A$, $C(O)NH_2$, $C(O)NH(R_A)$, $C(O)N(R_A)(R_A)$, alkyl, aryl, arylalkyl, alkoxy, heteroaryl, heterocyclic, and carbocyclic, each of which may be further substituted;

wherein each $R_A$ is independently selected from alkyl, carbocyclic, aryl, heteroaryl, and heterocyclic.

In a further embodiment, $R_1$ is substituted with 0-4 substituents, selected from alkoxy, $CO_2Me$,

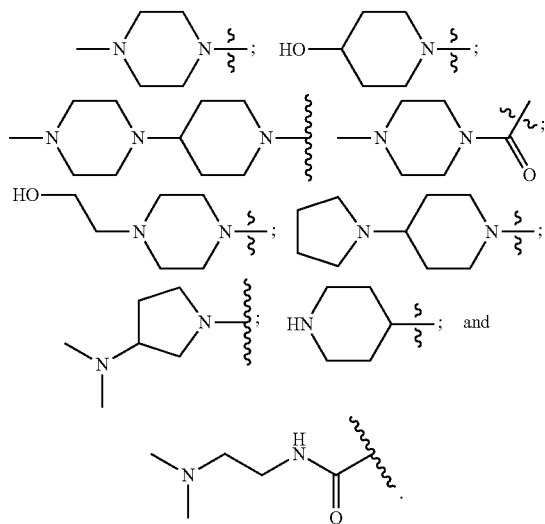

In embodiments, the invention provides a compound of formula G-1:

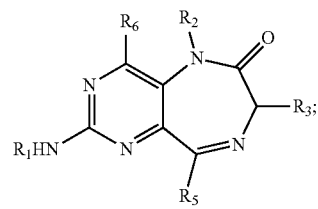

or a pharmaceutically acceptable salt, ester or prodrug thereof,
wherein,
$R_1$ is alkyl, alkenyl, alkynyl, each containing 0, 1, 2, or 3 heteroatoms selected from O, S, or N; or $R_1$ is aryl, arylalkyl, heteroaryl, heterocyclic, or carbocyclic, wherein $R_1$ may be optionally substituted;
$R_2$ is hydrogen or optionally substituted alkyl;
$R_3$ is hydrogen, alkyl, alkenyl, aryl, arylalkyl, heteroaryl, heterocyclic, or carbocyclic, each of which may be optionally substituted;
$R_5$ is hydrogen, alkyl, alkenyl, aryl, arylalkyl, heteroaryl, heterocyclic, or carbocyclic, each of which may be optionally substituted; and
$R_6$ is hydrogen or optionally substituted alkyl.

In one embodiment, $R_1$ is methyl, ethyl, propyl, isopropyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In a further embodiment, $R_1$ is optionally substituted phenyl.

In another embodiment, $R_1$ is substituted with 0-4 substituents, selected from halo, nitro, cyano, hydroxyl, amino, $NH(R_A)$, $N(R_A)(R_A)$, $CO_2H$, $C(O)R_A$, $C(O)NH_2$, $C(O)NH(R_A)$, $C(O)N(R_A)(R_A)$, alkyl, aryl, arylalkyl, alkoxy, heteroaryl, heterocyclic, and carbocyclic, each of which may be further substituted; wherein each $R_A$ is independently selected from alkyl, carbocyclic, aryl, heteroaryl, and heterocyclic.

In certain embodiments, $R_1$ is substituted with 0-4 substituents, selected from alkoxy, hydroxyl,

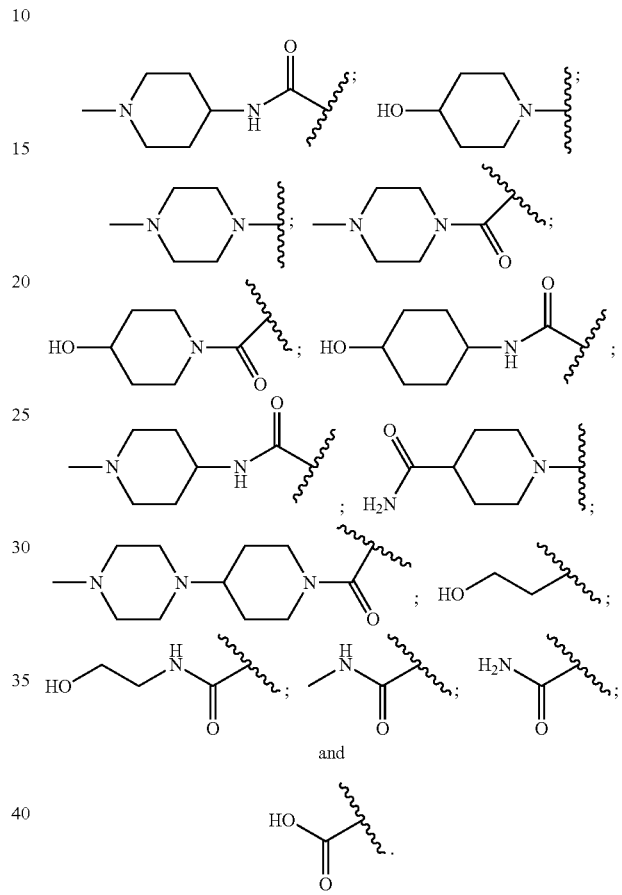

In another embodiment, $R_5$ is optionally substituted phenyl or optionally substituted cyclopentyl.

In embodiments, the invention provides a compound of formula I-2:

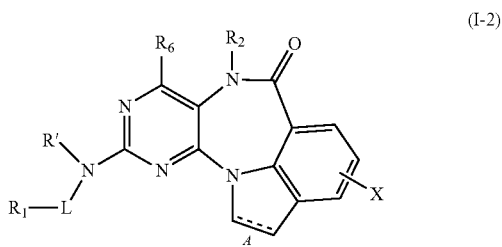

or a pharmaceutically acceptable salt, ester or prodrug thereof,
wherein,
A is a single bond or double bond;
R' is H or alkyl;
L is absent, S, SO, $SO_2$, or CO;

X is an optional substituent (for example, halogen, —OH, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O-C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$— C$_1$-C$_{12}$-alkyl, —OCO$_2$—C$_2$-C$_{12}$-alkenyl, —OCO$_2$—C$_2$-C$_{12}$-alkenyl, —OCO2-C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$— C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH-C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH— heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)— heteroaryl, —NHC(NH)-heterocycloalkyl, —C(NH)NH—C$_1$-C$_{12}$-alkyl, —C(NH)NH-C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)— heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, aryl, arylalkyl, heteroaryl, heteroarylalkyl, heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S— heteroaryl, —S-heterocycloalkyl, or methylthiomethyl);

R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;

R$_2$ is hydrogen, optionally substituted alkyl (including aralkyl), optionally substituted cycloalkyl, and optionally substituted heterocyclyl; and R$_6$ is hydrogen or optionally substituted alkyl.

In embodiments, the invention provides a compound of formula II-2:

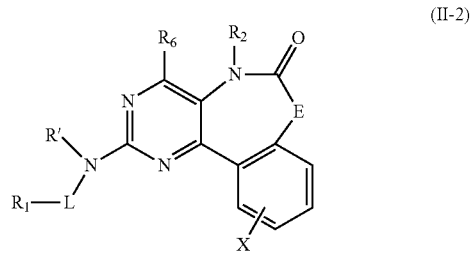

(II-2)

or a pharmaceutically acceptable salt, ester or prodrug thereof, wherein,

R' is H or alkyl;

L is absent, S, SO, SO$_2$, or CO;

X is an optional substituent as defined for formula I;

E is NR$_2$ or CHR$_2$;

R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;

R$_2$ is, independently for each occurrence, hydrogen, optionally substituted alkyl (including aralkyl), optionally substituted cycloalkyl, and optionally substituted heterocyclyl; and R$_6$ is hydrogen or optionally substituted alkyl.

In certain embodiments, E is NR$_2$. In certain embodiments, R$_2$ is H or —CH$_3$.

In embodiments, the invention provides a compound of formula III-2:

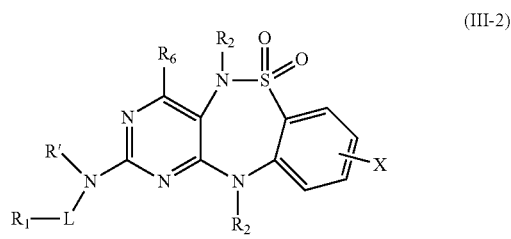

(III-2)

or a pharmaceutically acceptable salt, ester or prodrug thereof, wherein,

R' is H or alkyl;

L is absent, S, SO, SO$_2$, or CO;

X is an optional substituent as defined for formula I;

R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;

R$_2$ is, independently for each occurrence, hydrogen, optionally substituted alkyl (including aralkyl), optionally substituted cycloalkyl, and optionally substituted heterocyclyl; and R$_6$ is hydrogen or optionally substituted alkyl.

In embodiments, the invention provides a compound of formula IV-2:

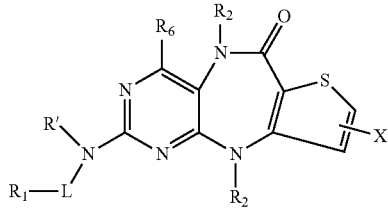
(IV-2)

or a pharmaceutically acceptable salt, ester or prodrug thereof,
wherein,

R' is H or alkyl;

L is absent, S, SO, SO$_2$, or CO;

R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;

R$_2$ is, independently for each occurrence, hydrogen, optionally substituted alkyl (including aralkyl), optionally substituted cycloalkyl, and optionally substituted heterocyclyl; and R$_6$ is hydrogen or optionally substituted alkyl.

In embodiments, the invention provides a compound of formula V-2:

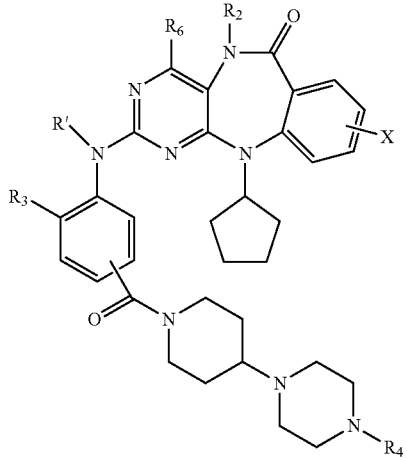
(V-2)

or a pharmaceutically acceptable salt, ester or prodrug thereof,
wherein,

R$_2$ is hydrogen or optionally substituted alkyl;

R$_3$ is —OH or —O-(optionally substituted alkyl);

R$_4$ is hydrogen or optionally substituted alkyl; and

R$_6$ is hydrogen or optionally substituted alkyl.

In embodiments, the invention provides a compound of Formula VI-2:

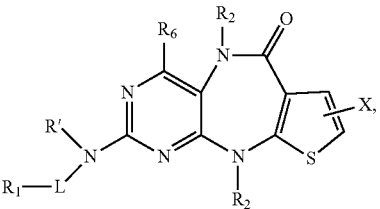
(VI-2)

or a pharmaceutically acceptable salt, ester or prodrug thereof,
wherein,

R' is H or alkyl;

L is absent, S, SO, SO$_2$, or CO;

X is an optional substituent as defined for formula I;

R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;

R$_2$ is, independently for each occurrence, hydrogen, optionally substituted alkyl, optionally substituted cycloalkyl, and optionally substituted heterocyclyl; or two X moieties on adjacent atoms of the thiophene ring can form, together with the atoms to which they are attached, a phenyl ring; and R$_6$ is hydrogen or optionally substituted alkyl.

In embodiments, the invention provides a compound of Formula VII-2:

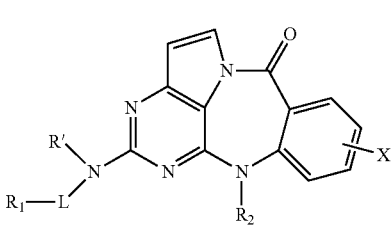
(VII-2)

or a pharmaceutically acceptable salt, ester or prodrug thereof,
wherein,

R' is H or alkyl;

L is absent, S, SO, SO$_2$, or CO;

X is an optional substituent as defined for formula I;

R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;

R$_2$ is hydrogen, optionally substituted alkyl, optionally substituted cycloalkyl, and optionally substituted heterocyclyl; and R$_6$ is hydrogen or optionally substituted alkyl.

In embodiments, the invention provides a compound of Formula VIII-2:

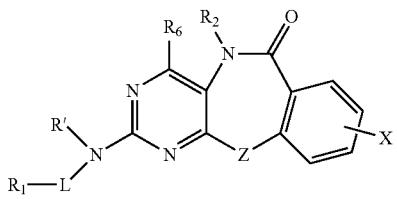

(VIII-2)

or a pharmaceutically acceptable salt, ester or prodrug thereof,
wherein,
R' is H or alkyl;
L is absent, S, SO, $SO_2$, or CO;
X is an optional substituent as defined for formula I;
Z is O or S;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;
$R_2$ is hydrogen, optionally substituted alkyl, optionally substituted cycloalkyl, and optionally substituted heterocyclyl; and
$R_6$ is hydrogen or optionally substituted alkyl.

In embodiments, the invention provides a compound of Formula IX-2:

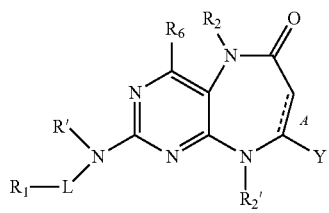

(X-2)

or a pharmaceutically acceptable salt, ester or prodrug thereof,
wherein,
A is a single bond or double bond;
R' is H or alkyl;
L is absent, S, SO, $SO_2$, or CO;
Y is hydrogen, optionally substituted alkyl, optionally substituted cycloalkyl, and optionally substituted heterocyclyl;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;
$R_2$ and $R_2'$ are each independently hydrogen, optionally substituted alkyl, optionally substituted cycloalkyl, and optionally substituted heterocyclyl;
or Y and $R_2'$ can form, together with the atoms to which they are attached, a five-membered ring; and
$R_6$ is hydrogen or optionally substituted alkyl.

Exemplary methods for preparation or synthesizing of these compounds are described herein and in, e.g., International Publication Nos. WO2010/080712 and WO2014145909, each of which is incorporated by reference in its entirety.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{35}S$, $^{32}P$, $^{125}I$, and $^{131}I$) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example, a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkyl-carbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P.G.M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods

In one aspect, the invention provides a method of treating a disease in a subject mediated by a kinase that is doublecortin-like kinase (DCLK1/2) comprising administering to the subject a DCLK inhibitor compound (e.g. compound of formula F-1, F-1-a, F-1-b of A-1) as described herein, or a pharmaceutically acceptable salt, ester or prodrug thereof. For instance, the DCLK inhibitor compound may selectively inhibit DCLK1 and/or DCLK2, with inhibition constant (Ki) for inhibiting DCLK1 and/or DCLK2 less than about 1 µM, less than about 500 nM, less than about 100 nM, less than about 50 nM, less than about 40 nM, less than about 30 nM, less than about 20 nM, or preferably, less than about 15 nM.

In another aspect, the invention provides a method for reducing doublecortin-like kinase (DCLK1/2)-dependent cell growth comprising contacting a cell with a DCLK inhibitor compound as described herein, or a pharmaceutically acceptable salt, ester or prodrug thereof.

In another aspect, the invention provides a method of inhibiting a doublecortin-like kinase (DCLK1/2) in a subject identified as in need of such treatment, comprising administering a DCLK inhibitor compound as described herein, or a pharmaceutically acceptable salt, ester or prodrug thereof.

In embodiments, the invention provides a method of inhibiting a disease, wherein the disease is mediated by DCLK1. In one embodiment, the invention provides a method of inhibiting a disease, wherein the disease is mediated by DCLK2. In one embodiment, the invention provides a method of inhibiting a disease, wherein the disease is mediated by DCLK1 and DCLK2.

In another embodiment, the invention provides a method of inhibiting a disease, wherein the disease is cancer or a proliferation disease.

In some embodiments, the cancer is lung cancer, colon cancer, breast cancer, prostate cancer, liver cancer, brain cancer, kidney cancer, ovarian cancer, stomach cancer, skin cancer, bone cancer, gastric cancer, pancreatic cancer, glioma, hepatocellular carcinoma, papillary renal carcinoma, head and neck squamous cell carcinoma, leukemia, lymphoma, myeloma, or a solid tumor.

In some embodiments, the cancer is a blood-borne cancer (e.g., chronic lymphocytic leukemia (CLL), follicular lymphoma (FL) or indolent non-Hodgkin's lymphoma (iNHL)). In an embodiment, the cancer is chronic lymphocytic leukemia (CLL), follicular lymphoma (FL), or indolent non-Hodgkin's lymphoma (iNHL).

In some embodiments, the cancer is pertinent to gastic organs, gastrointestinal tract, or digestive organs including stomach, small intestine, large intestine, tongue, salivary glands, pancreas, liver, and gallbladder.

In some embodiments, the disease is Barretts' esophagus, esophageal cancer, salivary gland malignancies, colon and colorectal cancer, intestinal cancer, gastric cancer, pancreatic cancer, skin cancer or neuroblastoma.

In some embodiments, the invention includes a method of reducing recurrence and/or relapse of the cancer or proliferation disease as described herein.

In some embodiments, the invention includes a method of reducing migration and/or metathesis of the cancer or proliferation disease as described herein.

In some embodiments, the invention includes a method of treating, reducing or preventing resistant cancer cells and/or cancer stem cells in patients suffered from or diagnosed with the cancer or proliferation disease as described herein.

In embodiments, the disease is a liver disease.

In some embodiments, the disease is a fatty liver disease, non-alcoholic fatty liver disease (NAFLD), non-alcoholic steatohepatitis (NASH), cirrhosis, fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Wolmans disease, or acute fatty liver of pregnancy.

In embodiments, the disease is a neurodegenerative disease.

In some embodiments, the disease is Alzheimer's disease (AD), Parkinson's disease (PD), Huntington's (HD) diseases, amyotrophic lateral sclerosis (ALS), spinal muscular atrophy (SMA), schizophrenia, attention-deficit/hyperactivity disorder (ADHD), fetal alcohol syndrome and diabetic encephalopathy.

In another aspect, the invention provides a method of treating a kinase mediated disorder in a subject comprising: administering to the subject identified as in need thereof a kinase inhibitor compound as described herein, or a pharmaceutically acceptable salt, ester or prodrug thereof.

In embodiments, a compound described herein is an inhibitor of DCLK1. In embodiments, a compound described herein is an inhibitor of DCLK2. In embodiments, a compound described herein is a selective inhibitor of DCLK1. In embodiments, a compound described herein is a selective inhibitor of DCLK2. In embodiments, a compound described herein is a dual inhibitor of DCLK1 and DCLK2. In embodiments, a compound described herein is a selective dual inhibitor of DCLK1 and DCLK2.

In embodiments, the subject is administered an additional therapeutic agent. In some embodiments, an additional therapeutic agent is an anti-inflammatory agent. In some embodiments, an additional therapeutic agent is a chemotherapy agent. In some embodiments, an additional therapeutic agent is a monoclonal antibody. In some embodiment, an additional therapeutic agent is a therapeutic agent for liver disease. In some embodiments, an additional therapeutic agent is a therapeutic agent for neurodegenerative disease.

In a further embodiment, the compound and the additional therapeutic agent are administered simultaneously or sequentially.

In another aspect, the invention provides a method for reducing kinase-dependent cell growth comprising contacting a cell with a kinase inhibitor compound as described herein.

In other aspects, the invention provides a method of inhibiting kinase in a subject identified as in need of such treatment, comprising administering a kinase inhibitor compound as described herein.

In embodiments, the invention provides a method wherein the subject is a human.

In other embodiments, the invention provides a method wherein the kinase inhibitor has a Ki for inhibiting DCLK1 and/or DCLK2 less than about 1 µM, less than about 500 nM, less than about 100 nM, less than about 50 nM, less than about 40 nM, less than about 30 nM, less than about 20 nM, or less than about 15 nM.

In one embodiment, the invention provides a method of synthesizing a kinase inhibitor compound as described herein. For example, the compounds (e.g. compounds of formulae F-1, F-1-a and F-1-b) can be synthesized as described herein (e.g., Schemes 1-4 in Examples).

Another aspect of this invention provides compounds or compositions that are inhibitors of protein kinases (e.g., DCLK, including DCLK1 and/or DCLK2), and thus are useful for the treatment of the diseases, disorders, and conditions, along with other uses described herein. In certain embodiments, these compositions optionally further comprise one or more additional therapeutic agents.

As inhibitors of protein kinases (e.g., DCLK, including DCLK1 and/or DCLK2), the compounds and compositions of this invention are particularly useful for treating or lessening the severity of a disease, condition, or disorder where a protein kinase is implicated in the disease, condition, or disorder.

In one aspect, the present invention provides a method for treating or lessening the severity of a disease, condition, or disorder where a protein kinase is implicated in the disease state. In another aspect, the present invention provides a method for treating or lessening the severity of a kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said method is used to treat or prevent a condition selected from autoimmune diseases, inflammatory diseases, cancers, tumors, malignant tumors, proliferative and hyperproliferative diseases, immunologically-mediated diseases, bone diseases, metabolic diseases, neurological and neurodegenerative diseases, cardiovascular diseases, liver disease, hormone related diseases, allergies, asthma, and neurodegenerative diseases including Alzheimer's disease. In other embodiments, said condition is selected from a proliferative disorder, liver disease and a neurodegenerative disorder.

One aspect of this invention provides compounds that are useful for the treatment of diseases, disorders, and conditions characterized by excessive or abnormal cell proliferation. Such diseases include, a proliferative or hyperproliferative disease, cancer, liver disease and a neurodegenerative disease. Examples of proliferative and hyperproliferative diseases include, without limitation, cancer.

The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma;

melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum, brain and central nervous system; chronic myeloid leukemia (CML), and leukemia.

In some embodiments, the compounds of this invention are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease.

In some embodiments, the compounds of this invention are useful for treating hematopoietic disorders, in particular, acute-myelogenous leukemia (AMLi), chronic-myelogenous leukemia (CML), acute-promyelocytic leukemia, and acute lymphocytic leukemia (ALL).

In some embodiments, the compounds of this invention are useful for treating a cancer or proliferative disease pertinent to gastic organs, gastrointestinal tract, and digestive organs including the stomach, small intestine, large intestine, tongue, salivary glands, pancreas, liver, and gallbladder.

In some embodiments, the compounds of this invention are useful for treating Barretts' esophagus, esophageal cancer, salivary gland malignancies, colon and colorectal cancer, intestinal cancer, gastric cancer, pancreatic cancer, skin cancer and neuroblastoma.

One aspect of this invention provides compounds that are useful for the treatment of diseases, disorders, and damages in liver.

In some embodiments, the compounds of this invention are useful for treating a fatty liver disease, non-alcoholic fatty acid liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, or lipodystrophy.

One aspect of this invention provides compounds that are useful for the treatment of a neurodegenerative disease.

In some embodiments, the disease is Alzheimer's disease (AD), Parkinson's disease (PD), Huntington's (HD) diseases, amyotrophic lateral sclerosis (ALS), spinal muscular atrophy (SMA), schizophrenia, attention-deficit/hyperactivity disorder (ADHD), fetal alcohol syndrome and diabetic encephalopathy.

Another aspect of this invention provides a method for the treatment or lessening the severity of a disease selected from a cancer, a proliferative or hyperproliferative disease, a liver disease, or a neurodegenerative disease, comprising administering an effective amount of a compound, or a pharmaceutically acceptable composition comprising a compound, to a subject in need thereof.

As inhibitors of protein kinases, the compounds and compositions of this invention are also useful in biological samples. One aspect of the invention relates to inhibiting protein kinase activity in a biological sample, which method comprises contacting said biological sample with a compound of the invention or a composition comprising said compound. The term "biological sample", as used herein, means an in vitro or an ex vivo sample, including, without limitation, cell cultures or extracts thereof, biopsied material obtained from a mammal or extracts thereof; and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme (e.g. kinetics, binding and inhibition) assays, gel shift assays (electrophoretic mobility shift assay) and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Preferably, in vitro assays quantitate the ability of the inhibitor to bind to the protein kinase and may be measured either by probing the inhibitor with fluorescent molecules prior to binding, isolating the inhibitor/kinase complex and determining the amount of the bound probes, utilization of a mobility shift assay with substrates treated or non-treated with protein kinase, for example, in the presence of ATP plus inhibitor or DMSO control, or by running a competition experiment where new inhibitors are incubated with the kinase bound to known fluorescent probes.

Detailed conditions for assaying a compound utilized in this invention as an inhibitor of various kinases are set forth in the Examples below.

In accordance with the foregoing, the present invention further provides a method for preventing or treating any of the diseases or disorders described above in a subject in need of such treatment, which method comprises administering to said subject a therapeutically effective amount of a compound of the invention or a pharmaceutically acceptable salt thereof. For any of the above uses, the required dosage will vary depending on the mode of administration, the particular condition to be treated and the effect desired.

Pharmaceutical Compositions

In another aspect, the invention provides a pharmaceutical composition comprising a kinase inhibitor compound (e.g. DCLK1/2) as described herein, or a pharmaceutically acceptable ester, salt, or prodrug thereof, together with a pharmaceutically acceptable carrier.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA41g. Where the compounds of the invention are administered in conjunction with other therapies, dosages of the co-administered compounds will of course vary depending on the type of co-drug employed, on the specific drug employed, on the condition being treated and so forth.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/Kg to about 500 mg/Kg, alternatively from about 1 to about 50 mg/Kg. In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The invention also provides for a pharmaceutical combinations, e.g. a kit, comprising a) a first agent which is a kinase inhibitor compound as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the invention and a co-agent, are both administered to a patient simultaneously in the form of a single entity or dosage. The term "non-fixed combination" means that the active ingredients, e.g. a compound of the invention and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

In certain embodiments, these compositions optionally further comprise one or more additional therapeutic agents. For example, chemotherapeutic agents or other antiproliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the compounds of this invention may also be combined with include, without limitation: treatments for Alzheimer's Disease such as Aricept18 and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, antileukemic agents, and growth factors; and agents for treating immunodeficiency disorders such as gamma globulin. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention.

In another aspect, the invention provides a kit comprising a compound capable of inhibiting kinase activity selected from one or more of the kinase inhibitor compounds described herein, and instructions for use in treating cancer.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Abbreviations

DCLK1, doublecortin like kinase 1.

DCLK2, doublecortin like kinase 2.

Ni-NTA, nickel-nitrilotriacetic acid

FAM, fluorescein amidite

HTS, high-throughput screening

HEPES, 4-(2-hydroxyethyl)-1-piperazineethanesulfonic acid

DTT, dithiothreitol

EDTA, ethylenediaminetetraacetic acid

Chemistry

General Methods

Unless otherwise noted, reagents and solvents were obtained from commercial suppliers and were used without further purification. $^1$H NMR spectra were recorded on a 500 MHz Bruker Avance III spectrometer and chemical shifts are reported in parts per million (ppm, δ) downfield from tetramethylsilane (TMS). Coupling constants (J) are reported in Hz. Spin multiplicities are described as s (singlet), br (broad singlet), d (doublet), t (triplet), q (quartet), and m (multiplet). Mass spectra were obtained on a Waters Acquity I UPLC. Preparative HPLC was performed on a Waters Sunfire C18 column (19 mm×50 mm, 5 μM) using a gradient of 15-95% methanol in water containing 0.05% trifluoroacetic acid (TFA) over 22 min (28 min run time) at a flow rate of 20 mL/min. Assayed compounds were isolated and tested as TFA salts. Purities of assayed compounds were in all cases greater than 95%, as determined by reverse-phase HPLC analysis.

Synthesis i. Scheme 1: Synthesis of Compound 1

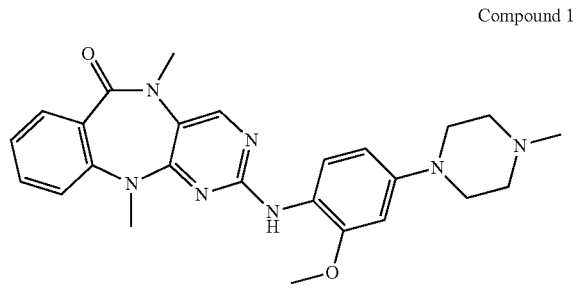 [SMILES: COc1cc(N2CCN(C)CC2)ccc1Nc1ncc2c(n1)N(C)c1ccccc1C(=O)N2C]

Compound 1

Compound 1 can be synthesized using the following scheme 1.

Scheme 1

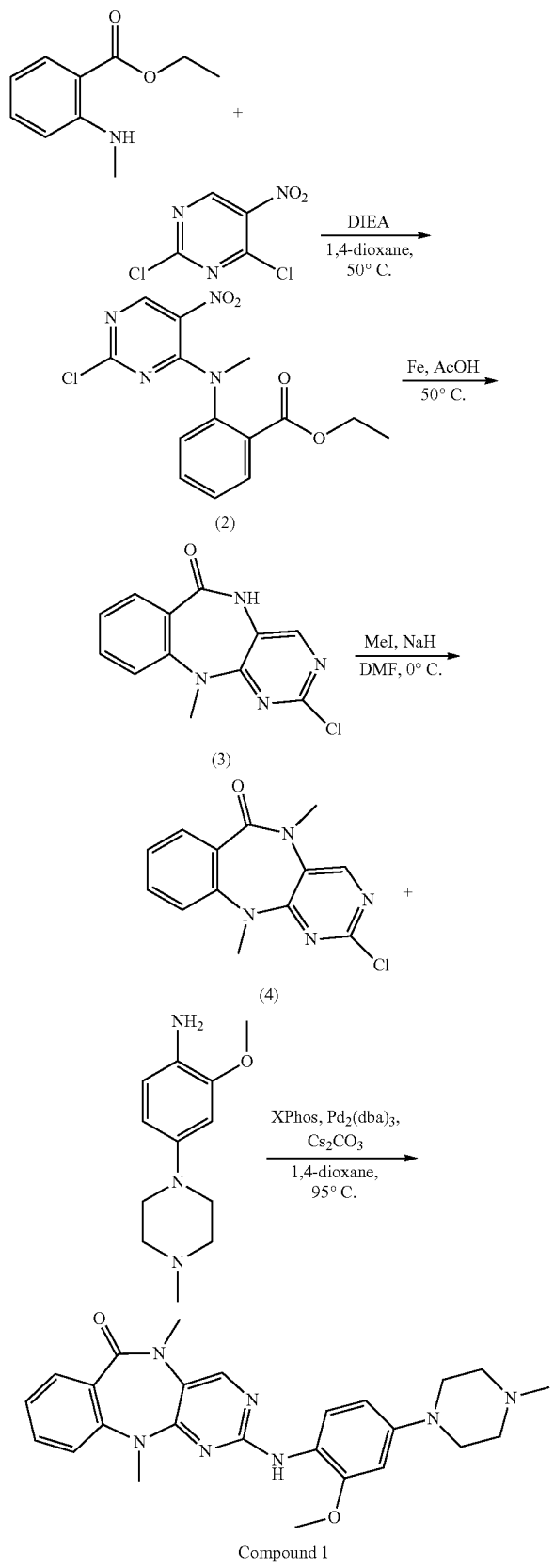

(2)

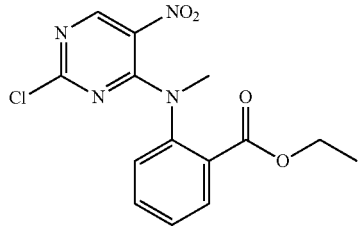

In Scheme 1, ethyl 2-((2-chloro-5-nitropyrimidin-4-yl)(methyl)amino)benzoate (2) can be synthesized as follows: A mixture of ethyl 2-(methylamino)benzoate (1.44 g, 8.0 mmol), diisopropylethylamine (DIEA) (2.8 mL, 16.0 mmol) and 2,4-dichloro-5-nitropyrimidine (2.30 g, 12.0 mmol) in dioxane (40 mL) was heated at 50° C. for 6 hours. After the reaction was complete as monitored by thin layer chromatography (TLC), the reaction solution was concentrated and the residue was purified by silica-gel column chromatography with ethyl acetate and hexane (1/20, v/v) to give the title compound (2.51 g, 93%). $^1$H NMR (600 MHz, CDCl3) δ 8.44 (s, 1H), 8.02 (d, J=7.2 Hz, 1H), 7.59 (t, J=7.2 Hz, 1H), 7.44 (t, J=7.2 Hz, 1H), 7.22 (d, J=7.8 Hz, 1H), 4.28-4.18 (m, 2H), 3.58 (s, 3H), 1.29 (t, J=7.2 Hz, 3H). $^{13}$C NMR (150 MHz, CDCl3) δ 164.4, 160.8, 157.0, 155.2, 142.8, 134.1, 132.5, 128.9, 127.7, 61.6, 42.0, 14.0. MS (ESI) m/z 337 (M+H)$^+$ (3)

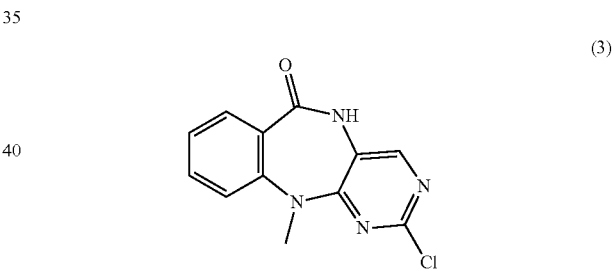

In Scheme 1, 2-chloro-11-methyl-5,11-dihydro-6H-benzo[e]pyrimido[5,4-b][1,4]diazepin-6-one (3) can be synthesized as follows:

A mixture of (2) (2.35 g, 6.98 mmol) and iron power (3.9 g, 69.8 mmol) in acetic acid (100 mL) was heated at 50° C. for 9 hours. After the reaction was complete as monitored by reverse phase analytical liquid-chromatography electrospray mass spectrometry (LC-MS), the excess of iron was removed and the mixture was concentrated in vacuo. The resulting residue was poured into ice-water which resulted in a solid precipitate that was collected by filtration, washed with water and air dried to give the title compound (1.55 g, 85%). $^1$H NMR (600 MHz, DMSO-d6) δ 10.44 (s, 1H), 8.14 (s, 1H), 7.72 (d, J=4.8 Hz, 1H), 7.58 (s, 1H), 7.27 (d, J=6.0 Hz, 1H), 7.21 (s, 1H), 3.33 (s, 3H). $^{13}$C NMR (150 MHz, DMSO-d6) δ 167.6, 161.4, 153.4, 149.7, 147.9, 134.2, 132.0, 125.9, 124.6, 124.3, 120.1, 37.2. MS (ESI) m/z 261 (M+H)$^+$ (4)

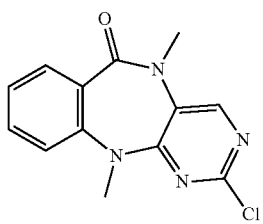

In Scheme 1, 2-chloro-5,11-dimethyl-5,11-dihydro-6H-benzo[e]pyrimido[5,4-b][1,4]diazepin-6-one (4) can be synthesized as follows:

To a stirred suspension of (3) 688 mg, 2.64 mmol) and Met (0.25 mL, 4.0 mmol) in dimethyl acetamide (DMA, 40.0 mL) was added NaH (360 mg, 60% suspension in mineral oil) at −10° C. and the reaction was gradually warmed to 0° C. After the reaction was complete as monitored by LC-MS, the solution was poured into ice-water which resulted in a solid precipitate. The precipitate was collected by filtration, washed with water and air dried to give the title compound (563 mg, 77%). $^1$H NMR (600 MHz, DMSO-d6) δ 8.57 (s, 1H), 7.68 (dd, J=1.2, 7.2 Hz, 1H), 7.54-7.51 (m, 1H), 7.25 (d, J=7.8 Hz, 1H), 7.20-7.18 (m, 1H), 3.41 (s, 3H), 3.32 (s, 3H). $^{13}$C NMR (150 MHz, DMSO-d6) δ 167.1, 163.8, 153.7, 153.4, 148.6, 133.5, 132.4, 128.7, 126.0, 124.6, 118.9, 38.1, 36.4. MS (ESI) m/z 275 (M+H)$^+$.

(XMD8-85-1; Compound 1)

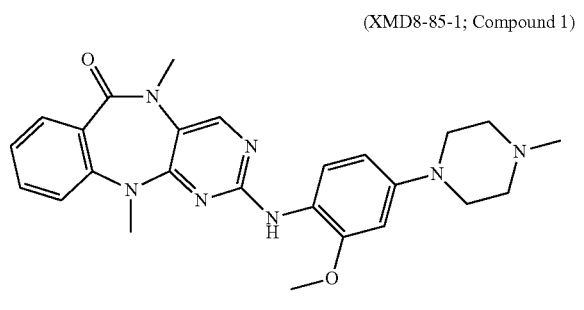 [SMILES: COc1cc(N2CCN(C)CC2)ccc1Nc1ncc2c(n1)N(C)c1ccccc1C(=O)N2C]

In Scheme 1, 2-((2-methoxy-4-(4-methylpiperazin-1-yl)phenyl)amino)-5,11-dimethyl-5,11-dihydro-6H-benzo[e]pyrimido[5,4-b][1,4]diazepin-6-one (XMD8-85-1, or Compound 1) can be synthesized as follows:

A mixture of (4) (26 mg, 0.1 mmol), 2-methoxy-4-(4-methylpiperizin-1-yl)benzamine (22 mg, 0.1 mmol), X-Phos (4.3 mg), Pd$_2$(dba)$_3$ (5.5 mg) and K$_2$CO$_3$ (41.5 mg, 0.3 mmol) in 1.2 mL of t-BuOH was heated at 100° C. in a seal tube for 4 h. Then the reaction was filtered through celite and eluted with dichloromethane. The dichloromethane was removed in vacuo and the resulting crude product was purified by reverse-phase prep-HPLC using a water (0.05% TFA)/acetonitrile (0.05% TFA) gradient to afford the compounds as TFA salt (20 mg, yield: 36%). $^1$H NMR (600 MHz, CD3OD) δ 7.83 (dd, J=1.2, 7.8 Hz, 1H), 7.71 (s, 1H), 7.62-7.59 (m, 2H), 7.30 (d, J=8.4 Hz, 1H), 7.26 (t, J=7.2 Hz, 1H), 6.75 (d, J=1.8 Hz, 1H), 6.66 (d, J=7.2 Hz, 1H), 3.92-3.87 (m, 5H), 3.66-3.60 (m, 2H), 3.49 (s, 3H), 3.30-3.24 (m, 2H), 3.14-3.08 (m, 2H), 2.97 (s, 3H). MS (ESI) m/z 446 (M+H)$^+$.

ii. Scheme 2: Synthesis of Compound 2

(FMF-03-146-1; Compound 2)

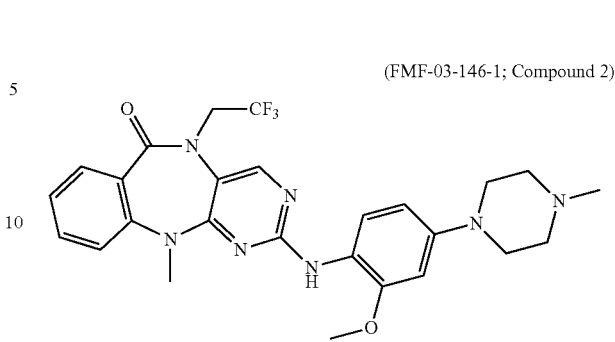

Compound 2: 2-((2-methoxy-4-(4-methylpiperazin-1-yl)phenyl)amino)-11-methyl-5-(2,2,2-trifluoroethyl)-5,11-dihydro-6H-benzo[e]pyrimido[5,4-b][1,4]diazepin-6-one (FMF-03-146-1)

$^1$H NMR (500 MHz, DMSO-d$_6$) δ 9.85 (s, 1H), 8.48 (s, 1H), 8.18 (s, 1H), 7.78-7.67 (m, 2H), 7.57-7.50 (m, 1H), 7.30-7.25 (m, 1H), 7.20 (td, J=7.6, 1.0 Hz, 1H), 6.71 (d, J=2.6 Hz, 1H), 6.61-6.53 (m, 1H), 3.86 (d, J=4.4 Hz, 1H), 3.83 (s, 2H), 3.54 (d, J=12.0 Hz, 2H), 3.29 (s, 2H), 3.23-3.12 (m, 2H), 2.95 (t, J=12.5 Hz, 2H), 2.88 (s, 3H). MS (ESI) m/z 528 (M+H)$^+$

Compound 2 can be synthesized using the following Scheme 2.

Scheme 2

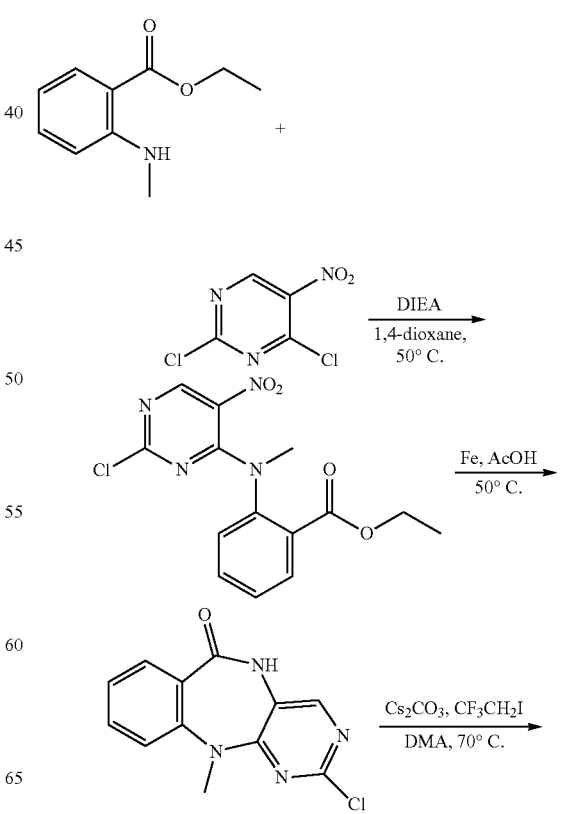

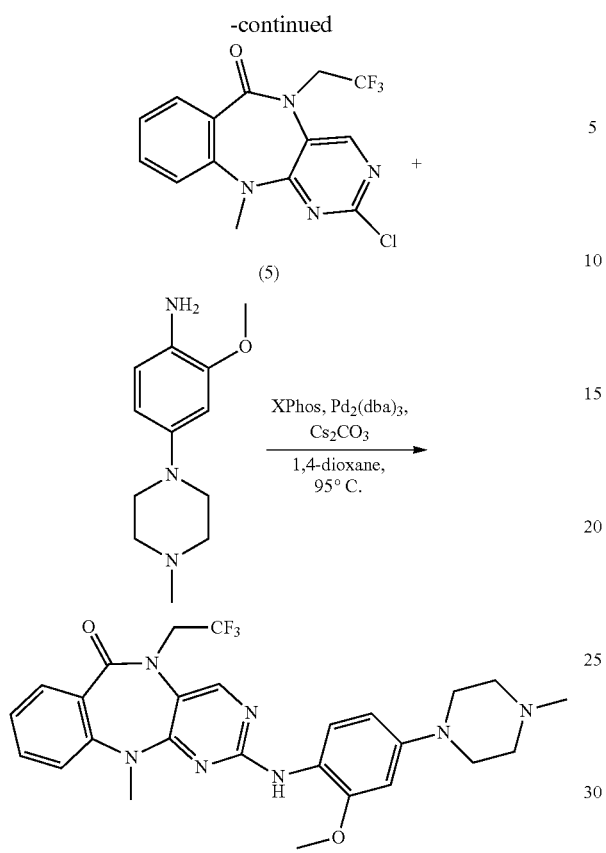

(5)

In Scheme 2, 2-chloro-11-methyl-5-(2,2,2-trifluoroethyl)-5,11-dihydro-6H-benzo[e]pyrimido[5,4-b][1,4]diazepin-6-one (5) can be synthesized as follows: 1, 2-chloro-11-methyl-5,11-dihydro-6H-benzo[e]pyrimido[5,4-b][1,4]diazepin-6-one (3) (500 mg, 1.9 mmol), Cs₂CO₃ (1.3 g, 4.0 mmol) and trifluoroethyl iodide (250 µL, 2.6 mmol) were dissolved in DMA (5 mL) and heated to 70° C. for 2 h. The solvent was evaporated and the residue purified by silica column chromatography (0-5% MeOH in DCM) to give the title compound (116 mg, 18%). $^1$H NMR (500 MHz, DMSO-d$_6$) δ 8.84 (s, 1H), 7.73 (dd, J=7.8, 1.7 Hz, 1H), 7.59 (ddd, J=8.4, 7.3, 1.7 Hz, 1H), 7.34 (dd, J=8.4, 0.9 Hz, 1H), 7.26 (ddd, J=8.0, 7.3, 1.0 Hz, 1H), 5.04 (br s, 2H), 3.38 (s, 3H). $^{13}$C NMR (126 MHz, DMSO-d$_6$) δ 167.79, 165.40, 155.37, 149.08, 134.04, 132.42, 126.15, 125.90, 125.17, 124.92, 123.66, 119.15, 48.61 (q, J=32.5 Hz), 36.30. MS (ESI) m/z 343 (M+H)$^+$ Other steps in Scheme 2 can be performed as described in Scheme 1.

iii. Scheme 3: Synthesis of Compound 3

(FMF-03-055-1; Compound 3)

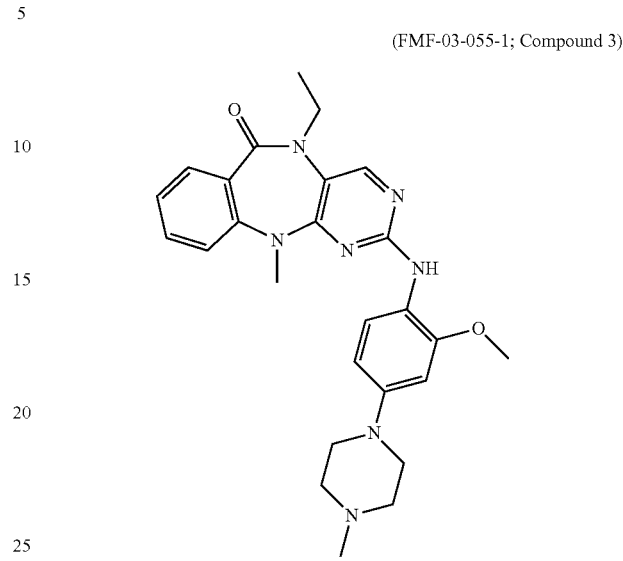

Compound 3: 5-ethyl-2-((2-methoxy-4-(4-methylpiperazin-1-yl)phenyl)amino)-11-methyl-5,11-dihydro-6H-benzo[e]pyrimido[5,4-b][1,4]diazepin-6-one (FMF-03-055-1)

$^1$H NMR (500 MHz, DMSO-d$_6$) δ 9.75 (s, 1H), 8.35 (s, 1H), 7.81 (d, J=8.7 Hz, 1H), 7.64 (dd, J=7.7, 1.7 Hz, 1H), 7.49 (ddd, J=8.7, 7.2, 1.7 Hz, 1H), 7.24-7.13 (m, 2H), 6.72 (d, J=2.6 Hz, 1H), 6.57 (dd, J=8.8, 2.6 Hz, 1H), 4.20-3.92 (m, 1H), 3.89 (s, 2H), 3.83 (s, 3H), 3.54 (d, J=12.1 Hz, 2H), 3.28 (s, 3H), 3.18 (q, J=10.9 Hz, 2H), 2.94 (t, J=12.6 Hz, 2H), 2.89 (d, J=3.4 Hz, 3H), 1.16 (t, J=7.1 Hz, 3H). MS (ESI) m/z 474 (M+H)$^+$ Compound 3 can be synthesized using the following Scheme 3.

Scheme 3

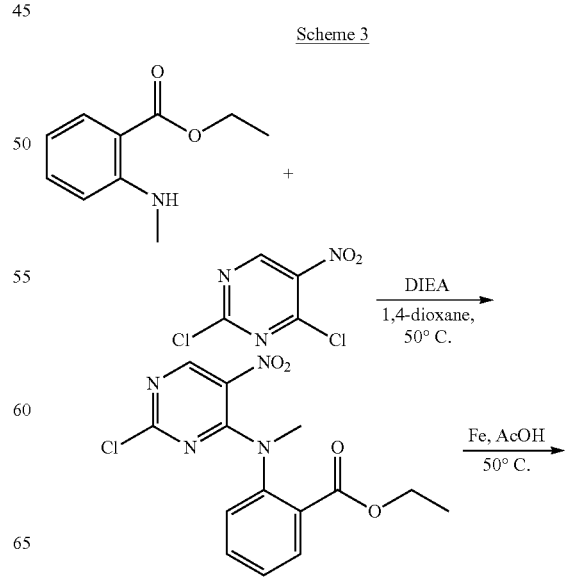

153.61, 148.71, 133.30, 132.08, 127.49, 126.71, 124.70, 118.82, 46.09, 36.31, 13.82. MS (ESI) m/z 290 (M+H)$^+$

Other steps in Scheme 3 can be performed as described in Scheme 1.

iv. Scheme 4: Synthesis of Compound 4

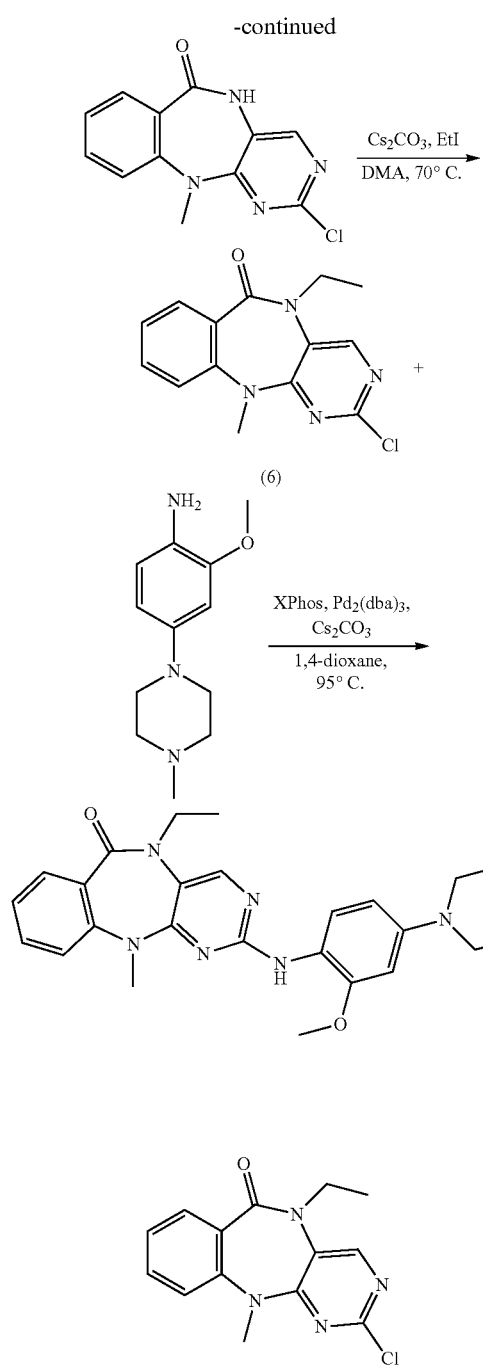

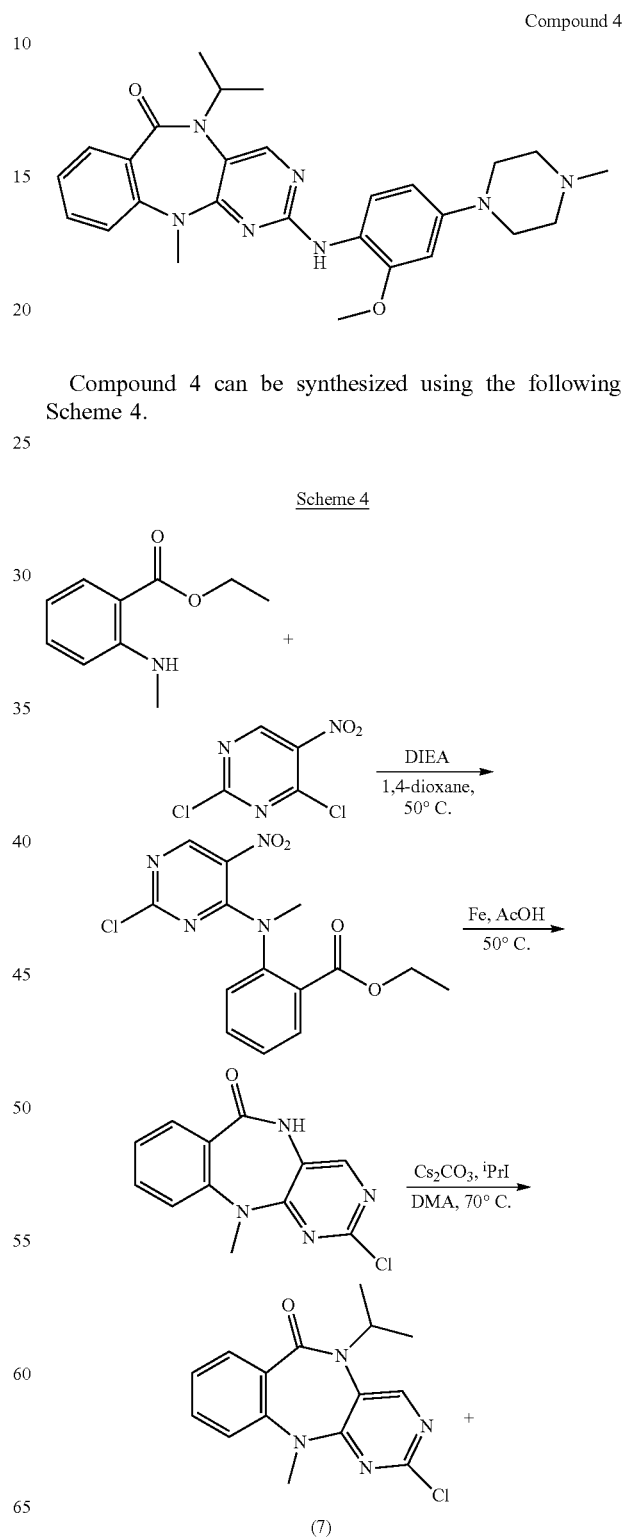

Compound 4 can be synthesized using the following Scheme 4.

In Scheme 3, 2-chloro-5-ethyl-11-methyl-5,11-dihydro-6H-benzo[e]pyrimido[5,4-b][1,4]diazepin-6-one (6) can be synthesized as follows: 1, 2-chloro-11-methyl-5,11-dihydro-6H-benzo[e]pyrimido[5,4-b][1,4]diazepin-6-one (3) (500 mg, 1.9 mmol), Cs$_2$CO$_3$ (1.3 g, 4.0 mmol) and ethyl iodide (210 µL, 2.6 mmol) were dissolved in DMA (5 mL) and heated to 70° C. for 2 h. The solvent was evaporated and the residue purified by silica column chromatography (0-5% MeOH in DCM) to give the title compound (280 mg, 51%). $^1$H NMR (500 MHz, DMSO-d$_6$) δ 8.65 (s, 1H), 7.66 (dd, J=7.8, 1.7 Hz, 1H), 7.53 (ddd, J=8.4, 7.3, 1.7 Hz, 1H), 7.27 (dd, J=8.4, 1.0 Hz, 1H), 7.22 (td, J=7.5, 1.0 Hz, 1H), 4.10 (q, J=5.2 Hz, 2H), 3.18 (s, 3H), 1.20 (t, J=7.1 Hz, 3H). $^{13}$C NMR (126 MHz, DMSO-d$_6$) δ 167.06, 164.74, 153.97,

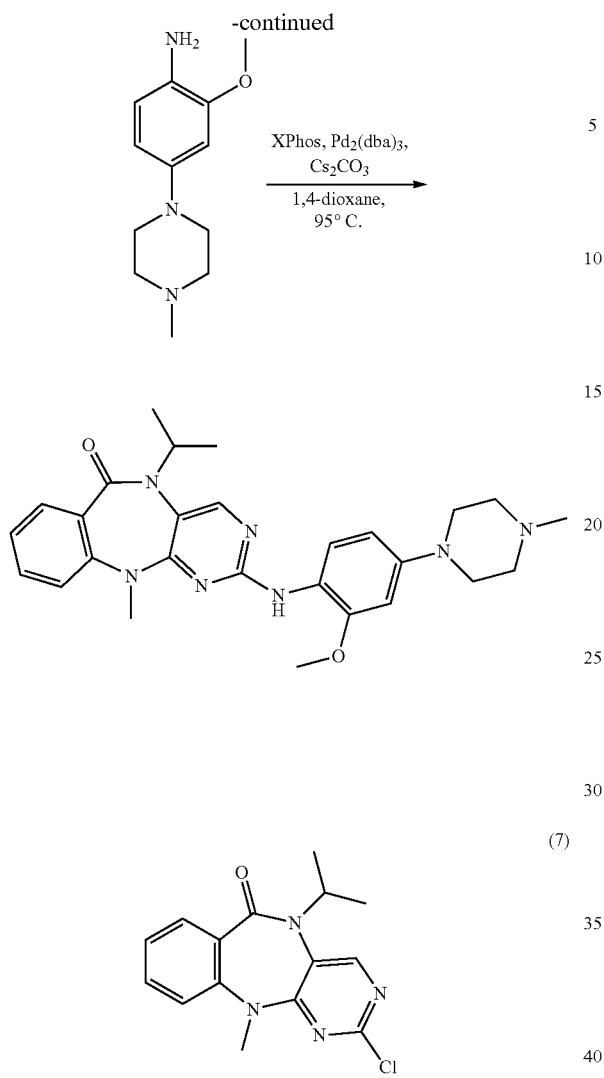

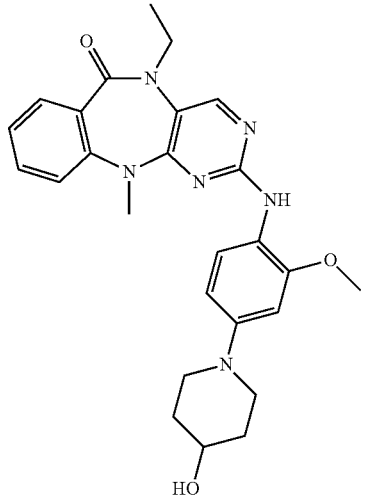 [SMILES: CCN1C(=O)c2ccccc2N(C)c2nc(Nc3ccc(N4CCC(O)CC4)cc3OC)ncc21]

Compound 5: 5-ethyl-2-((4-(4-hydroxypiperidin-1-yl)-2-methoxyphenyl)amino)-11-methyl-5,11-dihydro-6H-benzo[e]pyrimido[5,4-b][1,4]diazepin-6-one (XMD9-22)

$^1$H NMR (500 MHz, DMSO-d$_6$) δ 8.33 (s, 1H), 7.94 (s, 1H), 7.72 (d, J=8.8 Hz, 1H), 7.63 (dd, J=7.7, 1.8 Hz, 1H), 7.50-7.45 (m, 1H), 7.21 (d, J=8.4 Hz, 1H), 7.16 (t, J=7.4 Hz, 1H), 6.61 (d, J=2.6 Hz, 1H), 6.49 (dd, J=8.8, 2.6 Hz, 1H), 4.15-4.01 (m, 1H), 3.80 (s, 3H), 3.62 (tq, J=8.5, 4.4 Hz, 1H), 3.55-3.46 (m, 2H), 3.35 (s, 2H), 3.27 (s, 3H), 1.83 (dq, J=12.4, 4.0 Hz, 2H), 1.50 (dtd, J=13.0, 9.5, 3.8 Hz, 2H), 1.15 (t, J=7.1 Hz, 3H). MS (ESI) m/z 475 (M+H)$^+$ In Scheme 4, 2-chloro-5-isopropyl-11-methyl-5,11-dihydro-6H-benzo[e]pyrimido[5,4-b][1,4]diazepin-6-one (7) can be synthesized as follows: 1, 2-chloro-11-methyl-5,11-dihydro-6H-benzo[e]pyrimido[5,4-b][1,4]diazepin-6-one (3) (500 mg, 1.9 mmol), Cs$_2$CO$_3$ (1.3 g, 4.0 mmol) and isopropyl iodide (250 μL, 2.2 mmol) were dissolved in DMA (5 mL) and heated to 70° C. for 2 h. The solvent was evaporated and the residue purified by silica column chromatography (0-5% MeOH in DCM) to give the title compound (167 mg, 29%). $^1$H NMR (500 MHz, DMSO-d$_6$) δ 8.58 (s, 1H), 7.69 (dd, J=7.8, 1.7 Hz, 1H), 7.52 (ddd, J=8.3, 7.3, 1.7 Hz, 1H), 7.27 (dd, J=8.5, 1.1 Hz, 1H), 7.21 (td, J=7.5, 1.0 Hz, 1H), 4.52 (hept, J=6.8 Hz, 1H), 3.35 (s, 3H), 1.80-0.85 (m, 6H). $^{13}$C NMR (126 MHz, DMSO-d$_6$) δ 167.49, 166.18, 154.39, 148.79, 133.11, 132.29, 126.90, 125.90, 124.56, 118.46, 54.22, 36.01. MS (ESI) m/z 304 (M+H)$^+$ Other steps in Scheme 4 can be performed as described in Scheme 1.

v. Other Compounds

All other compounds were prepared from intermediates (4), (5), (6) or (7) by analogous methods to XMD8-85 (Compound 1) as described herein.

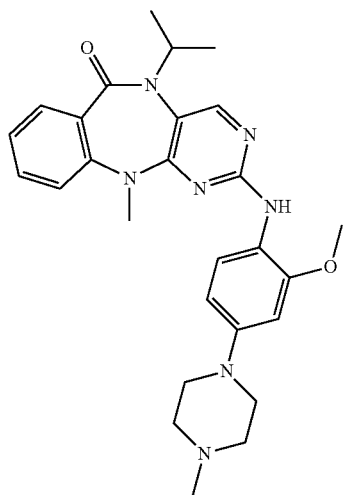 [SMILES: COc1cc(N2CCN(C)CC2)ccc1Nc1ncc2c(n1)N(C)c1ccccc1C(=O)N2C(C)C]

Compound 6: 5-isopropyl-2-((2-methoxy-4-(4-methylpiperazin-1-yl)phenyl)amino)-11-methyl-5,11-dihydro-6H-benzo[e]pyrimido[5,4-b][1,4]diazepin-6-one (FMF-03-149-1)

$^1$H NMR (500 MHz, DMSO-d$_6$) δ 9.71 (s, 1H), 8.25 (s, 1H), 8.11 (s, 1H), 7.78 (d, J=8.7 Hz, 1H), 7.66 (dd, J=7.7, 1.7 Hz, 1H), 7.46 (ddd, J=8.7, 7.2, 1.7 Hz, 1H), 7.27-7.12 (m, 2H), 6.71 (d, J=2.6 Hz, 1H), 6.57 (dd, J=8.8, 2.6 Hz, 1H), 4.60 (hept, J=6.8 Hz, 1H), 3.82 (s, 6H), 3.54 (d, J=12.2 Hz, 2H), 3.28 (s, 3H), 3.17 (dd, J=12.8, 9.2 Hz, 2H), 2.94 (t, J=12.7 Hz, 2H), 2.88 (d, J=3.3 Hz, 3H), 1.49-1.36 (m, 3H), 1.08 (d, J=6.8 Hz, 3H). MS (ESI) m/z 488 (M+H)$^+$

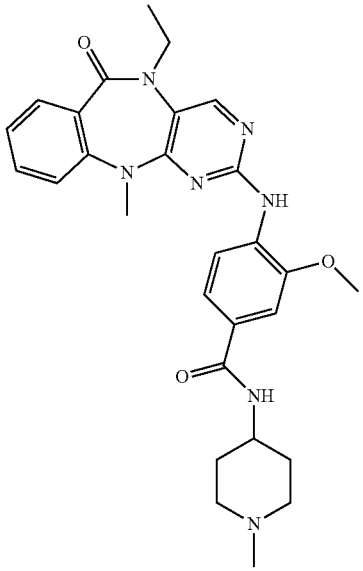 [SMILES: CCN1C(=O)c2ccccc2N(C)c2nc(Nc3ccc(C(=O)NC4CCN(C)CC4)cc3OC)ncc21]

Compound 7: 4-((5-ethyl-11-methyl-6-oxo-6,11-dihydro-5H-benzo[e]pyrimido[5,4-b][1,4]diazepin-2-yl)amino)-3-methoxy-N-(1-methylpiperidin-4-yl)benzamide (FMF-03-059-1)

$^1$H NMR (500 MHz, DMSO-d$_6$) δ 9.38 (s, 1H), 8.49 (s, 1H), 8.36 (dd, J=8.0, 5.3 Hz, 2H), 8.23-8.16 (m, 1H), 7.66 (dd, J=7.8, 1.7 Hz, 1H), 7.60-7.54 (m, 1H), 7.54-7.46 (m, 2H), 7.25 (dt, J=8.4, 1.9 Hz, 1H), 7.19 (td, J=7.5, 1.1 Hz, 1H), 4.61 (br s, 2H), 4.11-3.98 (m, 1H), 3.95 (d, J=3.8 Hz, 3H), 3.49 (d, J=12.2 Hz, 2H), 3.36 (s, 3H), 3.17-3.05 (m, 2H), 2.79 (d, J=4.6 Hz, 3H), 2.08-1.98 (m, 2H), 1.82-1.69 (m, 2H), 1.18 (t, J=7.0 Hz, 3H). MS (ESI) m/z 516 (M+H)$^+$

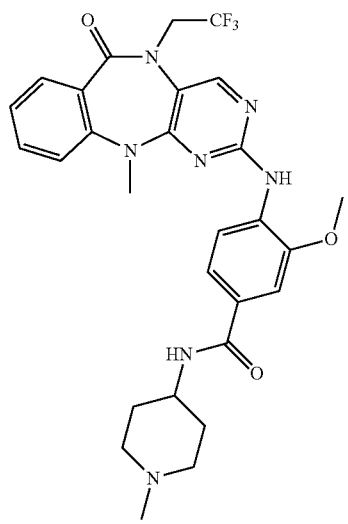 [SMILES: COc1cc(C(=O)NC2CCN(C)CC2)ccc1Nc1ncc2c(n1)N(C)c1ccccc1C(=O)N2CC(F)(F)F]

Compound 8: 3-methoxy-4-((11-methyl-6-oxo-5-(2,2,2-trifluoroethyl)-6,11-dihydro-5H-benzo[e]pyrimido[5,4-b][1,4]diazepin-2-yl)amino)-N-(1-methylpiperidin-4-yl)benzamide (FMF-03-148-1)

$^1$H NMR (500 MHz, DMSO-d$_6$) δ 9.43 (s, 1H), 8.63 (s, 1H), 8.38 (d, J=7.5 Hz, 1H), 8.34 (d, J=10.0 Hz, 1H), 8.29 (d, J=8.4 Hz, 1H), 7.71 (dd, J=7.7, 1.7 Hz, 1H), 7.56 (ddt, J=10.1, 8.7, 3.3 Hz, 2H), 7.53-7.48 (m, 1H), 7.30 (dd, J=8.2, 3.0 Hz, 1H), 7.25-7.20 (m, 1H), 5.27 (s, 1H), 4.62 (s, 1H), 4.17-3.97 (m, 1H), 3.94 (d, J=3.7 Hz, 3H), 3.48 (s, 2H), 3.37 (d, J=2.8 Hz, 3H), 3.18-3.05 (m, 2H), 2.79 (d, J=4.6 Hz, 3H), 2.08-2.01 (m, 2H), 1.78 (qd, J=13.7, 3.9 Hz, 2H).
MS (ESI) m/z 570 (M+H)$^+$

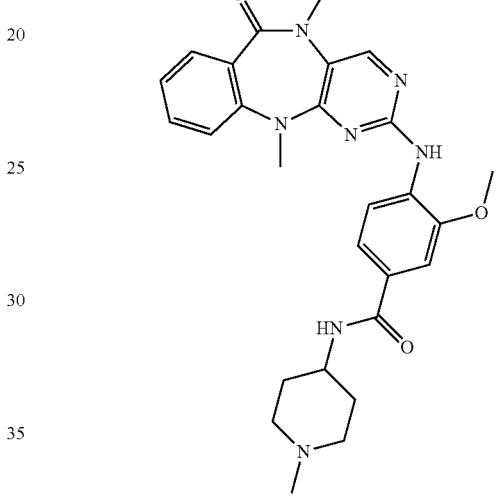

Compound 9: 4-((5-isopropyl-11-methyl-6-oxo-6,11-dihydro-5H-benzo[e]pyrimido[5,4-b][1,4]diazepin-2-yl)amino)-3-methoxy-N-(1-methylpiperidin-4-yl)benzamide (FMF-03-151-1)

$^1$H NMR (500 MHz, DMSO-d$_6$) δ 9.44 (s, 1H), 8.39 (s, 1H), 8.33 (d, J=8.4 Hz, 1H), 8.26 (s, 1H), 7.68 (dd, J=7.7, 1.8 Hz, 1H), 7.57 (dd, J=8.5, 1.9 Hz, 1H), 7.52-7.46 (m, 2H), 7.24 (dt, J=8.7, 1.9 Hz, 1H), 7.18 (td, J=7.5, 1.0 Hz, 1H), 4.59 (p, J=6.8 Hz, 1H), 4.20-3.98 (m, 1H), 3.94 (d, J=3.9 Hz, 3H), 3.49 (d, J=12.2 Hz, 2H), 3.36 (s, 3H), 3.17-3.06 (m, 2H), 2.79 (d, J=4.6 Hz, 3H), 2.09-1.99 (m, 2H), 1.78 (qd, J=13.6, 3.9 Hz, 2H), 1.47 (s, 3H), 1.11 (s, 3H). MS (ESI) m/z 530 (M+H)$^+$

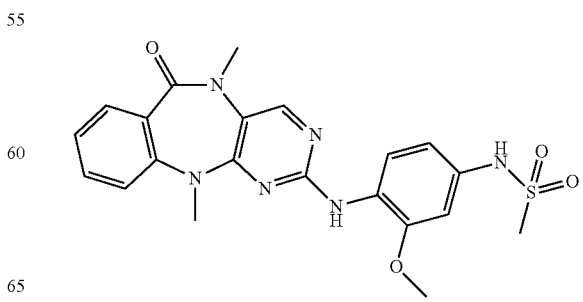

Compound 10: N-(4-((5,11-dimethyl-6-oxo-6,11-dihydro-5H-benzo[e]pyrimido[5,4-b][1,4]diazepin-2-yl)amino)-3-methoxyphenyl)methanesulfonamide (FMF-03-047-1)

¹H NMR (500 MHz, DMSO-d₆) δ 9.57 (s, 1H), 8.36 (s, 1H), 8.16 (s, 1H), 7.98 (d, J=8.6 Hz, 1H), 7.69 (dd, J=7.8, 1.7 Hz, 1H), 7.51 (ddd, J=8.7, 7.2, 1.8 Hz, 1H), 7.26 (d, J=8.3 Hz, 1H), 7.18 (t, J=7.5 Hz, 1H), 6.91 (d, J=2.3 Hz, 1H), 6.84 (dd, J=8.6, 2.3 Hz, 1H), 3.82 (s, 3H), 3.39 (s, 3H), 3.32 (s, 4H), 2.98 (s, 3H). MS (ESI) m/z 455 (M+H)⁺

Compound 11: N-(4-((5-ethyl-11-methyl-6-oxo-6,11-dihydro-5H-benzo[e]pyrimido[5,4-b][1,4]diazepin-2-yl)amino)-3-methoxyphenyl)methanesulfonamide (FMF-03-087-1)

¹H NMR (500 MHz, DMSO-d₆) δ 9.57 (s, 1H), 8.39 (s, 1H), 8.16 (s, 1H), 7.98 (d, J=8.6 Hz, 1H), 7.64 (dd, J=7.7, 1.7 Hz, 1H), 7.53-7.44 (m, 1H), 7.24 (dd, J=8.4, 0.9 Hz, 1H), 7.17 (td, J=7.5, 1.0 Hz, 1H), 6.91 (d, J=2.4 Hz, 1H), 6.84 (dd, J=8.6, 2.3 Hz, 1H), 4.02 (s, 2H), 3.82 (s, 3H), 3.31 (s, 3H), 2.98 (s, 3H), 1.16 (t, J=7.1 Hz, 3H). MS (ESI) m/z 469 (M+H)⁺

Compound 12: N-(3-methoxy-4-((11-methyl-6-oxo-5-(2,2,2-trifluoroethyl)-6,11-dihydro-5H-benzo[e]pyrimido[5,4-b][1,4]diazepin-2-yl)amino)phenyl)methanesulfonamide (FMF-03-147-1)

¹H NMR (500 MHz, DMSO-d₆) δ 8.65 (s, 1H), 7.72 (dd, J=7.8, 1.7 Hz, 1H), 7.60-7.54 (m, 1H), 7.32 (dd, J=8.5, 1.0 Hz, 1H), 7.23 (td, J=7.5, 0.9 Hz, 1H), 6.80 (s, 1H), 6.70 (d, J=1.3 Hz, 2H), 3.75 (s, 3H), 3.65 (s, 2H), 3.29 (s, 3H), 3.17 (s, 3H). MS (ESI) m/z 523 (M+H)⁺

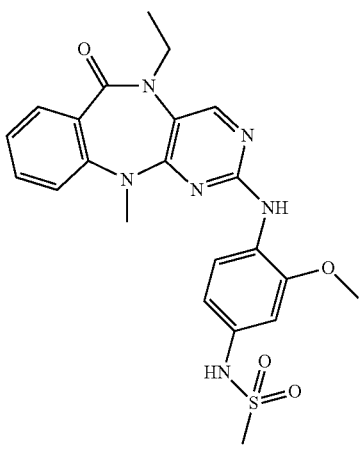 [SMILES: CCN1C(=O)c2ccccc2N(C)c2nc(Nc3ccc(NS(C)(=O)=O)cc3OC)ncc21]

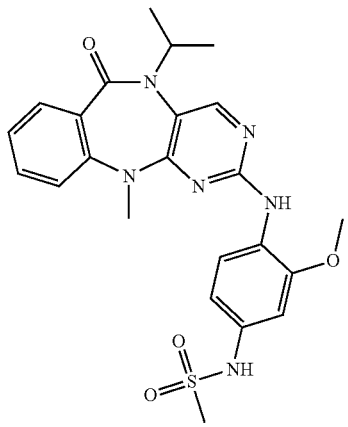

Compound 13: N-(4-((5-isopropyl-11-methyl-6-oxo-6,11-dihydro-5H-benzo[e]pyrimido[5,4-b][1,4]diazepin-2-yl)amino)-3-methoxyphenyl)methanesulfonamide (FMF-03-150-2)

¹H NMR (500 MHz, DMSO-d₆) δ 9.57 (s, 1H), 8.30 (s, 1H), 8.16 (s, 1H), 7.96 (d, J=8.6 Hz, 1H), 7.66 (dd, J=7.8, 1.7 Hz, 1H), 7.50-7.43 (m, 1H), 7.25-7.21 (m, 2H), 7.16 (td, J=7.5, 1.0 Hz, 1H), 6.91 (d, J=2.3 Hz, 1H), 6.83 (dd, J=8.6, 2.3 Hz, 1H), 4.55 (dq, J=38.7, 6.8 Hz, 1H), 3.81 (s, 3H), 3.30 (s, 3H), 2.98 (s, 3H), 1.44 (d, J=5.6 Hz, 4H), 1.09 (d, J=6.6 Hz, 4H).
MS (ESI) m/z 483 (M+H)⁺

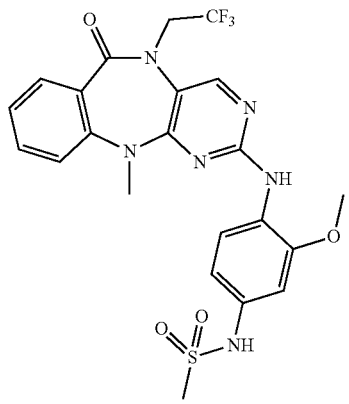 [SMILES: COc1cc(NS(C)(=O)=O)ccc1Nc1ncc2c(n1)N(C)c1ccccc1C(=O)N2CC(F)(F)F]

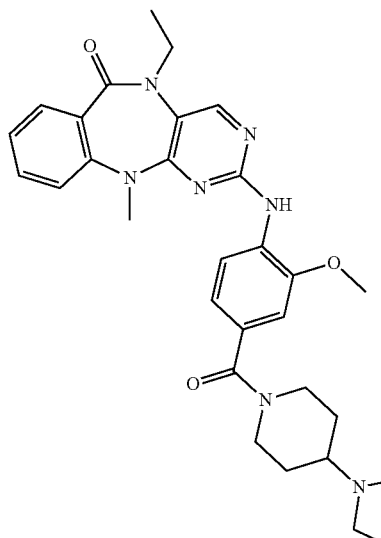

Compound 14: 5-ethyl-2-((2-methoxy-4-(4-(pyrrolidin-1-yl)piperidine-1-carbonyl)phenyl)amino)-11-methyl-5,11-dihydro-6H-benzo[e]pyrimido[5,4-b][1,4]diazepin-6-one (FMF-03-058-2)

$^1$H NMR (500 MHz, DMSO-d$_6$) δ 9.78 (s, 1H), 8.47 (s, 1H), 8.29 (d, J=8.2 Hz, 1H), 8.20 (s, 1H), 7.66 (dd, J=7.7, 1.7 Hz, 1H), 7.50 (ddd, J=8.7, 7.3, 1.8 Hz, 1H), 7.25 (dd, J=8.4, 1.0 Hz, 1H), 7.19 (td, J=7.5, 1.0 Hz, 1H), 7.09-7.00 (m, 2H), 4.05 (s, 2H), 3.91 (s, 3H), 3.53 (s, 2H), 3.47-3.37 (m, 1H), 3.35 (s, 3H), 3.16-3.05 (m, 2H), 2.96 (s, 1H), 2.55 (s, 2H), 2.09 (s, 2H), 2.06-1.92 (m, 2H), 1.93-1.78 (m, 2H), 1.63-1.49 (m, 1H), 1.17 (t, J=7.1 Hz, 3H).
MS (ESI) m/z 556 (M+H)$^+$ Compound 16: 5-ethyl-2-((2-methoxy-4-(2-(4-methylpiperazin-1-yl)ethoxy)phenyl)amino)-11-methyl-5,11-dihydro-6H-benzo[e]pyrimido[5,4-b][1,4]diazepin-6-one (FMF-03-086-1)

$^1$H NMR (500 MHz, DMSO-d$_6$) δ 8.35 (s, 1H), 8.14 (s, 1H), 7.79 (d, J=8.7 Hz, 1H), 7.64 (dd, J=7.7, 1.7 Hz, 1H), 7.48 (ddd, J=8.7, 7.2, 1.8 Hz, 1H), 7.25-7.12 (m, 2H), 6.66 (d, J=2.7 Hz, 1H), 6.58 (dd, J=8.8, 2.7 Hz, 1H), 4.21 (t, J=5.2 Hz, 2H), 4.05 (s, 2H), 3.81 (s, 3H), 3.41 (s, 4H), 3.27 (s, 3H), 3.17 (s, 4H), 2.82 (s, 3H), 1.16 (t, J=7.1 Hz, 3H).
MS (ESI) m/z 518 (M+H)$^+$

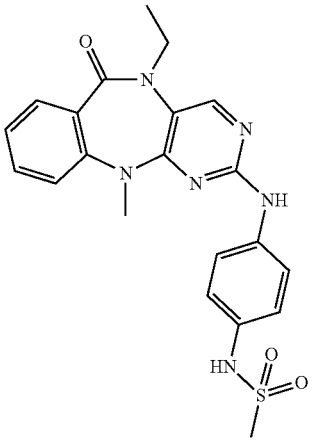 [SMILES: CCN1C(=O)c2ccccc2N(C)c2nc(Nc3ccc(NS(C)(=O)=O)cc3)ncc21]

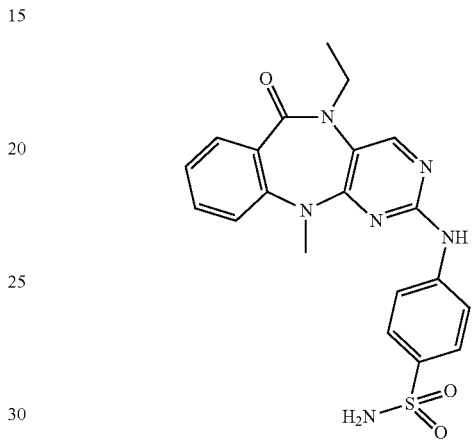

Compound 15: N-(4-((5-ethyl-11-methyl-6-oxo-6,11-dihydro-5H-benzo[e]pyrimido[5,4-b][1,4]diazepin-2-yl)amino)phenyl)methanesulfonamide (FMF-03-083-1)

$^1$H NMR (500 MHz, DMSO-d$_6$) δ 9.66 (s, 1H), 9.44 (s, 1H), 8.43 (s, 1H), 7.74-7.68 (m, 2H), 7.64 (dd, J=7.7, 1.7 Hz, 1H), 7.48 (ddd, J=8.8, 7.2, 1.7 Hz, 1H), 7.26 (dd, J=8.4, 1.0 Hz, 1H), 7.16 (d, J=8.8 Hz, 3H), 4.15-3.59 (m, 2H), 3.35 (s, 3H), 2.93 (s, 3H), 1.17 (t, J=7.0 Hz, 3H).
MS (ESI) m/z 439 (M+H)$^+$ Compound 17: 4-((5-ethyl-11-methyl-6-oxo-6,11-dihydro-5H-benzo[e]pyrimido[5,4-b][1,4]diazepin-2-yl)amino)benzenesulfonamide (FMF-03-088-1/-2)

$^1$H NMR (500 MHz, DMSO-d$_6$) δ 10.07 (s, 1H), 8.51 (s, 1H), 7.95-7.88 (m, 2H), 7.79-7.72 (m, 2H), 7.66 (dd, J=7.8, 1.7 Hz, 1H), 7.53-7.47 (m, 1H), 7.27 (dd, J=8.4, 1.0 Hz, 1H), 7.21-7.15 (m, 3H), 3.53 (s, 2H), 3.39 (s, 3H), 1.18 (t, J=7.1 Hz, 3H). MS (ESI) m/z 425 (M+H)$^+$

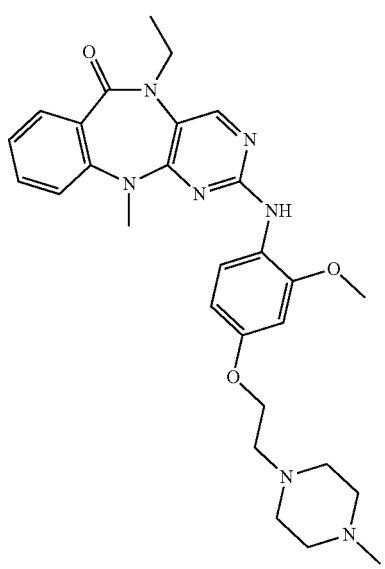 [SMILES: CCN1C(=O)c2ccccc2N(C)c2nc(Nc3ccc(OCCN4CCN(C)CC4)cc3OC)ncc21]

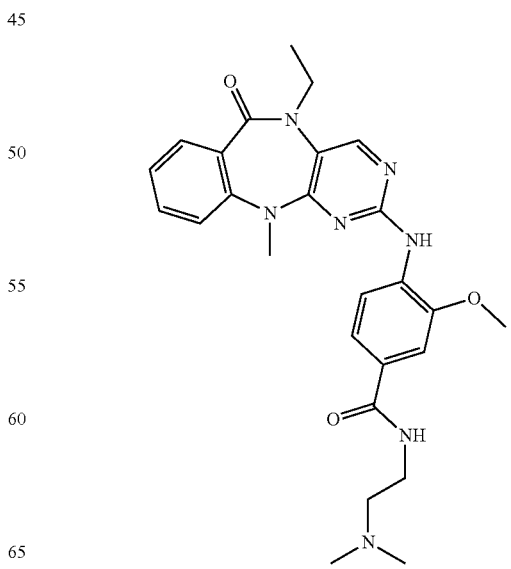

Compound 18: N-(2-(dimethylamino)ethyl)-4-((5-ethyl-11-methyl-6-oxo-6,11-dihydro-5H-benzo[e]pyrimido[5,4-b][1,4]diazepin-2-yl)amino)-3-methoxybenzamide (FMF-03-061-1)

$^1$H NMR (500 MHz, DMSO-$d_6$) δ 9.41 (s, 1H), 8.64 (t, J=5.7 Hz, 1H), 8.50 (s, 1H), 8.38 (d, J=8.5 Hz, 1H), 8.23 (s, 1H), 7.66 (dd, J=7.7, 1.7 Hz, 1H), 7.57 (dd, J=8.5, 1.9 Hz, 1H), 7.53 (d, J=2.0 Hz, 1H), 7.50 (ddd, J=8.8, 7.2, 1.7 Hz, 1H), 7.25 (dd, J=8.4, 1.0 Hz, 1H), 7.19 (td, J=7.5, 1.0 Hz, 1H), 4.09 (s, 2H), 3.94 (s, 3H), 3.62 (q, J=5.9 Hz, 2H), 3.36 (s, 3H), 3.28 (q, J=5.9 Hz, 2H), 2.87 (d, J=4.7 Hz, 6H), 1.18 (t, J=7.0 Hz, 3H). MS (ESI) m/z 490 (M+H)$^+$

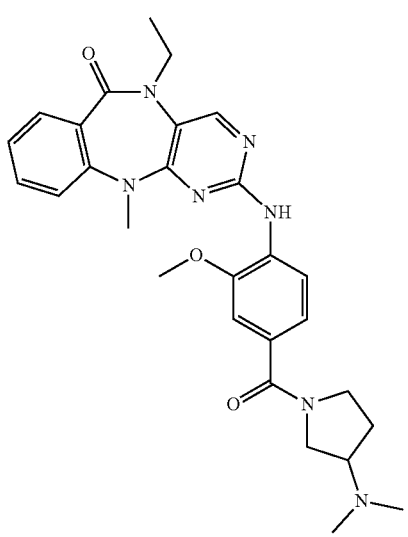 [SMILES: CCN1C(=O)c2ccccc2N(C)c2nc(Nc3ccc(C(=O)N4CCC(N(C)C)C4)cc3OC)ncc21]

Compound 19: 2-((4-(3-(dimethylamino)pyrrolidine-1-carbonyl)-2-methoxyphenyl)amino)-5-ethyl-11-methyl-5,11-dihydro-6H-benzo[e]pyrimido[5,4-b][1,4]diazepin-6-one (FMF-03-067-1)

$^1$H NMR (500 MHz, DMSO-$d_6$) δ 10.17 (s, 1H), 8.48 (s, 1H), 8.32 (d, J=8.2 Hz, 1H), 8.22 (s, 1H), 7.66 (dd, J=7.7, 1.7 Hz, 1H), 7.50 (ddd, J=8.7, 7.3, 1.7 Hz, 1H), 7.27-7.15 (m, 4H), 3.95 (s, 2H), 3.92 (s, 3H), 3.75-3.66 (m, 2H), 3.61 (s, 2H), 3.35 (s, 3H), 2.85 (s, 6H), 2.40-2.26 (m, 1H), 2.12 (t, J=10.6 Hz, 1H), 1.17 (t, J=7.0 Hz, 3H).

MS (ESI) m/z 516 (M+H)$^+$

Selectivity Data

FIG. 1 illustrates the selectivity of Compound 2 (FMF-03-146-1) at a concentration of 1 μM against a panel of 468 human kinases and human mutant kinases. These selectivity data were generated using KINOMEscan® platform and these images were generated using TREEspot™ Software Tool and reprinted with permission from KINOMEscan®, a division of DiscoveRx Corporation, © DISCOVERX CORPORATION 2010.

Biochemical Assay
General Material
Lysis Buffer
  50 mM HEPES pH 7.8
  350 mM NaCl
  20 mM imidazole
  5% Glycerol
Wash Buffer 1—Same as Lysis
Wash Buffer 2 and 3—Same as lysis but 25 mM Imidazole
Elution Buffer—Same as lysis but 300 mM Imidazole
S200 Gel filtration Buffer
  10 mM HEPES pH 7.8
  700 mM NaCl
  1 mM MgCl2
  5% Glycerol
Substrate for Gel Shift Assay
  5-FAM-KKLRRTLSVA-COOH
DCLK1 Plasmid Construct The DNA construct consisting of N-terminally 6-His tagged human DCLK1 residues G351-H689 was prepared. Thus prepared plasmid was co-transformed with lambda phosphatase under chloramphenicol selection into BL21 (DE3) E. coli cells.

DCLK1 Protein Purification

Protein expression was induced from the DCLK1 plasmid with 0.6 mM IPTG and expression was allowed to continue for about 10 hours at a temperature of 18° C. Cells was harvested by centrifugation and resuspended in Lysis buffer with protease inhibitors (1 mM Benzamidine and 1 mM PMSF). Lysis was performed by passing 3 times through a homogenizer. Lysate was centrifuged at 20K for 1 hour at a temperature of 4° C. and the supernatant was filtered through a 0.2 micron membrane. Protein was loaded on nickel (Ni)-NTA resin, washed with Wash buffers, and eluted with 300 mM imidazole buffer. Eluate was concentrated to 2 mL and passed over a Superdex 5200 column.

DCLK1 Mobility Shift Assay (Gel Shift Assay)

DCLK1 kinase activity was measured in vitro using an electrophoretic mobility shift assay. The reaction was assembled in a 384-well plate in a total volume of 20 μl. The reaction contained 30 nM recombinant DCLK1, one DCLK1 inhibitor or DMSO, 100 μM ATP and 1 μM FAM-labeled peptide substrate in a buffer (100 mM HEPES pH 7.5, 0.003% Brij-35, 0.004% Tween-20, 10 mM MgCl$_2$, and 2 mM DTT). DCLK1 inhibitors were dispensed using a Labcyte Echo liquid handler. The reaction was incubated at room temperature for two hours and quenched by addition of 40 μL of termination buffer (100 mM HEPES pH 7.3, 0.015% Brij-35, 0.1% CR-3, 1×CR-8, and 40 mM EDTA). Substrate and product peptides present in each sample were electrophoretically separated and detected using 12-channel LabChip3000 microfluidic capillary electrophoresis instrument (Caliper Life Sciences, Waltham Mass., USA). The change in the relative fluorescence intensities of substrate and product peaks (reflecting enzyme activity) was measured. Capillary electrophoregrams were analyzed using HTS Well Analyzer software (Caliper Life Sciences, Waltham Mass., USA).

The kinase activity in each sample was determined as the product-to-sum ratio (PSR):P/(S+P), where P is the peak height of the product peptide and S is the peak height of the substrate peptide. Negative control samples (DMSO in the absence of inhibitor) and positive control samples (100% inhibition, a tested DCLK1 inhibitor) were assembled in replicates and were used to calculate percent inhibition values for each compound at each concentration.

Percent inhibition (% Inhibition) was determined using the following equation:

$$\% \text{ Inhibition} = 100 \times \frac{(PSR_{0\%} - PSR_{inh})}{(PSR_{0\%} - PSR_{100\%})},$$

where $PSR_{inh}$ is the product-sum ratio in the presence of inhibitor, $PSR_{0\%}$ is the average product-sum ration in the absence of inhibitor and $PSR_{100\%}$ is the average product-sum ratio in 100%-inhibition control samples.

The DCLK1 candidate inhibitors were tested in 8-point dose-response format on each assay plate. The $IC_{50}$ values were determined by fitting the inhibition curves by an eight dose-response model using GraphPad Prism 7 software.

Figure 2:
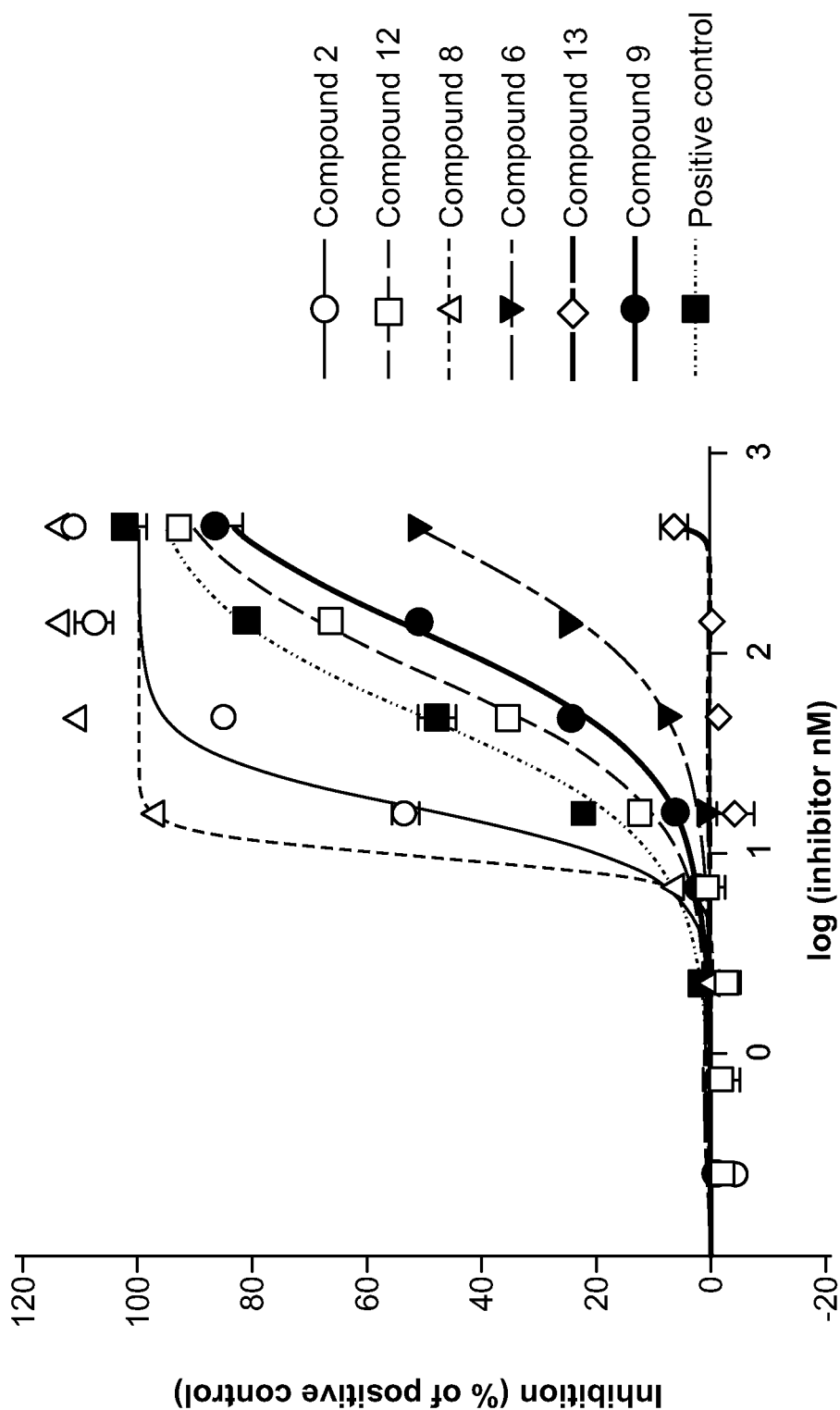
FIG. 2 shows inhibition profiles ($IC_{50}$) of compounds of the invention against DCLK1.

FIG. 2 shows the thus obtained $IC_{50}$ values of Compound 2, Compound 12, Compound 8, Compound 6, Compound 13 and Compound 9. In particular, the $IC_{50}$ values of Compound 2 and Compound 8 were substantially decreased from the $IC_{50}$ value of the positive control.

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended with be encompassed by the following claims.

REFERENCES

1. Reiner, O.; Coquelle, F. M.; Peter, B.; Levy, T.; Kaplan, A.; Sapir, T.; Orr, I.; Barkai, N.; Eichele, G.; Bergmann, S., The evolving doublecortin (DCX) superfamily. *BMC Genomics* 2006, 7 (1), 1-16.
2. The Cancer Genome Atlas Research, N., Comprehensive molecular characterization of gastric adenocarcinoma. *Nature* 2014, 513 (7517), 202-209.
3. Győrffy, B.; Surowiak, P.; Budczies, J.; Lánczky, A., Online Survival Analysis Software to Assess the Prognostic Value of Biomarkers Using Transcriptomic Data in Non-Small-Cell Lung Cancer. *PLoS ONE* 2013, 8 (12), e82241.
4. (a) Ito, H.; Tanaka, S.; Akiyama, Y.; Shimada, S.; Adikrisna, R.; Matsumura, S. Aihara, A.; Mitsunori, Y.; Ban, D.; Ochiai, T.; Kudo, A.; Arii, S.; Yamaoka, S.; Tanabe, M., Dominant Expression of DCLK1 in Human Pancreatic Cancer Stem Cells Accelerates Tumor Invasion and Metastasis. *PLoS ONE* 2016, 11 (1), e0146564; (b) Nakanishi, Y.; Seno, H.; Fukuoka, A.; Ueo, T.; Yamaga, Y.; Maruno, T. Nakanishi, N.; Kanda, K.; Komekado, H.; Kawada, M.; Isomura, A.; Kawada, K.; Sakai, Y.; Yanagita, M.; Kageyama, R.; Kawaguchi, Y.; Taketo, M. M.; Yonehara, S.; Chiba, T., Dclk1 distinguishes between tumor and normal stem cells in the intestine. *Nature genetics* 2013, 45 (1), 98-103; (c) Westphalen, C. B.; Asfaha, S.; Hayakawa, Y.; Takemoto, Y.; Lukin, D. J.; Nuber, A. H.; Brandtner, A.; Setlik, W.; Remotti, H.; Muley, A.; Chen, X.; May, R.; Houchen, C. W.; Fox, J. G.; Gershon, M. D.; Quante, M.; Wang, T. C., Long-lived intestinal tuft cells serve as colon cancer-initiating cells. *The Journal of clinical investigation* 2014, 124 (3), 1283-95; (d) Westphalen, C. B.; Takemoto, Y.; Tanaka, T.; Macchini, M.; Jiang, Z.; Renz, B. W.; Chen, X.; Ormanns, S.; Nagar, K.; Tailor, Y.; May, R.; Cho, Y.; Asfaha, S.; Worthley, D. L.; Hayakawa, Y.; Urbanska, A. M.; Quante, M.; Reichert, M.; Broyde, J.; Subramaniam, P. S.; Remotti, H.; Su, G. H.; Rustgi, A. K.; Friedman, R. A.; Honig, B.; alifano, A.; Houchen, C. W.; Olive, K. P.; Wang, T. C., Dclk1 Defines Quiescent Pancreatic Progenitors that Promote Injury-Induced Regeneration and Tumorigenesis. *Cell Stem Cell* 18 (4), 441-455.

What is claimed:

1. A method of treating pancreatic cancer in a subject, the method comprising administering to the subject a compound of formula F-1:

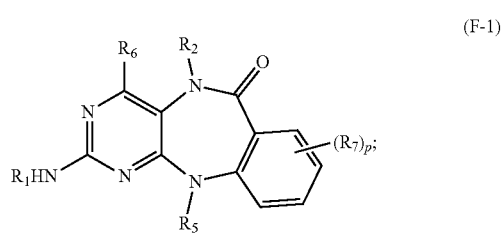

or a pharmaceutically acceptable salt thereof, wherein, $R_1$ is

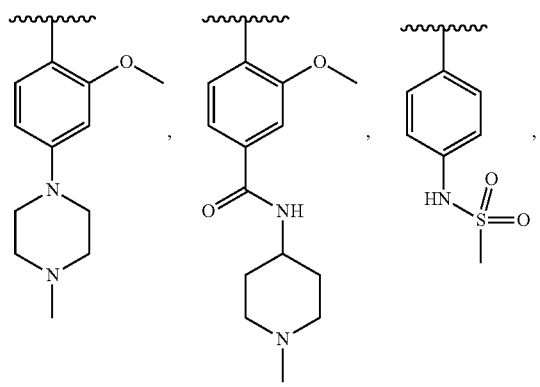

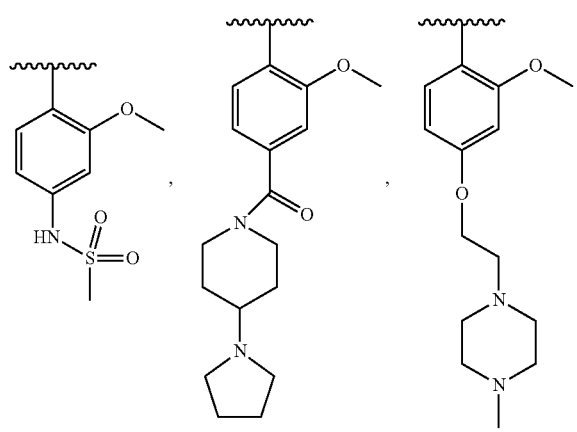

-continued

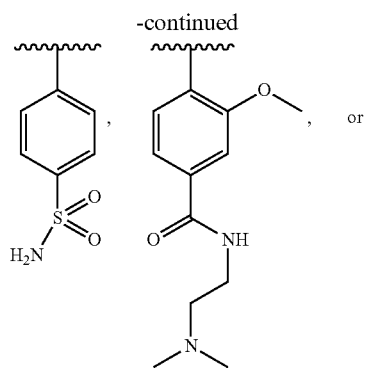

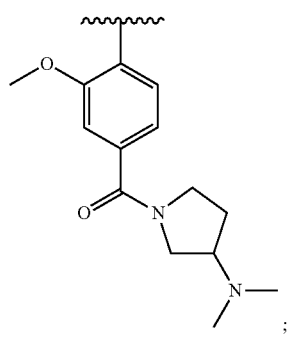

R₂ is —CH₂—CH₂F, —CH₂—CHF₂, or —CH₂—CF₃;

R₅ is hydrogen or methyl; and

R₆ is hydrogen or optionally substituted alkyl;

each R₇ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and p is 0-4.

2. The method of claim 1, wherein the compound is of formula F-1-a:

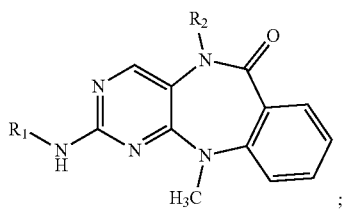

or a pharmaceutically acceptable salt thereof.

3. The method of claim 1, wherein the subject is administered simultaneously or sequentially an additional therapeutic agent, wherein the additional therapeutic agent comprises an anti-inflammatory agent, which is azathioprine, cyclophosphamide, or sulfasalazine, or a chemotherapeutic agent, which is imatinib mesylate, adriamycin, dexamethasone, vincristine, cyclophosphamide, fluorouracil, topotecan, taxol, an interferon, or a platinum derivative.

4. The method of claim 1, wherein the subject is a human.

5. A compound of formula F-1:

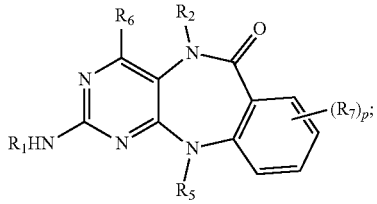

or a pharmaceutically acceptable salt thereof,
wherein,
R₁ is

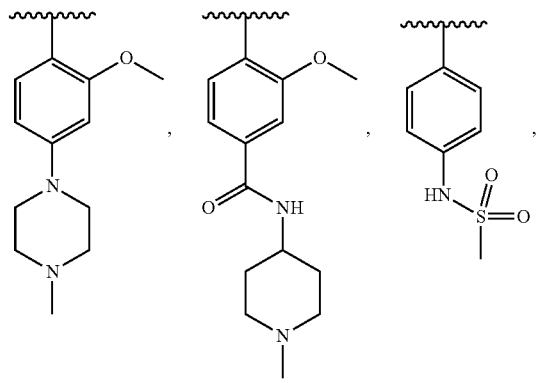

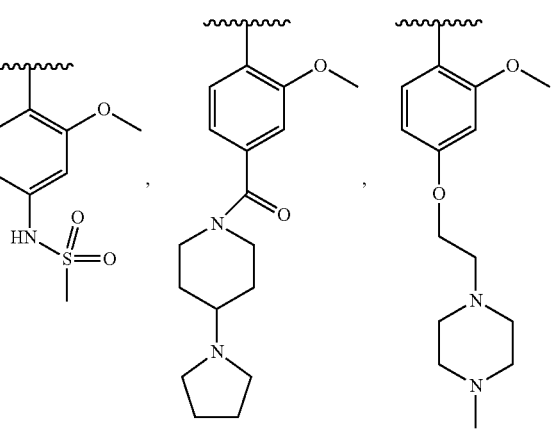

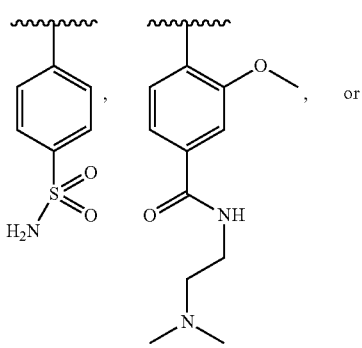

-continued

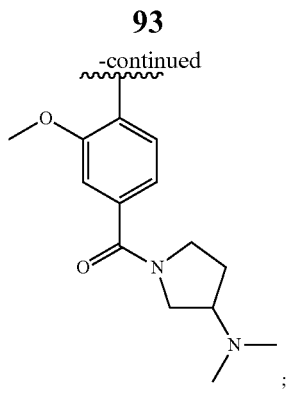

R$_2$ is —CH$_2$—CH$_2$F, —CH$_2$—CHF$_2$, or —CH$_2$—CF$_3$;

R$_5$ is hydrogen or methyl; and

R$_6$ is hydrogen or optionally substituted alkyl;

each R$_7$ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; halo, nitro, or cyano; and p is 0-4.

6. The compound of claim 5, wherein the compound is of formula F-1-a:

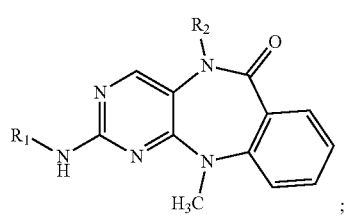

(F-1-a)

or a pharmaceutically acceptable salt thereof.

7. A pharmaceutical composition comprising the compound of claim 5, or a pharmaceutically acceptable salt thereof.

8. The method of claim 1, wherein the compound is

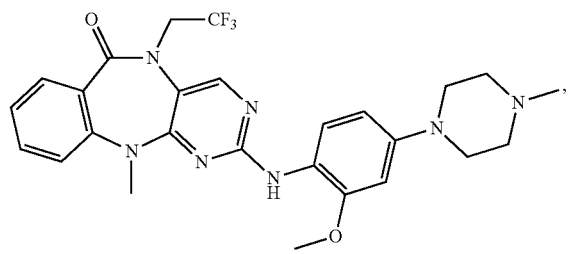

-continued

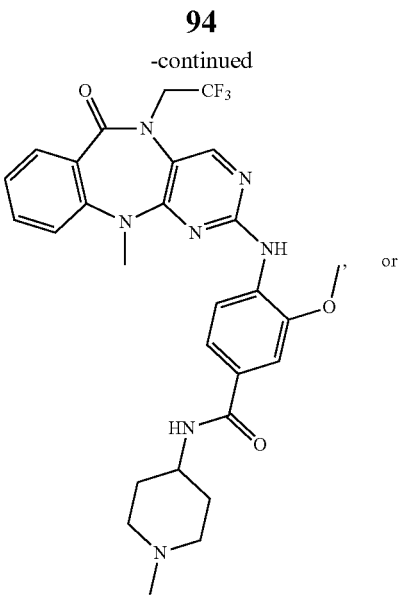

, or

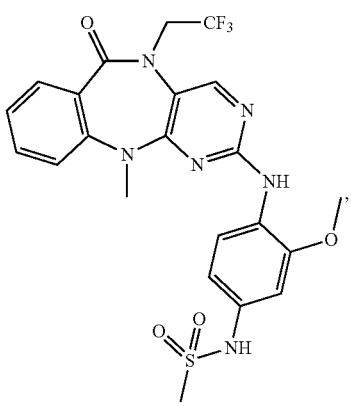

or a pharmaceutically acceptable salt thereof.

9. The compound of claim 5, wherein the compound is

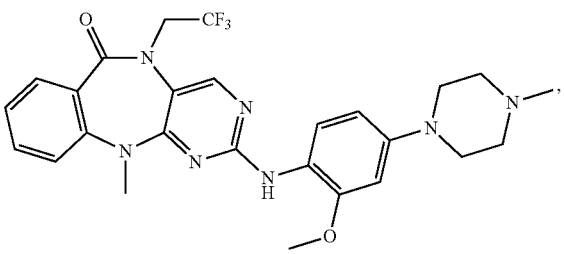

-continued
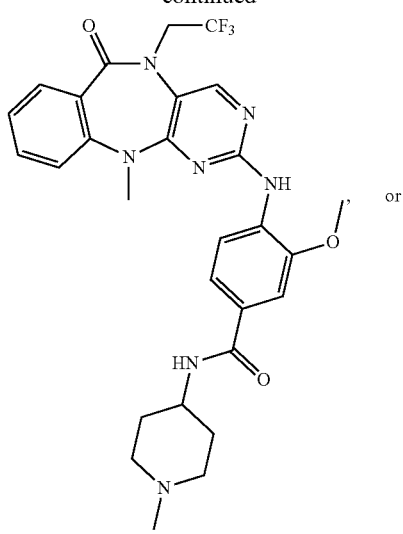
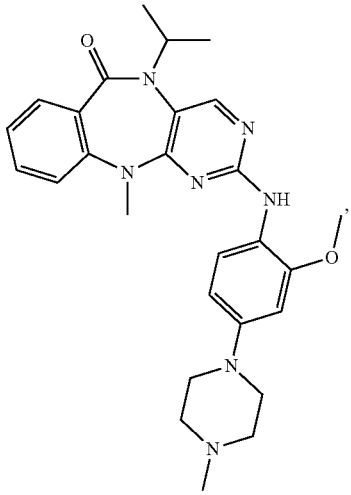
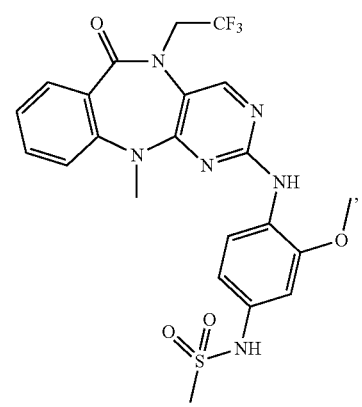
or a pharmaceutically acceptable salt thereof.
10. A compound which is:
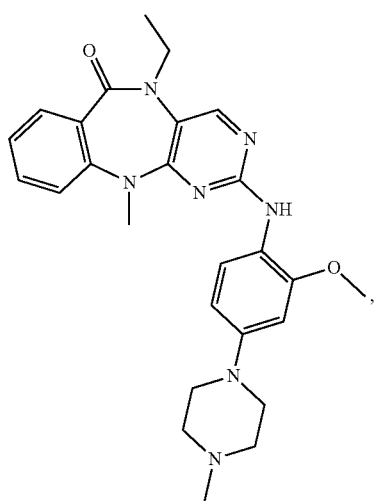
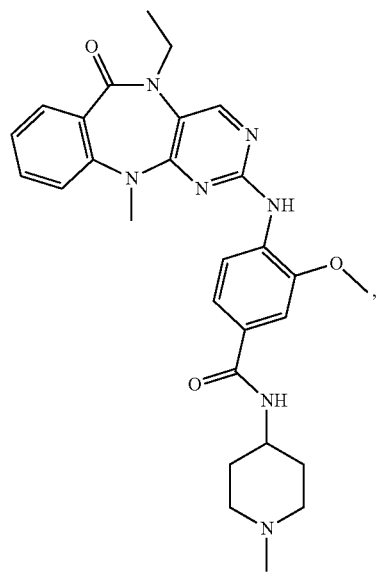
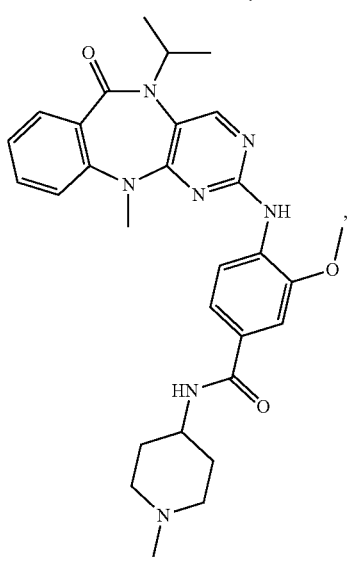

97
-continued
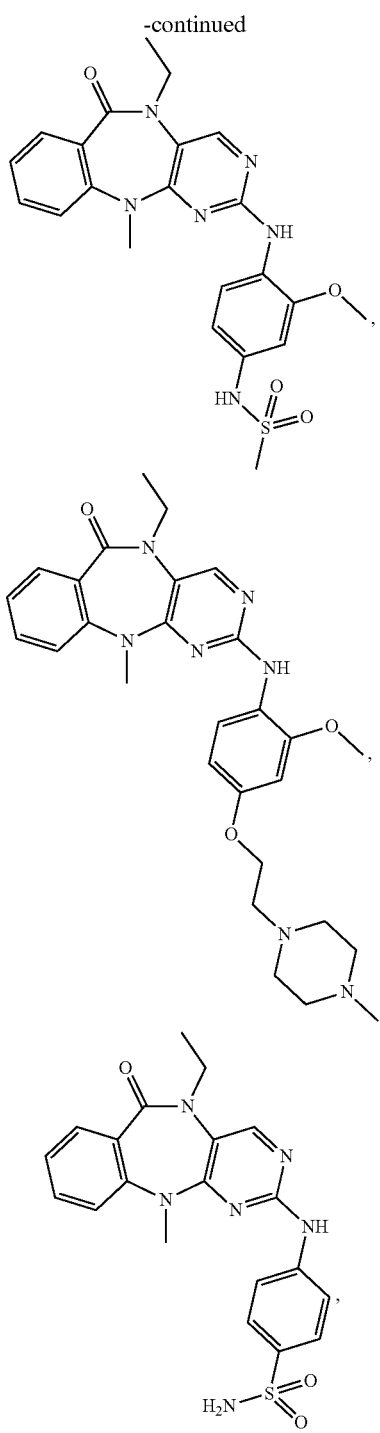
98
-continued
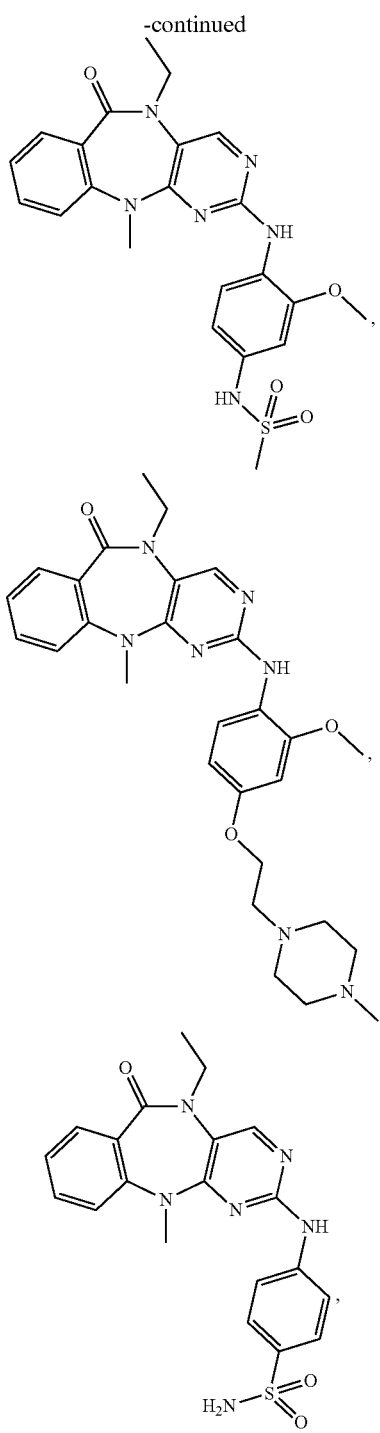
or a pharmaceutically acceptable salt thereof.
11. A method of treating pancreatic cancer in a subject, the method comprising administering to the subject a compound of claim 10, or a pharmaceutically acceptable salt thereof.
* * * * *

UNITED STATES PATENT AND TRADEMARK OFFICE
CERTIFICATE OF CORRECTION

PATENT NO. : 11,028,089 B2
APPLICATION NO. : 16/343102
DATED : June 8, 2021
INVENTOR(S) : Fleur M. Ferguson et al.

It is certified that error appears in the above-identified patent and that said Letters Patent is hereby corrected as shown below:

In the Claims

In Column 97, Line 50:
Add the following text and structures:

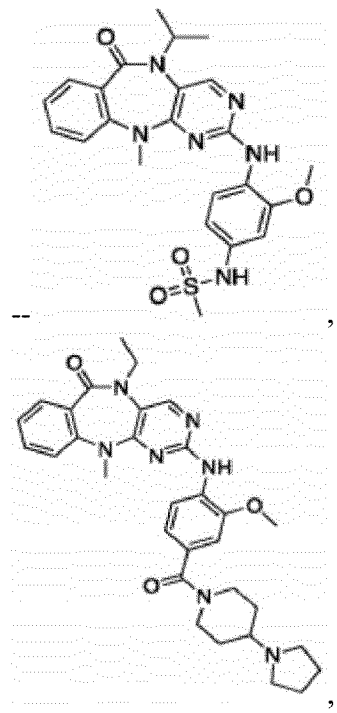

Signed and Sealed this
Twentieth Day of July, 2021

Drew Hirshfeld
*Performing the Functions and Duties of the
Under Secretary of Commerce for Intellectual Property and
Director of the United States Patent and Trademark Office*

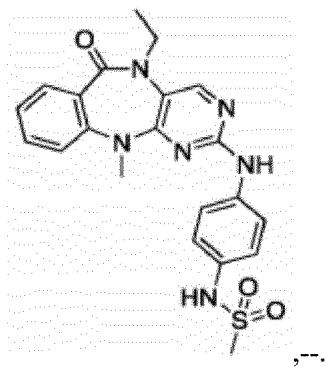
,--.